United States Patent
Barnhart et al.

(10) Patent No.: US 12,364,266 B2
(45) Date of Patent: Jul. 22, 2025

(54) PSEUDOMONAS ISOLATES AND USES THEREOF

(71) Applicant: NOVOZYMES BIOAG A/S, Bagsvaerd (DK)

(72) Inventors: David Michael Barnhart, Apex, NC (US); William Nathan Cude, Durham, NC (US); Kate Brandon Sutton, Raleigh, NC (US); Timothy Liburn, Durham, NC (US); Jonathan Pham, Durham, NC (US); Gregory Stephen Maloney, Creedmoor, NC (US); Jeffrey Layman, Durham, NC (US)

(73) Assignee: NOVOZYMES BIOAG A/S, Bagsvaerd (DK)

( * ) Notice: Subject to any disclaimer, the term of this patent is extended or adjusted under 35 U.S.C. 154(b) by 702 days.

(21) Appl. No.: 17/764,498

(22) PCT Filed: Nov. 18, 2020

(86) PCT No.: PCT/US2020/060968
§ 371 (c)(1),
(2) Date: Mar. 28, 2022

(87) PCT Pub. No.: WO2021/101937
PCT Pub. Date: May 27, 2021

(65) Prior Publication Data
US 2022/0346383 A1 Nov. 3, 2022

Related U.S. Application Data

(60) Provisional application No. 62/937,929, filed on Nov. 20, 2019.

(51) Int. Cl.
*A01N 63/20* (2020.01)
*C12N 1/20* (2006.01)
*C12R 1/38* (2006.01)

(52) U.S. Cl.
CPC ............ *A01N 63/20* (2020.01); *C12N 1/205* (2021.05); *C12R 2001/38* (2021.05)

(58) Field of Classification Search
CPC ..... A01N 63/20; C12N 1/205; C12R 2001/38
See application file for complete search history.

(56) References Cited

U.S. PATENT DOCUMENTS

| | | | |
|---|---|---|---|
| 5,484,464 | A | 1/1996 | Gleddie |
| 5,586,411 | A | 12/1996 | Gleddie |
| 5,695,541 | A | 12/1997 | Kosanke |
| 5,804,208 | A | 9/1998 | Andersch |
| 5,916,029 | A | 6/1999 | Smith |
| 6,569,425 | B2 | 5/2003 | Drahos |
| 6,808,917 | B1 | 10/2004 | Johnson |
| 6,824,772 | B2 | 11/2004 | Drahos |
| 7,429,477 | B2 | 9/2008 | Johnson |
| 8,148,138 | B2 | 4/2012 | Johnson |
| 8,278,247 | B2 | 10/2012 | Hnatowich |
| 8,445,256 | B2 | 5/2013 | Woods |
| 8,883,679 | B2 | 11/2014 | Woods |
| 8,921,089 | B2 | 12/2014 | Kang |
| 8,999,698 | B2 | 4/2015 | Kang |
| 9,017,442 | B2 | 4/2015 | Johnson |
| 9,101,088 | B2 | 8/2015 | Hnatowich |
| 9,234,251 | B2 | 1/2016 | Snyder |
| 9,340,464 | B2 | 5/2016 | Hnatowich |

FOREIGN PATENT DOCUMENTS

| | | |
|---|---|---|
| CN | 105586303 A | 5/2016 |
| KR | 101865810 B1 | 6/2018 |
| RU | 2694565 C1 | 7/2019 |

OTHER PUBLICATIONS

Anonymous, 2018, Genbank No. MH542340.1.
Babu et al, 2015, Journal of environmental management, vol. 151, pp. 160-166.

*Primary Examiner* — Robert A Zeman
(74) *Attorney, Agent, or Firm* — Adam Rucker

(57) ABSTRACT

The present disclosure provides isolated *Pseudomonas koreensis* strains useful for enhancing crop yield, as well as inoculant compositions comprising one or more of the isolated strains, seeds that have been treated with one or more of the isolated strains, and methods of using the isolated strains to enhance root growth, nutrient uptake, chlorophyll content, etc.

20 Claims, No Drawings

Specification includes a Sequence Listing.

SEQUENCE LISTING

<160> NUMBER OF SEQ ID NOS: 1

<210> SEQ ID NO 1
<211> LENGTH: 1329
<212> TYPE: DNA
<213> ORGANISM: Pseudomonas koorensis

<400> SEQUENCE: 1

```
ttcagcggcg acgggtgag taatgcctag gaatctgcct ggtagtgggg gacaacgttt      60
cgaaaggaac gctaataccg catacgtcct acgggagaaa gcagggacc ttcgggcctt     120 gcgctatcag atgagcctag gtcggattag ctagttggtg aggtaatggc tcaccaaggc    180
gacgatccgt aactggtctg agaggatgat cagtcacact ggaactgaga cacggtccag    240
actcctacgg gaggcagcag tggggaatat tggacaatgg gcgaaagcct gatccagcca    300
tgccgcgtgt gtgaagaagg tcttcggatt gtaaagcact ttaagttggg aggaagggtt    360
gtagattaat actctgcaat tttgacgtta ccgacagaat aagcaccggc taactctgtg    420
ccagcagccg cggtaataca gagggtgcaa gcgttaatcg gaattactgg gcgtaaagcg    480
cgcgtaggtg gttcgttaag ttggatgtga atccccggg ctcaacctgg gaactgcatc    540
caaaactggc gagctagagt atggtagagg gtggtggaat ttcctgtgta gcggtgaaat    600
gcgtagatat aggaaggaac accagtggcg aaggcgacca cctggactga tactgacact    660
gaggtgcgaa agcgtgggga gcaaacagga ttagataccc tggtagtcca cgccgtaaac    720
gatgtcaact agccgttggg agccttgagc tcttagtggc gcagctaacg cattaagttg    780
accgcctggg gagtacggcc gcaaggttaa aactcaaatg aattgacggg ggcccgcaca    840
agcggtggag catgtggttt aattcgaagc aacgcgaaga accttaccag gccttgacat    900
```

```
ccaatgaact ttccagagat ggattggtgc cttcgggaac attgagacag gtgctgcatg    960
gctgtcgtca gctcgtgtcg tgagatgttg ggttaagtcc cgtaacgagc gcaacccttg   1020
tccttagtta ccagcacgtt atggtgggca ctctaaggag actgccggtg acaaaccgga   1080
ggaaggtggg gatgacgtca agtcatcatg gcccttacgg cctgggctac acacgtgcta   1140
caatggtcgg tacagagggt tgccaagccg cgaggtggag ctaatcccac aaaaccgatc   1200
gtagtccgga tcgcagtctg caactcgact gcgtgaagtc ggaatcgcta gtaatcgcga   1260
atcagaatgt cgcggtgaat acgttcccgg gccttgtaca caccgcccgt cacaccatgg   1320
gagtgggtt                                                           1329
```

PSEUDOMONAS ISOLATES AND USES THEREOF

CROSS-REFERENCE TO RELATED APPLICATIONS

This application is a 35 U.S.C. 371 national application of international application no. PCT/US2020/060968, filed Nov. 18, 2020, which claims priority to or the benefit under 35 U.S.C. 119 of U.S. provisional application No. 62/937,929, filed Nov. 20, 2019, the contents of which are fully incorporated herein by reference.

REFERENCE TO A SEQUENCE LISTING

This application contains a Sequence Listing in computer readable form, which is incorporated herein by reference.

REFERENCE TO DEPOSIT OF BIOLOGICAL MATERIALS

The present disclosure contains references to biological materials deposited under the terms of the Budapest Treaty on the International Recognition of the Deposit of Microorganisms for the Purposes of Patent Procedure at the Agricultural Research Service Culture Collection, 1815 North University Street, Peoria, Illinois 61604, U.S.A.

BACKGROUND

Inoculant compositions comprising agriculturally beneficial microorganisms are well known in the art. See, e.g., U.S. Pat. Nos. 5,484,464; 5,586,411; 5,695,541; 5,804,208; 5,916,029; 6,569,425; 6,808,917; 6,824,772; 7,429,477; 8,148,138; 8,278,247; 8,445,256; 8,883,679; 8,921,089; 8,999,698; 9,017,442; 9,101,088; 9,234,251; 9,340,464.

Nevertheless, because of burgeoning populations and increasing demands for more efficient and productive farms, there remains a need for new compositions and methods for enhancing crop yield.

SUMMARY OF THE CLAIMED INVENTION

The present disclosure provides isolated microbial strains capable of enhancing various aspects of plant growth and crop yield, as well as compositions comprising the isolated strains and methods of using the isolated strains.

A first aspect of the present disclosure is the isolated strain of *Pseudomonas koreensis* having the deposit accession number NRRL B-67602 (*P. koreensis* NRRL B-67883).

A second aspect of the present disclosure is a biologically pure culture of *P. koreensis* NRRL B-67883.

A third aspect of the present disclosure is use of a *Pseudomonas koreensis*, such as *P. koreensis* NRRL B-67883, for enhancing plant growth and/or yield.

A fourth aspect of the present disclosure is use of a *Pseudomonas koreensis*, such as *P. koreensis* NRRL B-67883, for enhancing chlorophyll production and/or accumulation and/or content in a plant or plant part.

A fifth aspect of the present disclosure is use of a *Pseudomonas koreensis*, such as *P. koreensis* NRRL B-67883, for enhancing nutrient uptake and/or accumulation and/or content, optionally calcium, copper, iron, manganese, mangenisum, nitrogen, potassium, phosphorous and/or zinc uptake and/or accumulation and/or content, in a plant or plant part.

A sixth aspect of the present disclosure is a method of introducing a *Pseudomonas koreensis*, such as *P. koreensis* NRRL B-67883, into a plant growth medium in an effective amount and/or concentration for enhancing the growth and/or yield of a plant grown therein.

A seventh aspect of the present disclosure is a method of applying a *Pseudomonas koreensis*, such as *P. koreensis* NRRL B-67883, to a plant propagation material, optionally a seed, in an effective amount and/or concentration for enhancing the growth and/or yield of a plant grown therefrom.

An eighth aspect of the present disclosure is a method of applying a *Pseudomonas koreensis*, such as *P. koreensis* NRRL B-67883, to a plant in an effective amount and/or concentration for enhancing the growth and/or yield thereof.

A ninth aspect of the present disclosure is an inoculant composition comprising a *Pseudomonas koreensis*, such as *P. koreensis* NRRL B-67883, in an agriculturally acceptable carrier. In some embodiments, the inoculant composition comprises one or more additional microorganisms.

A tenth aspect of the present disclosure is a non-naturally occurring seed composition comprising a plant propagation material, such as a seed, that is at least partially coated with an inoculant composition comprising a *Pseudomonas koreensis*, such as *P. koreensis* NRRL B-67883.

An eleventh aspect of the present disclosure is a non-naturally occurring seed composition comprising *Pseudomonas koreensis*, such as *P. koreensis* NRRL B-67883, into a plant growth medium, such as a soil.

A twelfth aspect of the present disclosure is a synthetic microbial consortium comprising *P. koreensis* NRRL B-67883 and at least one additional microorganism.

A thirteenth aspect of the present disclosure is use of a synthetic microbial consortium comprising *P. koreensis* NRRL B-67883 and at least one additional microorganism for enhancing plant growth and/or yield.

DETAILED DESCRIPTION

This description is not intended to be a detailed catalog of all the different ways in which the invention may be implemented or of all the features that may be added to the instant invention. For example, features illustrated with respect to one embodiment may be incorporated into other embodiments and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following description is intended to illustrate some particular embodiments of the invention and not to exhaustively specify all permutations, combinations and variations thereof.

The terminology used herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. For the sake of brevity and/or clarity, well-known functions or constructions may not be described in detail.

As used herein, the singular forms "a," "an," and "the" are intended to include the plural forms as well, unless the context clearly indicates otherwise.

As used herein, the terms "acaricide" and "acaricidal" refer to an agent or combination of agents the application of which is toxic to an acarid (i.e., kills an acarid, inhibits the growth of an acarid and/or inhibits the reproduction of an acarid).

As used herein, the term "agriculturally beneficial agent" refers to any agent (e.g., chemical or biological agent) or combination of agents the application of which causes or provides a beneficial and/or useful effect in agriculture including, but not limited to, agriculturally beneficial microorganisms, biostimulants, nutrients, pesticides (e.g., acaricides, fungicides, herbicides, insecticides, and nematicides) and plant signal molecules.

As used herein, the term "agriculturally beneficial microorganism" refers to a microorganism having at least one agriculturally beneficial property (e.g., the ability to fix nitrogen, the ability to solubilize phosphate and/or the ability to produce an agriculturally beneficial agent, such as a plant signal molecule).

As used herein, the term "agriculturally acceptable carrier" refers to a substance or composition that can be used to deliver an agriculturally beneficial agent to a plant, plant part or plant growth medium (e.g., soil) without causing/having an unduly adverse effect on plant growth and/or yield. As used herein, the tem "foliar-compatible carrier" refers to a material that can be foliarly applied to a plant or plant part without causing/having an unduly adverse effect on the plant, plant part, plant growth, plant health, or the like. As used herein, the term "seed-compatible carrier" refers to a material that can be applied to a seed without causing/having an unduly adverse effect on the seed, the plant that grows from the seed, seed germination, or the like. As used herein, the term "soil-compatible carrier" refers to a material that can be added to a soil without causing/having an unduly adverse effect on plant growth, soil structure, soil drainage, or the like.

As used herein, the term "and/or" is intended to include any and all combinations of one or more of the associated listed items, as well as the lack of combinations when interpreted in the alternative ("or"). Thus, the phrase "A, B and/or C" is to be interpreted as "A, A and B, A and B and C, A and C, B, B and C, or C."

As used herein, the terms "associated with," in association with" and "associated therewith," when used in reference to a relationship between a microbial strain or inoculant composition of the present disclosure and a plant or plant part, refer to at least a juxtaposition or close proximity of the microbial strain or inoculant composition and the plant or plant part. Such a juxtaposition or close proximity may be achieved by contacting or applying the microbial strain or inoculant composition directly to the plant or plant part and/or by applying the microbial strain or inoculant composition to the plant growth medium (e.g., soil) in which the plant or plant part will be grown (or is currently being grown). According to some embodiments, the microbial strain or inoculant composition is applied as a coating to the outer surface of the plant or plant part. According to some embodiments, the microbial strain or inoculant composition is applied to soil at, near or surrounding the site in which the plant or plant part will be grown (or is currently being grown).

As used herein, the term "aqueous" refers to a composition that contains more than a trace amount of water (i.e., more than 0.5% water by weight, based upon the total weight of the composition).

As used herein, the term "biologically pure culture" refers to a microbial culture that is free or essentially free of biological contamination and that has genetic uniformity such that different subculutres taken therefrom will exhibit identical or substantially identical genotypes and phenotypes. In some embodiments, the biologically pure culture is 100% pure (i.e., all subcultures taken therefrom exhibit identical genotypes and phenotypes). In some embodiments, the biologically pure culture is at least 90, 91, 92, 93, 94, 95, 96, 97, 98, 99, 99.5, 99.6, 99.7, 99.8, or 99.9% pure (i.e., at least 90, 91, 92, 93, 94, 95, 96, 97, 98, 99, 99.5, 99.6, 99.7, 99.8, or 99.9% of the subcultures taken therefrom exhibit identical genotypes and phenotypes).

As used herein, the term "biostimulant" refers to an agent or combination of agents the application of which enhances one or more metabolic and/or physiological processes of a plant or plant part (e.g., carbohydrate biosynthesis, ion uptake, nucleic acid uptake, nutrient delivery, photosynthesis and/or respiration).

As used herein, the term "BRADY" is to be interpreted as a shorthand substitute for the phrase "*Bradyrhizobium* spp. 8A57, *Bradyrhizobium elkanii* SEMIA 501, *Bradyrhizobium elkanii* SEMIA 587, *Bradyrhizobium elkanii* SEMIA 5019, *Bradyrhizobium japonicum* 61A227, *Bradyrhizobium japonicum* 61A228, *Bradyrhizobium japonicum* 61A273, *Bradyrhizobium japonicum* E-109, *Bradyrhizobium japonicum* NRRL B-50586 (also deposited as NRRL B-59565), *Bradyrhizobium japonicum* NRRL B-50587 (also deposited as NRRL B-59566), *Bradyrhizobium japonicum* NRRL B-50588 (also deposited as NRRL B-59567), *Bradyrhizobium japonicum* NRRL B-50589 (also deposited as NRRL B-59568), *Bradyrhizobium japonicum* NRRL B-50590 (also deposited as NRRL B-59569), *Bradyrhizobium japonicum* NRRL B-50591 (also deposited as NRRL B-59570), *Bradyrhizobium japonicum* NRRL B-50592 (also deposited as NRRL B-59571), *Bradyrhizobium japonicum* NRRL B-50593 (also deposited as NRRL B-59572), *Bradyrhizobium japonicum* NRRL B-50594 (also deposited as NRRL B-50493), *Bradyrhizobium japonicum* NRRL B-50608, *Bradyrhizobium japonicum* NRRL B-50609, *Bradyrhizobium japonicum* NRRL B-50610, *Bradyrhizobium japonicum* NRRL B-50611, *Bradyrhizobium japonicum* NRRL B-50612, *Bradyrhizobium japonicum* NRRL B-50726, *Bradyrhizobium japonicum* NRRL B-50727, *Bradyrhizobium japonicum* NRRL B-50728, *Bradyrhizobium japonicum* NRRL B-50729, *Bradyrhizobium japonicum* NRRL B-50730, *Bradyrhizobium japonicum* SEMIA 566, *Bradyrhizobium japonicum* SEMIA 5079, *Bradyrhizobium japonicum* SEMIA 5080, *Bradyrhizobium japonicum* USDA 6, *Bradyrhizobium japonicum* USDA 110, *Bradyrhizobium japonicum* USDA 122, *Bradyrhizobium japonicum* USDA 123, *Bradyrhizobium japonicum* USDA 127, *Bradyrhizobium japonicum* USDA 129 and/or *Bradyrhizobium japonicum* USDA 532C."

As used herein, the terms "colony forming unit" and "cfu" refer to a microbial cell/spore capable of propagating on or in a suitable growth medium or substrate (e.g., a soil) when conditions (e.g., temperature, moisture, nutrient availability, pH, etc.) are favorable for germination and/or microbial growth.

As used herein, the term "consists essentially of,", when used in reference to inoculant compositions and methods of the present disclosure, means that the compositions/methods may contain additional components/steps so long as the additional components/steps do not materially alter the composition/method. The term "materially alter," as applied to a composition/method of the present disclosure, refers to an increase or decrease in the effectiveness of the composition/method of at least 20%. For example, a component added to an inoculant composition of the present disclosure may be deemed to "materially alter" the composition if it increases or decreases the composition's ability to enhance plant yield by at least 20%.

As used herein, the term "diazotroph" refers to an organism capable of converting atmospheric nitrogen ($N_2$) into a form that may be utilized by a plant or plant part (e.g., ammonia ($NH_3$), ammonium ($NH_4+$), etc.).

As used herein, the term "dispersant" refers to an agent or combination of agents the application of which reduces the cohesiveness of like particles, the surface tension of a liquid, the interfacial tension between two liquids and/or the interfacial tension between or a liquid and a solid.

As used herein, the terms "effective amount," "effective concentration" and "effective amount/concentration" refer to an amount or concentration that is sufficient to cause a desired effect (e.g. enhanced crop yield). The absolute value of the amount/concentration that is sufficient to cause the desired effect may be affected by factors such as the type and magnitude of effect desired, the type, size and volume of material to which the inoculant composition will be applied, the type(s) of microorganisms in the composition, the number of microorganisms in the composition, the stability of the microorganism(s) in the inoculant composition and the storage conditions (e.g., temperature, relative humidity, duration). Those skilled in the art will understand how to select an effective amount/concentration using routine dose-response experiments.

As used herein, the term "enhanced dispersion" refers to an improvement in one or more characteristics of microbial dispersion as compared to one or more controls (e.g., a control composition that is identical to an inoculant composition of the present disclosure except that it lacks one or more of the components found in the inoculant composition of the present disclosure). Exemplary microbial dispersion characteristics include, but are not limited to, the percentage of microbes that exist as single cells/spores when the inoculant composition is diluted in water. An inoculant composition that improves one or more microbial dispersion characteristics of the microorganism(s) contained therein as compared to a control composition (e.g., a control composition that is identical to the inoculant composition except that it lacks one or more of the components found in the inoculant composition) provides enhanced dispersion and can be referred to as a "readily dispersable inoculant composition."

As used herein, the terms "enhanced growth" and "enhanced plant growth" refer to an improvement in one or more characteristics of plant growth and/or development as compared to one or more control plants (e.g., a plant germinated from an untreated seed or an untreated plant). Exemplary plant growth/development characteristics include, but are not limited to, biomass, carbohydrate biosynthesis, chlorophyll content, cold tolerance, drought tolerance, height, leaf canopy, leaf length, leaf mass, leaf number, leaf surface area, leaf volume, lodging resistance, nutrient uptake and/or accumulation (e.g., ammonium, boron, calcium, copper, iron, magnesium, manganese, nitrate, nitrogen, phosphate, phosphorous, potassium, sodium, sulfur and/or zinc uptake/accumulation), rate(s) of photosynthesis, root area, root diameter, root length, root mass, root nodulation (e.g., nodule mass, nodule number, nodule volume), root number, root surface area, root volume, salt tolerance, seed germination, seedling emergence, shoot diameter, shoot length, shoot mass, shoot number, shoot surface area, shoot volume, spread, stand, stomatal conductance and survival rate. Unless otherwise indicated, references to enhanced plant growth are to be interpreted as meaning that microbial strains, inoculant compositions and methods of the present disclosure enhance plant growth by enhancing nutrient availability, improving soil characteristics, etc. and are not to be interpreted as suggesting that microbial strains, inoculant compositions and methods of the present disclosure act as plant growth regulators.

As used herein, the terms "enhanced stability" and "enhanced microbial stability" refer to an improvement in one or more characteristics of microbial stability as compared to one or more controls (e.g., a control composition that is identical to an inoculant composition of the present disclosure except that it lacks one or more of the components found in the inoculant composition of the present disclosure). Exemplary microbial stability characteristics include, but are not limited to, the ability to germinate and/or propagate after being coated on a seed and/or stored for a defined period of time and the ability to cause a desired effect (e.g., enhanced plant yield and/or increased pesticidal activity) after being coated on a seed and/or stored for a defined period of time. A microorganism that exhibits improvement in one or more microbial stability characteristics as compared to a control microorganism when each is subjected to the same conditions (e.g., seed coating and storage conditions) displays enhanced stability and can be referred to as a "stable microorganism." An inoculant composition that improves one or more microbial stability characteristics of the microorganism(s) contained therein as compared to a control composition (e.g., a control composition that is identical to the inoculant composition except that it lacks one or more of the components found in the inoculant composition) provides enhanced stability and can be referred to as a "stable inoculant composition."

As used herein, the terms "enhanced survival" and "enhanced microbial survival" refer to an improvement in the survival rate of one or more microorganisms in an inoculant composition as compared to one or more microorganisms in a control composition (e.g., a control composition that is identical to an inoculant composition of the present disclosure except that it lacks one or more of the components found in the inoculant composition of the present disclosure). An inoculant composition that improves the survival rate of one or more of the microorganisms contained therein as compared to a control composition (e.g., a control composition that is identical to the inoculant composition except that it lacks one or more of the components found in the inoculant composition) provides enhanced survival and can be referred to as a stable inoculant composition.

As used herein, the terms "enhanced yield" and "enhanced plant yield" refer to an improvement in one or more characteristics of plant yield as compared to one or more control plants (e.g., a control plant germinated from an untreated seed). Exemplary plant yield characteristics include, but are not limited to, biomass; bushels per acre; grain weight per plot (GWTPP); nutritional content; percentage of plants in a given area (e.g., plot) that fail to produce grain; yield at standard moisture percentage (YSMP), such as grain yield at standard moisture percentage (GYSMP); yield per plot (YPP), such as grain weight per plot (GWTPP); and yield reduction (YRED). Unless otherwise indicated, references to enhanced plant yield are to be interpreted as meaning that microbial strains, inoculant compositions and methods of the present disclosure enhance plant yield by enhancing nutrient availability, improving soil characteristics, etc. and are not to be interpreted as suggesting that microbial strains, inoculant compositions and methods of the present disclosure act as plant growth regulators.

As used herein, the term "foliage" refers to those portions of a plant that normally grow above the ground, including, but not limited to, leaves, stalks, stems, flowers, fruiting bodies and fruits.

As used herein, the terms "foliar application" and "foliarly applied" refer to the application of one or more active ingredients to the foliage of a plant (e.g., to the leaves of the plant). Application may be effected by any suitable means, including, but not limited to, spraying the plant with a composition comprising the active ingredient(s). In some embodiments, the active ingredient(s) is/are applied to the leaves, stems and/or stalk of the plant and not to the flowers, fruiting bodies or fruits of the plant.

As used herein, the terms "fungicide" and "fungicidal" refer to an agent or combination of agents the application of which is toxic to a fungus (i.e., kills a fungus, inhibits the growth of a fungus and/or inhibits the reproduction of a fungus).

As used herein, the term "fulvic acid" encompasses pure fulvic acids and fulvic acid salts (fulvates). Non-limiting examples of fulvic acids include ammonium fulvate, boron fulvate, potassium fulvate, sodium fulvate, etc. In some embodiments, the fulvic acid comprises, consists essentially of or consists MDL Number MFCD09838488 (CAS Number 479-66-3).

As used herein, the terms "herbicide" and "herbicidal" refer to an agent or combination of agents the application of which is toxic to a weed (i.e., kills a weed, inhibits the growth of a weed and/or inhibits the reproduction of a weed).

As used herein, the term "humic acid" encompasses pure humic acids and humic acid salts (humates). Non-limiting examples of humic acids include ammonium humate, boron humate, potassium humate, sodium humate, etc. In some embodiments, the humic acid comprises, consists essentially of or consists of one or more of MDL Number MFCD00147177 (CAS Number 1415-93-6), MDL Number MFCD00135560 (CAS Number 68131-04-4), MDL Number MFCS22495372 (CAS Number 68514-28-3), CAS Number 93924-35-7 and CAS Number 308067-45-0.

As used herein, the terms "inoculant composition" and "inoculum" refer to a composition comprising microbial cells and/or spores, said cells/spores being capable of propagating/germinating on or in a suitable growth medium or substrate (e.g., a soil) when conditions (e.g., temperature, moisture, nutrient availability, pH, etc.) are favorable for germination and/or microbial growth.

As used herein, the terms "insecticide" and "insecticidal" refer to an agent or combination of agents the application of which is toxic to an insect (i.e., kills an insect, inhibits the growth of an insect and/or inhibits the reproduction of an insect).

As used herein, the term "isolated microbial strain" refers to a microbe that has been removed from the environment in which it is normally found.

As used herein, the term "isomer" includes all stereoisomers of the compounds and/or molecules to which it refers, including enantiomers and diastereomers, as well as all conformers, roatmers and tautomers, unless otherwise indicated. Compounds and/or molecules disclosed herein include all enantiomers in either substantially pure levorotatory or dextrorotatory form, or in a racemic mixture, or in any ratio of enantiomers. Where embodiments disclose a (D)-enantiomer, that embodiment also includes the (L)-enantiomer; where embodiments disclose a (L)-enantiomer, that embodiment also includes the (D)-enantiomer. Where embodiments disclose a (+)-enantiomer, that embodiment also includes the (−)-enantiomer; where embodiments disclose a (−)-enantiomer, that embodiment also includes the (+)-enantiomer. Where embodiments disclose a (S)-enantiomer, that embodiment also includes the (R)-enantiomer; where embodiments disclose a (R)-enantiomer, that embodiment also includes the (S)-enantiomer. Embodiments are intended to include any diastereomers of the compounds and/or molecules referred to herein in diastereomerically pure form and in the form of mixtures in all ratios. Unless stereochemistry is explicitly indicated in a chemical structure or chemical name, the chemical structure or chemical name is intended to embrace all possible stereoisomers, conformers, rotamers and tautomers of compounds and/or molecules depicted.

As used herein, the term "modified microbial strain" refers to a microbial strain that is modified from a strain isolated from nature. Modified microbial strains may be produced by any suitable method(s), including, but not limited to, chemical or other form of induced mutation to a polynucleotide within any genome within the strain; the insertion or deletion of one or more nucleotides within any genome within the strain, or combinations thereof; an inversion of at least one segment of DNA within any genome within the strain; a rearrangement of any genome within the strain; generalized or specific transduction of homozygous or heterozygous polynucleotide segments into any genome within the strain; introduction of one or more phage into any genome of the strain; transformation of any strain resulting in the introduction into the strain of stably replicating autonomous extrachromosomal DNA; any change to any genome or to the total DNA composition within the strain isolated from nature as a result of conjugation with any different microbial strain; and any combination of the foregoing. The term modified microbial strains includes a strain with (a) one of more heterologous nucleotide sequences, (b) one or more non-naturally occurring copies of a nucleotide sequence isolated from nature (i.e., additional copies of a gene that naturally occurs in the microbial strain from which the modified microbial strain was derived), (c) a lack of one or more nucleotide sequences that would otherwise be present in the natural reference strain by for example deleting nucleotide sequence, and (d) added extrachromosomal DNA. In some embodiments, modified microbial strains comprise a combination of two or more nucleotide sequences (e.g., two or more naturally occurring genes that do not naturally occur in the same microbial strain) or comprise a nucleotide sequence isolated from nature at a locus that is different from the natural locus.

As used herein, the terms "nematicide" and "nematicidal" refer to an agent or combination of agents the application of which is toxic to a nematode (i.e., kills a nematode, inhibits the growth of a nematode and/or inhibits the reproduction of a nematode).

As used herein, the term "nitrogen fixing organism" refers to an organism capable of converting atmospheric nitrogen ($N_2$) into a form that may be utilized by a plant or plant part (e.g., ammonia ($NH_3$), ammonium ($NH_4^+$), etc.).

As used herein, the term "non-aqueous" refers to a composition that comprises no more than a trace amount of water (i.e., no more than 0.5% water by weight, based upon the total weight of the composition).

As used herein, the term "nutrient" refers to a compound or element useful for nourishing a plant (e.g., vitamins, macrominerals, micronutrients, trace minerals, organic acids, etc. that are necessary for plant growth and/or development).

As used herein, the term "PENI" is to be interpreted as a shorthand substitute for the phrase "*Penicillium bilaiae* ATCC 18309, *Penicillium bilaiae* ATCC 20851, *Penicillium bilaiae* ATCC 22348, *Penicillium bilaiae* NRRL 50162, *Penicillium bilaiae* NRRL 50169, *Penicillium bilaiae* NRRL 50776, *Penicillium bilaiae* NRRL 50777, *Penicillium bilaiae* NRRL 50778, *Penicillium bilaiae* NRRL 50777, *Penicillium bilaiae* NRRL 50778, *Penicillium bilaiae* NRRL 50779, *Penicillium bilaiae* NRRL 50780, *Penicillium bilaiae* NRRL 50781, *Penicillium bilaiae* NRRL 50782, *Penicillium bilaiae* NRRL 50783, *Penicillium bilaiae* NRRL 50784, *Penicillium bilaiae* NRRL 50785, *Penicillium bilaiae* NRRL 50786, *Penicillium bilaiae* NRRL 50787, *Penicillium bilaiae* NRRL 50788, *Penicillium bilaiae* RS7B-SD1, *Penicillium brevicompactum* AgRF18, *Penicillium canescens* ATCC 10419, *Penicillium expansum* ATCC 24692, *Penicillium expansum* YT02, *Penicillium fellatanum* ATCC 48694, *Penicillium gaestrivorus* NRRL 50170, *Penicillium glabrum* DAOM 239074, *Penicillium glabrum* CBS 229.28, *Penicillium janthinellum* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* N93/47267 and/or *Penicillium raistrickii* ATCC 10490."

As used herein, the term "*Penicillium bilaiae*" is intended to include all iterations of the species name, such as "*Penicillium bilaji*" and "*Penicillium bilaii.*"

As used herein, the terms "percent identity," "% identity" and "percent identical" refer to the relatedness of two or more nucleotide or amino acid sequences, which may be calculated by (i) comparing two optimally aligned sequences over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present invention, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

As used herein, the term "pest" includes any organism or virus that negatively affects a plant, including, but not limited to, organisms and viruses that spread disease, damage host plants and/or compete for soil nutrients. The term "pest" encompasses organisms and viruses that are known to associate with plants and to cause a detrimental effect on the plant's health and/or vigor. Plant pests include, but are not limited to, arachnids (e.g., mites, ticks, spiders, etc.), bacteria, fungi, gastropods (e.g., slugs, snails, etc.), invasive plants (e.g., weeds), insects (e.g., white flies, *thrips*, weevils, etc.), nematodes (e.g., root-knot nematode, soybean cyst nematode, etc.), rodents and viruses (e.g., tobacco mosaic virus (TMV), tomato spotted wilt virus (TSWV), cauliflower mosaic virus (CaMV), etc.).

As used herein, the terms "pesticide" and "pesticidal" refer to agents or combinations of agents the application of which is toxic to a pest (i.e., kills a pest, inhibits the growth of a pest and/or inhibits the reproduction of a pest). Non-limiting examples of pesticides include acaricides, fungicides, herbicides, insecticides, and nematicides, etc.

As used herein, the term "phosphate-solubilizing microorganism" refers to a microorganism capable of converting insoluble phosphate into a soluble form of phosphate.

As used herein, the term "plant" includes all plant populations, including, but not limited to, agricultural, horticultural and silvicultural plants. The term "plant" encompasses plants obtained by conventional plant breeding and optimization methods (e.g., marker-assisted selection) and plants obtained by genetic engineering, including cultivars protectable and not protectable by plant breeders' rights.

As used herein, the term "plant cell" refers to a cell of an intact plant, a cell taken from a plant, or a cell derived from a cell taken from a plant. Thus, the term "plant cell" includes cells within seeds, suspension cultures, embryos, meristematic regions, callus tissue, leaves, shoots, gametophytes, sporophytes, pollen and microspores.

As used herein, the term "plant growth regulator" refers to an agent or combination of agents the application of which accelerates or retards the growth/maturation rate of a plant through direct physiological action on the plant or which otherwise alters the behavior of a plant through direct physiological action on the plant. "Plant growth regulator" shall not be interpreted to include any agent or combination of agents excluded from the definition of "plant regulator" that is set forth section 2(v) of the Federal Insecticide, Fungicide, and Rodenticide Act (7 U.S.C. § 136(v)). Thus, "plant growth regulator" does not encompass microorganisms applied to a plant, plant part or plant growth medium for the purpose of enhancing the availability and/or uptake of nutrients, nutrients necessary to normal plant growth, soil amendments applied for the purpose of improving soil characteristics favorable for plant growth or vitamin hormone products as defined by 40 C.F.R. § 152.6(f).

As used herein, the term "plant part" refers to any part of a plant, including cells and tissues derived from plants. Thus, the term "plant part" may refer to any of plant components or organs (e.g., leaves, stems, roots, etc.), plant tissues, plant cells and seeds. Examples of plant parts, include, but are not limited to, anthers, embryos, flowers, fruits, fruiting bodies, leaves, ovules, pollen, rhizomes, roots, seeds, shoots, stems and tubers, as well as scions, rootstocks, protoplasts, calli and the like.

As used herein, the term "plant propagation material" refers to a plant part from which a whole plant can be generated. Examples of plant propagation materials include, but are not limited to, cuttings (e.g., leaves, stems), rhizomes, seeds, tubers and cells/tissues that can be cultured into a whole plant.

As used herein, the term "progeny" refers to the descendent(s) of a given strain or pair of strains and encompasses both immediate offspring of said strain(s) and any descendants thereof.

As used herein, the terms "spore" and "microbial spore" refer to a microorganism in its dormant, protected state.

As used herein, the term "stabilizing compound" refers to an agent or combination of agents the application of which enhances the survival and/or stability of a microorganism in an inoculant composition.

As used herein with respect to inoculant compositions, the term "stable" refers to an inoculant composition in which microorganisms exhibit enhanced stability and/or enhanced survival. In general, an inoculant composition may be labeled "stable" if it improves the survival rate and/or at least one microbial stability characteristic of at least one microorganism contained therein.

As used herein, the term "strains of the present disclosure" encompasses *P. koreensis* NRRL B-67883, progeny of *P. koreensis* NRRL B-67883, modified microbial strains derived from *P. koreensis* NRRL B-67883, modified microbial strains derived from progeny of *P. koreensis* NRRL B-67883, and other close relatives and variants of *P. koreensis* NRRL B-67883. Progeny may be produced using any suitable method(s), including, but not limited to, protoplast fusion, traditional breeding programs and combinations thereof. Modified microbial strains may be produced using suitable method(s), including, but not limited to, chemically-induced mutation of a polynucleotide within any genome within one of the aforementioned strains; the insertion or deletion of one or more nucleotides within any genome within one of the aforementioned strains, or combinations thereof; an inversion of at least one segment of DNA within any genome within one of the aforementioned strains; a rearrangement of any genome within one of the aforementioned strains; generalized or specific transduction of homozygous or heterozygous polynucleotide segments into any genome within one of the aforementioned strains; introduction of one or more phage into any genome of one of the aforementioned strains; transformation of one of the aforementioned strains resulting in the introduction into one of the aforementioned strains of stably replicating autonomous extrachromosomal DNA; any change to any genome or to the total DNA composition within one of the aforementioned strains as a result of conjugation with any different microbial strain; and any combination of the foregoing.

As used herein with respect to microbial strains, the term "survival rate" refers to the percentage of microbial cell/spore that are viable (i.e., capable of propagating on or in a suitable growth medium or substrate (e.g., a soil) when conditions (e.g., temperature, moisture, nutrient availability, pH, etc.) are favorable for germination and/or microbial growth) at a given period of time.

While certain aspects of the present disclosure will hereinafter be described with reference to embodiments thereof, it will be understood by those of ordinary skill in the art that various changes in form and details may be made therein without departing from the spirit and scope of the present disclosure as defined by the claims.

All publications, patent applications, patents and other references mentioned herein are incorporated by reference in their entirety, except insofar as they contradict any disclosure expressly set forth herein.

The present disclosure provides an isolated *Pseudomonas koreensis* strain having the deposit accession number NRRL B-67883 (*P. koreensis* NRRL B-67883), as well as progeny of *P. koreensis* NRRL B-67883, modified microbial strains derived from *P. koreensis* NRRL B-67883, modified microbial strains derived from progeny of *P. koreensis* NRRL B-67883, and other close relatives of *P. koreensis* NRRL B-67883.

The present disclosure also provides cultures comprising, consisting essentially of or consisting of one or more strains of the present disclosure. In some embodiments, at least 95, 95.5, 95.55, 95.6, 95.65, 95.7, 95.75, 95.8, 95.85, 95.9, 95.95, 96, 96.05, 96.1, 96.15, 96.2, 96.25, 96.3, 96.35, 96.4, 96.45, 96.5, 96.55, 96.6, 96.65, 96.7, 96.75, 96.8, 96.85, 96.9, 96.95, 97, 97.5, 97.55, 97.6, 97.65, 97.7, 97.75, 97.8, 97.85, 97.9, 97.95, 98, 98.05, 98.1, 98.15, 98.2, 98.25, 98.3, 98.35, 98.4, 98.45, 98.5, 98.55, 98.6, 98.65, 98.7, 98.75, 98.8, 98.85, 98.9, 98.95, 99, 99.05, 99.1, 99.15, 99.2, 99.25, 99.3, 99.35, 99.4, 99.45, 99.5, 99.55, 99.6, 99.65, 99.7, 99.75, 99.8, 99.85, 99.9, 99.91, 99.92, 99.93, 99.94, 99.95, 99.96, 99.97, 99.98, 99.99 or 100% of subcultures taken from the culture exhibit a genotype that is at least 95, 95.5, 95.55, 95.6, 95.65, 95.7, 95.75, 95.8, 95.85, 95.9, 95.95, 96, 96.05, 96.1, 96.15, 96.2, 96.25, 96.3, 96.35, 96.4, 96.45, 96.5, 96.55, 96.6, 96.65, 96.7, 96.75, 96.8, 96.85, 96.9, 96.95, 97, 97.5, 97.55, 97.6, 97.65, 97.7, 97.75, 97.8, 97.85, 97.9, 97.95, 98, 98.05, 98.1, 98.15, 98.2, 98.25, 98.3, 98.35, 98.4, 98.45, 98.5, 98.55, 98.6, 98.65, 98.7, 98.75, 98.8, 98.85, 98.9, 98.95, 99, 99.05, 99.1, 99.15, 99.2, 99.25, 99.3, 99.35, 99.4, 99.45, 99.5, 99.55, 99.6, 99.65, 99.7, 99.75, 99.8, 99.85, 99.9, 99.91, 99.92, 99.93, 99.94, 99.95, 99.96, 99.97, 99.98, 99.99 or 100% identical to that of *P. koreensis* NRRL B-67883. In some embodiments, the culture is a biologically pure culture of *P. koreensis* NRRL B-67883.

The present disclosure also provides inoculant compositions comprising, consisting essentially of or consisting of one or more strains of the present disclosure and a carrier.

Strains may be cultured using any suitable method(s), including, but not limited to, liquid-state fermentation and solid-state fermentation. See, generally, Cunningham et al., CAN. J. BOT. 68:2270 (1990); Friesen et al., APPL. MICROBIOL. BIOTECH. 68:397 (2005).

Strains may be harvested during any suitable growth phase. In some embodiments, strains are allowed to reach the stationary growth phase and then harvested.

Strains may be harvested and/or concentrated using any suitable method(s), including, but not limited to, centrifugation (e.g., density gradient centrifugation, disc stack centrifugation, tubular bowl centrifugation), coagulation, decanting, felt bed collection, filtration (e.g., drum filtration, sieving, ultrafiltration), flocculation, impaction and trapping (e.g., cyclone spore trapping, liquid impingement).

Strains may be formulated into any suitable type of composition, including, but not limited to, foliar inoculants, seed coatings and soil inoculants.

Strains may be incorporated into inoculant compositions in any suitable amount/concentration. The absolute value of the amount/concentration that is/are sufficient to cause the desired effect(s) may be affected by factors such as the type, size and volume of material to which the composition will be applied and storage conditions (e.g., temperature, relative humidity, duration). Those skilled in the art will understand how to select an effective amount/concentration using routine dose-response experiments.

In some embodiments, inoculant compositions of the present disclosure comprise one or more strains of the present disclosure in an amount ranging from about $1 \times 10^1$ to about $1 \times 10^{15}$ colony-forming units (cfu) per gram and/or milliliter of inoculant composition. For example, inoculant compositions of the present disclosure may comprise about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ or more cfu of *P. koreensis* NRRL B-67883 per gram and/or milliliter of inoculant composition. In some embodiments, inoculant compositions of the present disclosure comprise at least $1 \times 10^4$, $1 \times 10^5$, $1\times10^6$, $1\times10^7$, $1\times10^8$, $1\times10^9$, $1\times10^{10}$, $1\times10^{11}$, $1\times10^{12}$ cfu of *P. koreensis* NRRL B-67883 per gram and/or milliliter of inoculant composition.

In some embodiments, strains of the present disclosure comprise about 0.1 to about 95% (by weight) of the inoculant composition. For example, inoculant compositions of the present disclosure may comprise about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95% or more (by weight) of *P. koreensis* NRRL B-67883. In some embodiments, *P. koreensis* NRRL B-67883 comprise(s) about 1 to about 25%, about 5 to about 20%, about 5 to about 15%, about 5 to about 10% or about 8 to about 12% (by weight) of the inoculant composition.

In some embodiments, inoculant compositions of the present disclosure comprise one or more strains of the present disclosure in an effective amount/concentration for enhancing plant growth/yield when the inoculant composition is introduced into a plant growth medium (e.g., a soil).

In some embodiments, inoculant compositions of the present disclosure comprise one or more strains of the present disclosure in an effective amount/concentration for solubilizing potassium, phosphate and/or zinc when the inoculant composition is introduced into a plant growth medium (e.g., a soil).

In some embodiments, inoculant compositions of the present disclosure comprise one or more strains of the present disclosure in an effective amount/concentration for enhancing plant growth/yield when the inoculant composition is applied to a plant or plant part.

Inoculant compositions of the present disclosure may comprise any suitable carrier(s), including, but not limited to, foliar-compatible carriers, seed-compatible carriers and soil-compatible carriers. Selection of appropriate carrier materials will depend on the intended application(s) and the microorganism(s) present in the inoculant composition. In some embodiments, the carrier material(s) will be selected to provide an inoculant composition in the form of a liquid, gel, slurry, or solid. In some embodiments, the carrier will consist essentially of or consist of one or more stabilizing compounds.

In some embodiments, the inoculant composition comprises one or more solid carriers. According to some embodiments, the inoculant composition comprises one or more powders (e.g., wettable powders) and/or granules. Non-limiting examples of solid carriers include clays (e.g., attapulgite clays, montmorillonite clay, etc.), peat-based powders and granules, freeze-dried powders, spray-dried powders, spray-freeze-dried powders and combinations thereof.

In some embodiments, the inoculant composition comprises one or more liquid and/or gel carriers. According to some embodiments, the inoculant composition comprises one or more non-aqueous solvents. According to some embodiments, the inoculant composition comprises one or more aqueous solvents (e.g., water). According to some embodiments, an aqueous solvent, such as water, may be combined with a co-solvent, such as ethyl lactate, methyl soyate/ethyl lactate co-solvent blends (e.g., STEPOSOL™, Stepan), isopropanol, acetone, 1,2-propanediol, n-alkylpyrrolidones (e.g., AGSOLEX™ wetting agents; Ashland, Inc., Covington, KY), petroleum based-oils (e.g., AROMATIC™ and SOLVESSO™ fluids; ExxonMobil Chemical Company, Spring, TX), isoparrafinic hyydrocarbons (e.g., ISOPAR™ fluids; ExxonMobil Chemical Company, Spring, TX), cycloparaffinic hydrocarbons (e.g., NAPPAR™ 6; ExxonMobil Chemical Company, Spring, TX), mineral spirits (e.g., VARSOL™; ExxonMobil Chemical Company, Spring, TX), and mineral oils (e.g., paraffin oil). According to some embodiments, the inoculant composition comprises one or more inorganic solvents, such as decane, dodecane, hexylether and nonane. According to some embodiments, the inoculant composition comprises one or more organic solvents, such as acetone, dichloromethane, ethanol, hexane, methanol, propan-2-ol and trichloroethylene. Non-limiting examples of liquid/gel carriers include oils (e.g., mineral oil, olive oil, peanut oil, soybean oil, sunflower oil), polyethylene glycols (e.g., PEG 200, PEG 300, PEG 400, etc.), propylene glycols (e.g., PPG-9, PPG-10, PPG-17, PPG-20, PPG-26, etc.), ethoxylated alcohols (e.g., TOMADOL® (Air Products and Chemicals, Inc., Allentown, PA), TERGITOL™ 15-S surfactants such as TERGITOL™ 15-S-9 (The Dow Chemical Company, Midland, MI), etc.), isoparrafinic hyydrocarbons (e.g., ISOPAR™, ISOPAR™ L, ISOPAR™ M, ISOPAR™ V; ExxonMobil Chemical Company, Spring, TX), pentadecane, polysorbates (e.g. polysorbate 20, polysorbate 40, polysorbate 60, polysorbate 80, etc.), silicones (siloxanes, trisiloxanes, etc.) and combinations thereof. In some embodiments, the carrier comprises, consists essentially of or consists of dodecane. In some embodiments, the carrier comprises, consists essentially of or consists of methyl soyate. In some embodiments, the carrier comprises, consists essentially of or consists of one or more paraffin oils and/or waxes.

Additional examples of carriers may be found in BURGES, FORMULATION OF MICROBIAL BIOPESTICIDES: BENEFICIAL MICROORGANISMS, NEMATODES and SEED TREATMENTS (Springer Science & Business Media) (2012); Inoue & Horikoshi, J. FERMENTATION BIOENG. 71(3):194 (1991).

Inoculant compositions of the present disclosure may comprise any suitable stabilizing compound(s), including, but not limited to, maltodextrins, monosaccharides, disaccharides, oligosaccharides, sugar alcohols, humic acids, fulvic acids, malt extracts, peat extracts, betaines, prolines, sarcosines, peptones, skim milks, oxidation control components, hygroscopic polymers and UV protectants.

In some embodiments, the inoculant composition comprises one or more maltodextrins (e.g., one or more maltodextrins having a dextrose equivalent value (DEV) of about 3, 4, 5, 6, 7, 8, 9, 10, 11, 12, 13, 14, 15, 16, 17, 18, 19, 20, 21, 22, 23, 24, or 25). According to some embodiments, the inoculant composition comprises one or more maltodextrins having a DEV of about 5 to about 6, 7, 8, 9, 10, 11, 12, 14, 15, 16, 17, 18, 19 or 20, about 10 to about 11, 12, 14, 15, 16, 17, 18, 19 or 20, or about 15 to about 16, 17, 18, 19 or 20. According to some embodiments, the inoculant composition comprises a combination of maltodextrins having a DEV of about 5 to about 6, 7, 8, 9, 10, 11, 12, 14, 15, 16, 17, 18, 19 or 20, about 10 to about 11, 12, 14, 15, 16, 17, 18, 19 or 20, or about 15 to about 16, 17, 18, 19 or 20. Non-limiting examples of maltodextrins include MALTRIN® M040 (DEV=5; molecular weight=3600; Grain Processing Corporation, Muscatine, IA), MALTRIN® M100 (DEV=10; molecular weight=1800; Grain Processing Corporation, Muscatine, IA), MALTRIN® M150 (DEV=15; molecular weight=1200; Grain Processing Corporation, Muscatine, IA), MALTRIN® M180 (DEV=18; molecular weight=1050; Grain Processing Corporation, Muscatine, IA), MALTRIN® M200 (DEV=20; molecular weight=900; Grain Processing Corporation, Muscatine, IA), MALTRIN® M250 (DEV=25; molecular weight=720; Grain Processing Corporation, Muscatine, IA); MALTRIN QD® M580 (DEV=16.5-19.9; Grain Processing Corporation, Muscatine, IA); MALTRIN QD® M585 (DEV=15.0-19.9; Grain Processing Corporation, Muscatine, IA); MALTRIN QD® M600 (DEV=20.0-23.0; Grain Processing Corporation, Muscatine, IA); GLOBE® Plus 15 DE (Ingredion Inc., Westchester, IL); and combinations thereof.

In some embodiments, the inoculant composition comprises one or more monosaccharides (e.g., allose, altrose, arabinose, fructose, galactose, glucose, gulose, iodose, lyxose, mannose, ribose, talose, threose and/or xylose). According to some embodiments, the inoculant composition comprises gluscose. According to some embodiments, the inoculant composition does not comprise glucose.

In some embodiments, the inoculant composition comprises one or more disaccharides (e.g., cellobiose, chitobiose, gentiobiose, gentiobiulose, isomaltose, kojibiose, lactose, lactulose, laminaribiose, maltose (e.g., maltose monohydrate, anhydrous maltose), maltulose, mannobiose, melibiose, melibiulose, nigerose, palatinose, rutinose, rutinulose, sophorose, sucrose, trehalose, turanose and/or xylobiose). According to some embodiments, the inoculant composition comprises maltose. According to some embodiments, the inoculant composition does not comprise maltose. According to some embodiments, the inoculant composition comprises trehalose. According to some embodiments, the inoculant composition does not comprise trehalose.

In some embodiments, the inoculant composition comprises one or more oligosaccharides (e.g., fructo-oligosaccharides, galacto-oligosaccharides, mannon-oligosaccharides and/or raffinose).

In some embodiments, the inoculant composition comprises one or more sugar alcohols (e.g., arabitol, erythritol, fucitol, galactitol, glycerol, iditol, inositol, isomalt, lactitol, maltitol, maltotetraitol, maltotriitol, mannitol, polyglycitol, ribitol, sorbitol, threitol, volemitol and/or xylitol).

In some embodiments, the inoculant composition comprises one or more humic acids (e.g., one or more leonardite humic acids, lignite humic acids, peat humic acids and water-extracted humic acids). In some embodiments, the inoculant composition comprises ammonium humate, boron humate, potassium humate and/or sodium humate. In some embodiments, one or more of ammonium humate, boron humate, potassium humate and sodium humate is/are excluded from the inoculant composition. Nonlimiting examples of humic acids that may be useful in embodiments of the present disclosure include MDL Number MFCD00147177 (CAS Number 1415-93-6), MDL Number MFCD00135560 (CAS Number 68131-04-4), MDL Number MFCS22495372 (CAS Number 68514-28-3), CAS Number 93924-35-7, and CAS Number 308067-45-0.

In some embodiments, the inoculant composition comprises one or more fulvic acids (e.g., one or more leonardite fulvic acids, lignite fulvic acids, peat fulvic acids and/or water-extracted fulvic acids). In some embodiments, the inoculant composition comprises ammonium fulvate, boron fulvate, potassium fulvate and/or sodium fulvate. In some embodiments, one or more of ammonium fulvate, boron fulvate, potassium fulvate and sodium fulvate is/are excluded from inoculant compositions of the present disclosure. Nonlimiting examples of fulvic acids that may be useful in embodiments of the present disclosure include MDL Number MFCD09838488 (CAS Number 479-66-3).

In some embodiments, the inoculant composition comprises one or more betaines (e.g., trimethylglycine).

In some embodiments, the inoculant composition comprises one or more peptones (e.g., bacterial peptones, meat peptones, milk peptones, vegetable peptones and yeast peptones).

In some embodiments, the inoculant composition comprises one or more oxidation control components (e.g., one or more antioxidants and/or oxygen scavengers). According to some embodiments, the inoculant composition comprises one or more oxygen scavengers, such as ascrobic acid, ascorbate salts, catechol and/or sodium hydrogen carbonate. According to some embodiments, the inoculant composition comprises one or more antioxidants, such as ascorbic acid, ascorbyl palmitate, ascorbyl stearate, calcium ascorbate, carotenoids, lipoic acid, phenolic compounds (e.g., flavonoids, flavones, flavonols), potassium ascorbate, sodium ascorbate, thiols (e.g., glutathione, lipoic acid, N-acetyl cysteine), tocopherols, tocotrienols, ubiquinone and/or uric acid. Non-limiting examples of antioxidants include those that are soluble in the cell membrane (e.g., alpha tocopherol (vitamin E), ascorbyl palmitate) and those that are soluble in water (e.g., ascorbic acid and isomers or ascorbic acid, sodium or potassium salts of ascorbic acid or isomers or ascorbic acid, glutathione, sodium or potassium salts of glutathione). In some embodiments, use of a membrane-soluble antioxidant necessitates the addition of one or more surfactants to adequately disperse the antioxidant within the inoculant composition. According to some embodiments, the inoculant composition is/comprises ascorbic acid and/or glutathione.

In some embodiments, the inoculant composition comprises one or more hygroscopic polymers (e.g., hygroscopic agars, albumins, alginates, carrageenans, celluloses, gums (e.g., cellulose gum, guar gum, gum arabic, gum combretum, xantham gum), methyl celluloses, nylons, pectins, polyacrylic acids, polycaprolactones, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches). Non-limiting examples of polymers include AGRIMER™ polymers (e.g., 30, AL-10 LC, AL-22, AT/ATF, VA 3E, VA 31, VA 5E, VA 51, VA 6, VA 6E, VA 7E, VA 71, VEMA AN-216, VEMA AN-990, VEMA AN-1200, VEMA AN-1980, VEMA H-815MS; Ashland Specialty Ingredients, Wilmington, DE), EASYSPERSE™ polymers (Ashland Specialty Ingredients, Wilmington, DE); DISCO™ AG polymers (e.g., L-250, L-280, L-285, L-286, L-320, L-323, L-517, L-519, L-520, L800; Incotec Inc., Salinas, CA), KELZAN® polymers (Bri-Chem Supply Ltd., Calgary, Alberta, CA), SEEDWORX™ polymers (e.g., Bio 200; Aginnovation, LLC, Walnut Groove, CA), TICAXAN® xanthan powders, such as PRE-HYDRATED® TICAXAN® Rapid-3 Powder (TIC Gums, White Marsh, MD) and combinations thereof. Additional examples of polymers may be found in Pouci, et al. AM. J. AGRIC. BIOL. SCI. 3(1):299 (2008).

In some embodiments, the inoculant composition comprises one or more UV protectants (e.g., one or more aromatic amino acids (e.g., tryptophan, tyrosine), carotenoids, cinnamates, lignosulfonates (e.g., calcium lignosulfonate, sodium lignosulfonate), melanins, mycosporines, polyphenols and/or salicylates). Non-limiting examples of UV protectants include Borregaard LignoTech™ lignosulfonates (e.g., Borresperse 3A, Borresperse CA, Borresperse NA, Marasperse AG, Norlig A, Norlig 11D, Ufoxane 3A, Ultrazine NA, Vanisperse CB; Borregaard Lignotech, Sarpsborg, Norway) and combinations thereof. Additional examples of UV protectants may be found in BURGES, FORMULATION OF MICROBIAL BIOPESTICIDES: BENEFICIAL MICROORGANISMS, NEMATODES AND SEED TREATMENTS (Springer Science & Business Media) (2012).

Additional examples of stabilizing compounds, and of combinations of carriers and stabilizing compounds, may be found in International Patent Publication Nos. WO2017/044473, WO2017/044545, WO2017/116837, WO2017/116846, WO2017/210163, WO2017/210166, WO2018/118740, WO2018/175681, WO2018/183491, WO2018/218008, WO2018/218016 and WO2018/218035.

Inoculant compositions of the present disclosure may comprise any suitable biostimulant(s), including, but not limited to, seaweed extracts (e.g., *Ascophyllum nodosum* extracts, such as alginate, *Ecklonia maxima* extracts, etc.), myo-inositol, glycine and combinations thereof.

Inoculant compositions of the present disclosure may comprise any suitable microbial extract(s), including, but not limited to, bacterial extracts, fungal extracts and combinations thereof. In some embodiments, inoculant compositions of the present disclosure comprise one or more extracts of media comprising one or more diazotrophs, phosphate-solubilizing microorganisms and/or biopesticides. In some embodiments, inoculant compositions of the present disclosure comprise an extract of media comprising one or more of the microbial strains included in Appendix A.

Inoculant compositions of the present disclosure may comprise any suitable nutrient(s), including, but not limited to, organic acids (e.g., acetic acid, citric acid, lactic acid, malic acid, taurine, etc.), macrominerals (e.g., phosphorous, calcium, magnesium, potassium, sodium, iron, etc.), trace minerals (e.g., boron, cobalt, chloride, chromium, copper, fluoride, iodine, manganese, molybdenum, selenium, zinc, etc.), vitamins, (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids (α-carotene, β-carotene, cryptoxanthin, lutein, lycopene, zeaxanthin, etc.) and combinations thereof. In some embodiments, inoculant compositions of the present disclosure comprise phosphorous, boron, chlorine, copper, iron, manganese, molybdenum and/or zinc.

Inoculant compositions of the present disclosure may comprise any suitable pest attractant(s) and/or feeding stimulant(s), including, but not limited to, brevicomin, ceralure, codlelure, cue-lure, disparlure, dominicalure, eugenol, frontalin, gossyplure, grandlure, hexalure, ipsdienol, ipsenol, japonilure, latitlure, lineatin, litlure, looplure, medlure, megatomic acid, methyl eugenol, moguchun, α-multistriatin, muscalure, orfalure, oryctalure, ostramone, rescalure, siglure, sulcatol, trimedlure and/or trunc-call.

Inoculant compositions of the present disclosure may comprise any suitable pesticide(s), including, but not limited to, acaricides, fungicides, herbicides, insecticides and nematicides.

Fungicides may be selected to provide effective control against a broad spectrum of phytopathogenic fungi (and fungus-like organisms), including, but not limited to, soilborne fungi from the classes Ascomycetes, Basidiomycetes, Chytridiomycetes, Deuteromycetes (syn. Fungi imperfecti), Peronosporomycetes (syn. Oomycetes), Plasmodiophoromycetes and Zygomycetes. According to some embodiments, the inoculant composition comprises a fungicide (or combination of fungicides) that is toxic to one or more strains of *Albugo* (e.g., *A. candida*), *Alternaria* (e.g., *A. alternata*), *Aspergillus* (e.g., *A. candidus, A. clavatus, A. flavus, A. fumigatus, A. parasiticus, A. restrictus, A. sojae, A. solani*), *Blumeria* (e.g., *B. graminis*), *Botrytis* (e.g., *B. cinerea*), *Cladosporum* (e.g., *C. cladosporioides*), *Colletotrichum* (e.g., *C. acutatum, C. boninense, C. capsici, C. caudatum, C. coccodes, C. crassipes, C. dematium, C. destructivum, C. fragariae, C. gloeosporioides, C. graminicola, C. kehawee, C. lindemuthianum, C. musae, C. orbiculare, C. spinaceae, C. sublineolum, C. trifolii, C. truncatum*), *Fusarium* (e.g., *F. graminearum, F. moniliforme, F. oxysporum, F. roseum, F. tricinctum*), *Helminthosporium, Magnaporthe* (e.g., *M. grisea, M. oryzae*), *Melamspora* (e.g., *M. lini*), *Mycosphaerella* (e.g., *M. graminicola*), *Nematospora, Penicillium* (e.g., *P. rugulosum, P. verrucosum*), *Phakopsora* (e.g., *P. pachyrhizi*), *Phomopsis, Phytiphtoria* (e.g., *P. infestans*), *Puccinia* (e.g., *P. graminis, P. striiformis, P. tritici, P. triticina*), *Pucivinia* (e.g., *P. graministice*), *Pythium, Pytophthora, Rhizoctonia* (e.g., *R. solani*), *Scopulariopsis, Selerotinia, Septoria* (e.g., *S. glycines, S. lycopersici, S. tritici*), *Thielaviopsis* and/or *Ustilago* (e.g. *U. maydis*). Additional examples of fungi may be found in Bradley, *Managing Diseases*, in ILLINOIS AGRONOMY HANDBOOK (2008).

Herbicides may be selected to provide effective control against a broad spectrum of plants, including, but not limited to, plants from the families Asteraceae, Caryophyllaceae, Poaceae and Polygonaceae. According to some embodiments, the inoculant composition comprises an herbicide (or combination of herbicides) that is toxic to one or more strains of *Echinochloa* (e.g., *E. brevipedicellata, E. callopus, E. chacoensis, E. colona, E. crus-galli, E. crus-pavonis, E. elliptica, E. esculenta, E. frumentacea, E. glabrescens, E. haploclada, E. helodes, E. holciformis, E. inundata, E. jaliscana, E. Jubata, E. kimberleyensis, E. lacunaria, E. macrandra, E. muricata, E. obtusiflora, E. oplismenoides, E. orzyoides, E. paludigena, E. picta, E. pithopus, E. polystachya, E. praestans, E. pyramidalis, E. rotundiflora, E. stagnina, E. telmatophila, E. turneriana, E. ugandensis, E. walteri*), *Fallopia* (e.g., *F. baldschuanica, F. japonica, F. sachalinensis*), *Stellaria* (e.g., *S. media*) and/or *Taraxacum* (e.g., *T. albidum, T. aphrogenes, T. brevicorniculatum, T. californicum, T. centrasiatum, T. ceratophorum, T. erythrospermum, T. farinosum, T. holmboei, T. japonicum, T. kok-saghyz, T. laevigatum, T. officinale, T. platycarpum*). Additional species of plants that may be targeted by inoculant compositions of the present disclosure may be found in Hager, *Weed Management*, in ILLINOIS AGRONOMY HANDBOOK (2008) and LOUX ET AL., WEED CONTROL GUIDE FOR OHIO, INDIANA AND ILLINOIS (2015).

Insecticides may be selected to provide effective control against a broad spectrum of insects, including, but not limited to, insects from the orders Coleoptera, Dermaptera, Diptera, Hemiptera, Homoptera, Hymenoptera, Lepidoptera, Orthoptera and Thysanoptera. For example, inoculant compositions of the present disclosure may comprise one or more insecticides toxic to insects from the families Acrididae, Aleytodidae, Anobiidae, Anthomyiidae, Aphididae, Bostrichidae, Bruchidae, Cecidomyiidae, Cerambycidae, Cercopidae, Chrysomelidae, Cicadellidae, Coccinellidae, Cryllotalpidae, Cucujidae, Curculionidae, Dermestidae, Elateridae, Gelechiidae, Lygaeidae, Meloidae, Membracidae, Miridae, Noctuidae, Pentatomidae, Pyralidae, Scarabaeidae, Silvanidae, Spingidae, Tenebrionidae and/or Thripidae. According to some embodiments, the inoculant composition comprises an insecticide (or combination of insecticides) that is toxic to one or more species of *Acalymma, Acanthaoscelides* (e.g., *A. obtectus,*), *Anasa* (e.g., *A. tristis*), *Anastrepha* (e.g., *A. ludens*), *Anoplophora* (e.g., *A. glabripennis*), *Anthonomus* (e.g., *A. eugenii*), *Acyrthosiphon* (e.g., *A. pisum*), *Bactrocera* (e.g. *B. dosalis*), *Bemisia* (e.g., *B. argen-*

*tifolii, B. tabaci), Brevicoryne* (e.g., *B. brassicae), Bruchidius* (e.g., *B. atrolineatus), Bruchus* (e.g., *B. atomarius, B. dentipes, B. lentis, B. pisorum* and/or *B. rufipes), Callosobruchus* (e.g., *C. chinensis, C. maculatus, C. rhodesianus, C. subinnotatus, C. theobromae), Caryedon* (e.g., *C. serratus), Cassadinae, Ceratitis* (e.g., *C. capitata), Chrysomelinae, Circulifer* (e.g., *C. tenellus), Criocerinae, Cryptocephalinae, Cryptolestes* (e.g., *C. ferrugineus, C. pusillis, C. pussilloides), Cylas* (e.g., *C. formicarius), Delia* (e.g., *D. antiqua), Diabrotica, Diaphania* (e.g., *D. nitidalis), Diaphorina* (e.g., *D. citri), Donaciinae, Ephestia* (e.g, *E. cautella, E. elutella, E., keuhniella), Epilachna* (e.g., *E. varivestris), Epiphyas* (e.g., *E. postvittana), Eumolpinae, Galerucinae, Helicoverpa* (e.g., *H. zea), Heteroligus* (e.g., *H. meles), Iobesia* (e.g., *I. botrana), Lamprosomatinae, Lasioderma* (e.g., *L. serricorne), Leptinotarsa* (e.g., *L. decemlineata), Leptoglossus, Liriomyza* (e.g., *L. trifolii), Manducca, Melittia* (e.g., *M. cucurbitae), Myzus* (e.g., *M. persicae), Nezara* (e.g., *N. viridula), Orzaephilus* (e.g., *O. merator, O. surinamensis), Ostrinia* (e.g., *O. nubilalis), Phthorimaea* (e.g., *P. operculella), Pieris* (e.g., *P. rapae), Plodia* (e.g., *P. interpunctella), Plutella* (e.g., *P. xylostella), Popillia* (e.g., *P. japonica), Prostephanus* (e.g., *P. truncates), Psila, Rhizopertha* (e.g., *R. dominica), Rhopalosiphum* (e.g., *R. maidis), Sagrinae, Solenopsis* (e.g., *S. Invicta), Spilopyrinae, Sitophilus* (e.g., *S. granaries, S. oryzae* and/or *S. zeamais), Sitotroga* (e.g., *S. cerealella), Spodoptera* (e.g., *S. frugiperda), Stegobium* (e.g., *S. paniceum), Synetinae, Tenebrio* (e.g., *T. malens* and/or *T. molitor), Thrips* (e.g., *T. tabaci), Trialeurodes* (e.g., *T. vaporariorum), Tribolium* (e.g., *T. castaneum* and/or *T. confusum), Trichoplusia* (e.g., *T. ni), Trogoderma* (e.g., *T. granarium*) and *Trogossitidae* (e.g., *T. mauritanicus*). Additional species of insects that may be targeted by inoculant compositions of the present disclosure may be found in CAPINERA, HANDBOOK OF VEGETABLE PESTS (2001) and Steffey and Gray, *Managing Insect Pests*, in ILLINOIS AGRONOMY HANDBOOK (2008).

Nematicides may be selected to provide effective control against a broad spectrum of nematodes, including, but not limited to, phytoparasitic nematodes from the classes Chromadorea and Enoplea. According to some embodiments, the inoculant composition comprises a nematicide (or combination of nematicides) that is toxic to one or more strains of *Anguina, Aphelenchoides, Belonolaimus, Bursaphelenchus, Ditylenchus, Globodera, Helicotylenchus, Heterodera, Hirschmanniella, Meloidogyne, Naccobus, Pratylenchus, Radopholus, Rotylenshulus, Trichodorus, Tylenchulus* and/or *Xiphinema*. Additional species that may be targeted by inoculant compositions of the present disclosure may be found in CAPINERA, HANDBOOK OF VEGETABLE PESTS (2001) and Niblack, *Nematodes*, in ILLINOIS AGRONOMY HANDBOOK (2008).

In some embodiments, inoculant compositions of the present disclosure comprise one or more chemical fungicides. Non-limiting examples of chemical fungicides include strobilurins, such as azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide; carboxamides, such as carboxanilides (e.g., benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(4'-trifluoromethylthiobiphenyl-2-yl)-3-difluoromethyl-1-methyl-1H-pyra-zole-4-carboxamide, N-(2-(1,3,3-trimethylbutyl)-phenyl)-1,3-dimethyl-5-fluoro-1H-pyrazole-4-carboxamide), carboxylic morpholides (e.g., dimethomorph, flumorph, pyrimorph), benzoic acid amides (e.g., flumetover, fluopicolide, fluopyram, zoxamide), carpropamid, dicyclomet, fenehexamid, mandiproamid, oxytetracyclin, silthiofam, spiroxamine, and N-(6-methoxy-pyridin-3-yl) cyclopropanecarboxylic acid amide; azoles, such as triazoles (e.g., azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole) and imidazoles (e.g., cyazofamid, imazalil, pefurazoate, prochloraz, triflumizol); heterocyclic compounds, such as pyridines (e.g., fluazinam, pyrifenox (cf.D1b), 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine), pyrimidines (e.g., bupirimate, cyprodinil, diflumetorim, fenarimol, ferimzone, mepanipyrim, nitrapyrin, nuarimol, pyrimethanil), piperazines (e.g., triforine), pirroles (e.g., fenpiclonil, fludioxonil), morpholines (e.g., aldimorph, dodemorph, dodemorph-acetate, fenpropimorph, tridemorph), piperidines (e.g., fenpropidin), dicarboximides (e.g., fluoroimid, iprodione, procymidone, vinclozolin), non-aromatic 5-membered heterocycles (e.g., famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester), acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo-[1,5-a]pyrimidine; benzimidazoles, such as carbendazim; and other active substances, such as guanidines (e.g., guanidine, dodine, dodine free base, guazatine, guazatine-acetate, iminoctadine), iminoctadine-triacetate and iminoctadine-tris(albesilate); antibiotics (e.g., kasugamycin, kasugamycin hydrochloride-hydrate, streptomycin, polyoxine and validamycin A); nitrophenyl derivates (e.g., binapacryl, dicloran, dinobuton, dinocap, nitrothal-isopropyl, tecnazen); organometal compounds (e.g., fentin salts, such as fentin-acetate, fentin chloride, fentin hydroxide); sulfur-containing heterocyclyl compounds (e.g., dithianon, isoprothiolane); organophosphorus compounds (e.g., edifenphos, fosetyl, fosetyl-aluminum, iprobenfos, phosphorus acid and its salts, pyrazophos, tolclofos-methyl); organochlorine compounds (e.g., chlorothalonil, dichlofluanid, dichlorophen, flusulfamide, hexachlorobenzene, pencycuron, pentachlorphenole and its salts, phthalide, quintozene, thiophanate-methyl, thiophanate, tolylfluanid, N-(4-chloro-2-nitro-phenyl)-N-ethyl-4-methyl-benzenesulfonamide) and inorganic active substances (e.g., Bordeaux mixture, copper acetate, copper hydroxide, copper oxychloride, basic copper sulfate, sulfur) and combinations thereof. In some embodiments, inoculant compositions of the present disclosure comprise acibenzolar-S-methyl, azoxystrobin, benalaxyl, bixafen, boscalid, carbendazim, cyproconazole, dimethomorph, epoxiconazole, fludioxonil, fluopyram, fluoxastrobin, flutianil, flutolanil, fluxapyroxad, fosetyl-A1, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thiabendazole, thifluzamide, thiophanate, tolclofos-methyl, trifloxystrobin and triticonazole. In some embodiments, inoculant compositions of the present disclosure comprise azoxystrobin, pyraclostrobin, fluoxastrobin, trifloxystrobin, ipconazole, prothioconazole, sedaxane, fludioxonil, metalaxyl, mefenoxam, thiabendazole, fluxapyroxad and/or fluopyram. In some embodiments, inoculant compositions of the present disclosure comprise one or more aromatic hydrocarbons, benzimidazoles, benzthiadiazole, carboxamides, carboxylic acid amides, morpholines, phenylamides, phosphonates, quinone outside inhibitors (e.g. strobilurins), thiazolidines, thiophanates, thiophene carboxamides and/or triazoles.

In some embodiments, inoculant compositions of the present disclosure comprise one or more chemical herbicides. Non-limiting examples of chemical herbicides include 2,4-dichlorophenoxyacetic acid (2,4-D), 2,4,5-trichlorophenoxyacetic acid (2,4,5-T), ametryn, amicarbazone, aminocyclopyrachlor, acetochlor, acifluorfen, alachlor, atrazine, azafenidin, bentazon, benzofenap, bifenox, bromacil, bromoxynil, butachlor, butafenacil, butroxydim, carfentrazone-ethyl, chlorimuron, chlorotoluro, clethodim, clodinafop, clomazone, cyanazine, cycloxydim, cyhalofop, desmedipham, desmetryn, dicamba, diclofop, diflufenican, dimefuron, diuron, dithiopyr, ethofumesate, fenoxaprop, fluazifop, fluazifop-P, flufenacet, fluometuron, flufenpyr-ethyl, flumiclorac-pentyl, flumioxazin, fluoroglycofen, fluthiacet-methyl, fomesafe, fomesafen, foramsulfuron, glyphosate, glufosinate, haloxyfop, hexazinone, imazamox, imazaquin, imazethapyr, indaziflam, iodosulfuron, ioxynil, isoproturon, isoxaflutole, lactofen, linuron, mecoprop, mecoprop-P, mesosulfuron, mesotrion, metamitron, metazochlor, methibenzuron, metolachlor (and S-metolachlor), metoxuron, metribuzin, monolinuron, oxadiargyl, oxadiazon, oxaziclomefone, oxyfluorfen, phenmedipham, pretilachlor, profoxydim, prometon, prometry, propachlor, propanil, propaquizafop, propisochlor, propoxycarbazone, pyraflufen-ethyl, pyrazon, pyrazolynate, pyrazoxyfen, pyridate, quizalofop, quizalofop-P (e.g., quizalofop-ethyl, quizalofop-P-ethyl, clodinafop-propargyl, cyhalofop-butyl, diclofop-methyl, fenoxaprop-P-ethyl, fluazifop-P-butyl, haloxyfop-methyl, haloxyfop-R-methyl), saflufenacil, sethoxydim, siduron, simazine, simetryn, sulcotrione, sulfentrazone, tebuthiuron, tembotrione, tepraloxydim, terbacil, terbumeton, terbuthylazine, thaxtomin (e.g., the thaxtomins described in U.S. Pat. No. 7,989,393), thenylchlor, thiencarbazone-methyl, tralkoxydim, triclopyr, trietazine, tropramezone, salts and esters thereof; racemic mixtures and resolved isomers thereof and combinations thereof. In some embodiments, inoculant compositions of the present disclosure comprise acetochlor, clethodim, dicamba, flumioxazin, fomesafen, glyphosate, glufosinate, mesotrione, quizalofop, saflufenacil, sulcotrione, S-3100 and/or 2,4-D. In some embodiments, inoculant compositions of the present disclosure comprise glyphosate, glufosinate, dicamba, 2,4-D, acetochlor, metolachlor, pyroxasulfone, flumioxazin, fomesafen, lactofen, metribuzin, mesotrione, and/or ethyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate. In some embodiments, inoculant compositions of the present disclosure comprise one or more acetyl CoA carboxylase (ACCase) inhibitors, acetolactate synthase (ALS) inhibitors, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, nucleic acid inhibitors and/or one or more salts, esters, racemic mixtures and/or resolved isomers thereof.

In some embodiments, inoculant compositions of the present disclosure comprise one or more chemical insecticides and/or nematicides. Non-limiting examples of chemical insecticides and nematicides include abamectin, acrinathrin, aldicarb, aldoxycarb, alpha-cypermethrin, betacyfluthrin, bifenthrin, cyhalothrin, cypermethrin, deltamethrin, esfenvalerate, etofenprox, fenpropathrin, fenvalerate, flucythrinate, fosthiazate, lambda-cyhalothrin, gamma-cyhalothrin, permethrin, tau-fluvalinate, transfluthrin, zeta-cypermethrin, cyfluthrin, bifenthrin, tefluthrin, eflusilanat, fubfenprox, pyrethrin, resmethrin, imidacloprid, acetamiprid, thiamethoxam, nitenpyram, thiacloprid, dinotefuran, clothianidin, chlorfluazuron, diflubenzuron, lufenuron, teflubenzuron, triflumuron, novaluron, flufenoxuron, hexaflumuron, bistrifluoron, noviflumuron, buprofezin, cyromazine, methoxyfenozide, tebufenozide, halofenozide, chromafenozide, endosulfan, fipronil, ethiprole, pyrafluprole, pyriprole, flubendiamide, chlorantraniliprole, cyazypyr, emamectin, emamectin benzoate, abamectin, ivermectin, milbemectin, lepimectin, tebufenpyrad, fenpyroximate, pyridaben, fenazaquin, pyrimidifen, tolfenpyrad, dicofol, cyenopyrafen, cyflumetofen, acequinocyl, fluacrypyrin, bifenazate, diafenthiuron, etoxazole, clofentezine, spinosad, triarathen, tetradifon, propargite, hexythiazox, bromopropylate, chinomethionat, amitraz, pyrifluquinazon, pymetrozine, flonicamid, pyriproxyfen, diofenolan, chlorfenapyr, metaflumizone, indoxacarb, chlorpyrifos, spirodiclofen, spiromesifen, spirotetramat, pyridalyl, spinctoram, acephate, triazophos, profenofos, oxamyl, spinetoram, fenamiphos, fenamipclothiahos, 4-{[(6-chloropyrid-3-yl)methyl](2,2-difluoroethyl)amino}furan-2(5H)-one, 3,5-disubstituted-1,2,4-oxadiazole compounds, 3-phenyl-5-(thien-2-yl)-1,2,4-oxadiazole, cadusaphos, carbaryl, carbofuran, ethoprophos, thiodicarb, aldicarb, aldoxycarb, metamidophos, methiocarb, sulfoxaflor, methamidophos, cyantraniliprole and tioxazofen and combinations thereof. In some embodiments, inoculant compositions of the present disclosure comprise abamectin, aldicarb, aldoxycarb, bifenthrin, carbofuran, chlorantraniliporle, chlothianidin, cyfluthrin, cyhalothrin, cypermethrin, cyantraniliprole, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam, tioxazofen and/or thiodicarb. In some embodiments, inoculant compositions of the present disclosure comprise one or more carbamates, diamides, macrocyclic lactones, neonicotinoids, organophosphates, phenylpyrazoles, pyrethrins, spinosyns, synthetic pyrethroids, tetronic acids and/or tetramic acids. In some embodiments, inoculant compositions of the present disclosure comprise an insecticide selected from the group consisting of clothianidin, thiamethoxam, imidacloprid, cyantraniliprole, chlorantraniliprole, fluopyram and tioxazafen.

In some embodiments, inoculant compositions of the present disclosure comprise one or more biopesticides (e.g., one or more biofungicides, bioinsecticides and/or bionematicides). Examples of microbial strains that exhibit biopesticidal activity are included in Appendix A, along with strains that exhibit nitrogen-fixing activity, phosphate-solubilizing activity, etc. Additional examples of pesticides may be found in Bradley, *Managing Diseases*, in Illinois Agronomy Handbook (2008); Hager, *Weed Management*, in Illinois Agronomy Handbook (2008); Loux et al., Weed Control Guide for Ohio, Indiana and Illinois (2015); Niblack, *Nematodes*, in Illinois Agronomy Handbook (2008); and Steffey and Gray, *Managing Insect Pests*, in Illinois Agronomy Handbook (2008).

Inoculant compositions of the present disclosure may comprise any suitable plant signal molecule(s), including, but not limited to, lipo-chitooligosaccharides (LCOs), chitin oligomers, chitosan oligomers, chitinous compounds, flavonoids, non-flavonoid nod-gene inducers, jasmonic acid or derivatives thereof, linoleic acid or derivatives thereof, linolenic acid or derivatives thereof and karrikins.

Inoculant compositions of the present disclosure may comprise any suitable LCO(s). LCOs, sometimes referred to as symbiotic nodulation (Nod) signals or Nod factors, consist of an oligosaccharide backbone of β-1,4-linked N-acetyl-D-glucosamine ("GlcNAc") residues with an N-linked fatty acyl chain condensed at the non-reducing end. LCOs differ in the number of GlcNAc residues in the backbone, in the length and degree of saturation of the fatty acyl chain and in the substitutions of reducing and non-reducing sugar residues. See, e.g., Denarie, et al., Ann. Rev. Biochem. 65:503 (1996); Hamel, et al., Planta 232:787 (2010); Prome, et al., Pure & Appl. Chem. 70(1):55 (1998).

In some embodiments, inoculant compositions of the present disclosure comprise one or more of the LCOs described in International Patent Publication No. WO 2019/136198. For example, inoculant compositions of the present disclosure may comprise one or more of the LCOs set forth below as structures V-XII:

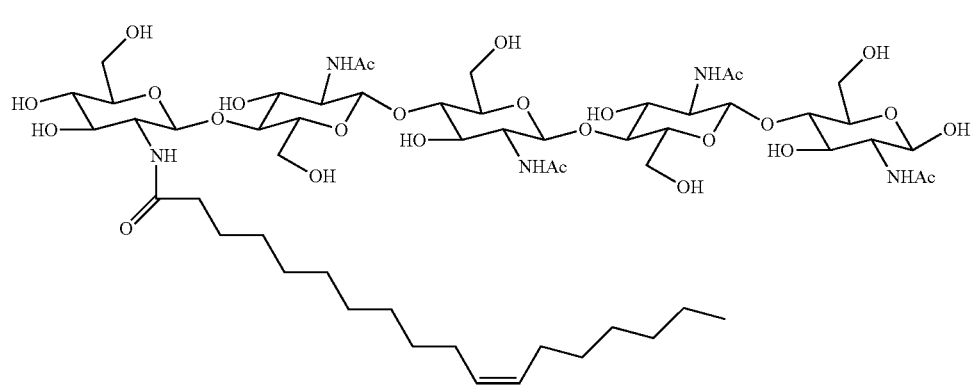

(V)

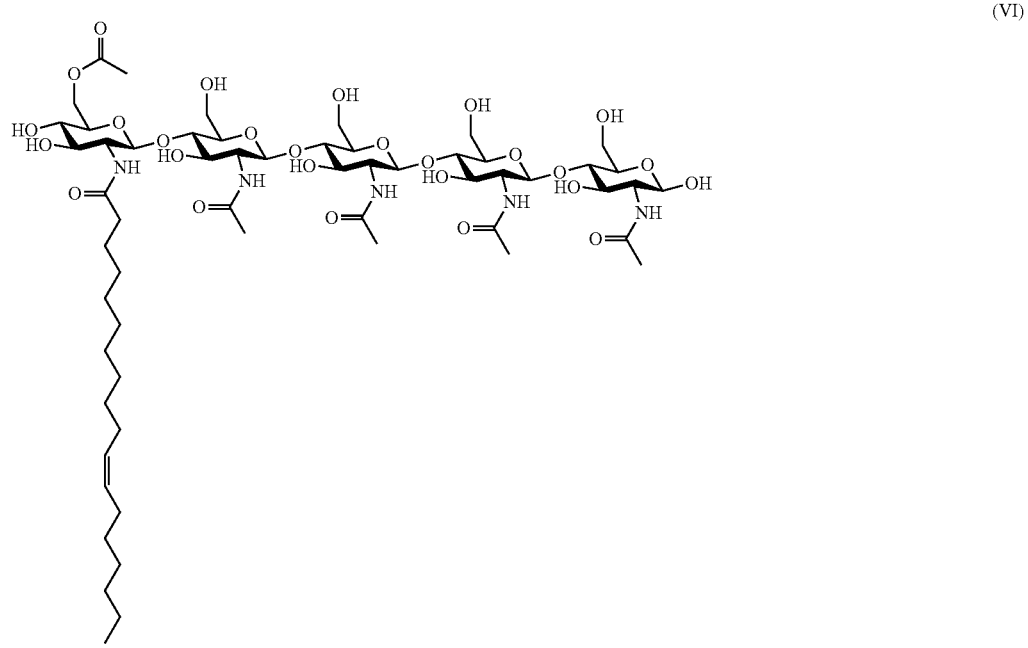

(VI)

(VII)
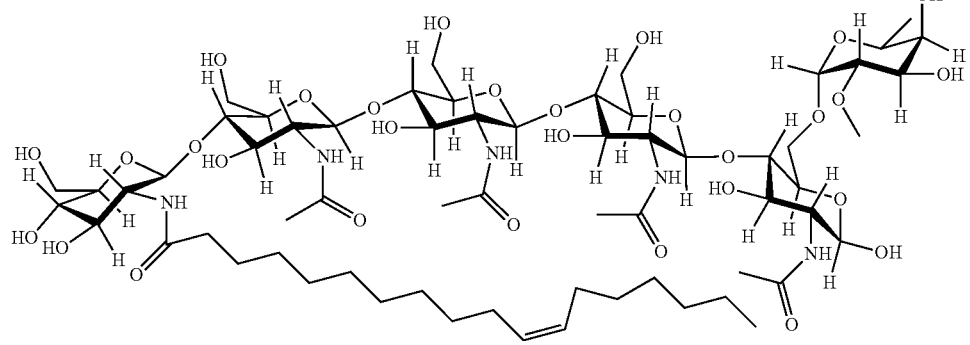
(VIII)
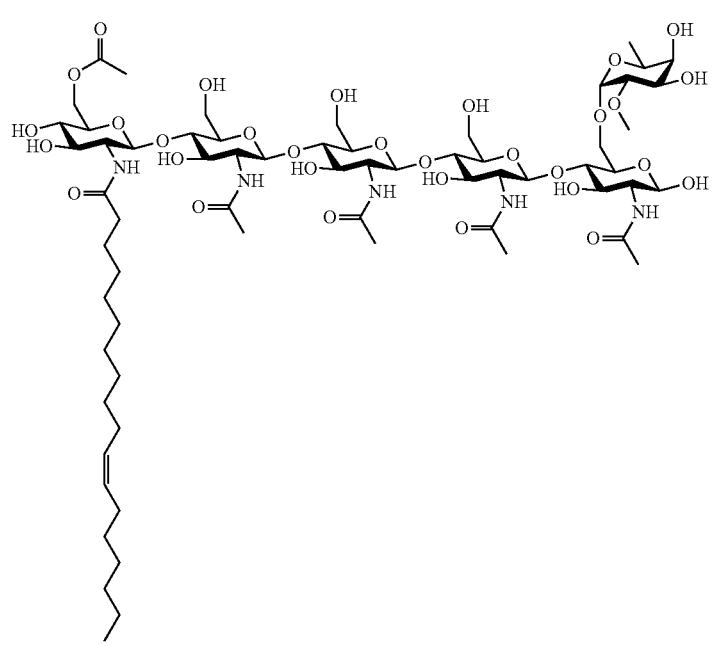
(IX)
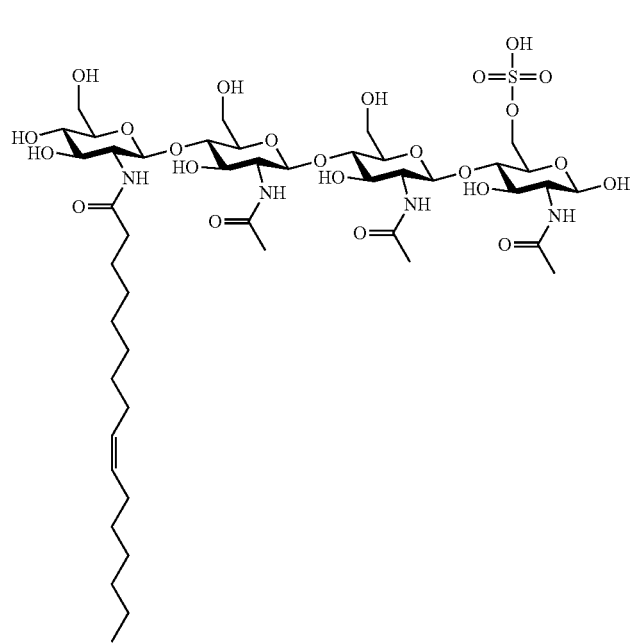

-continued
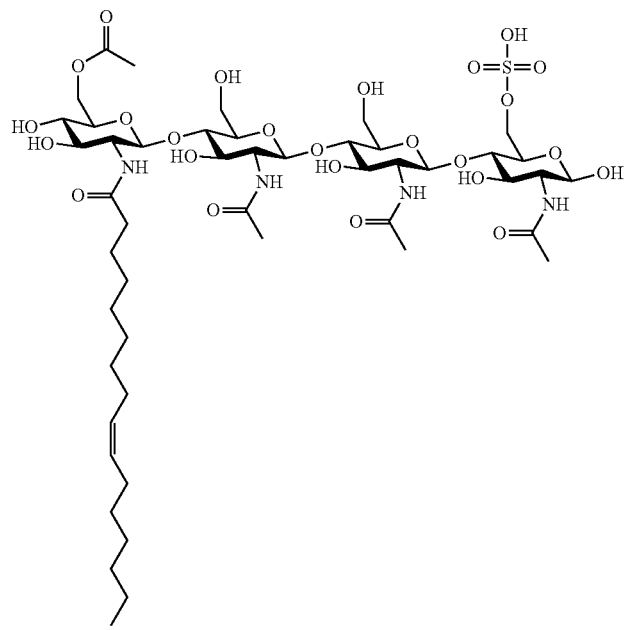
(X)
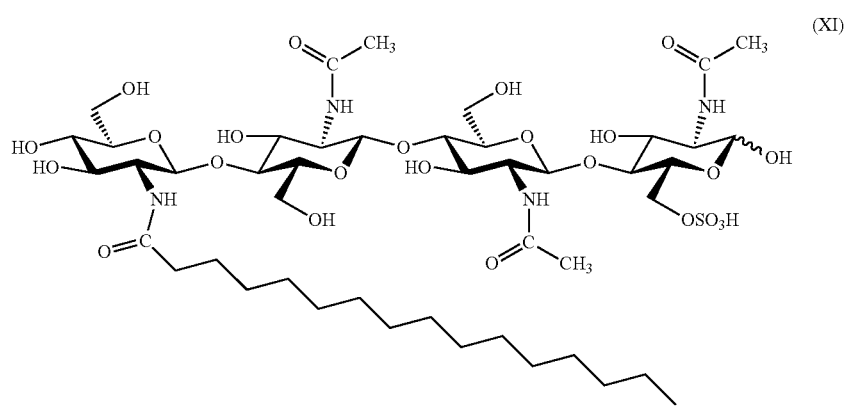
(XI)
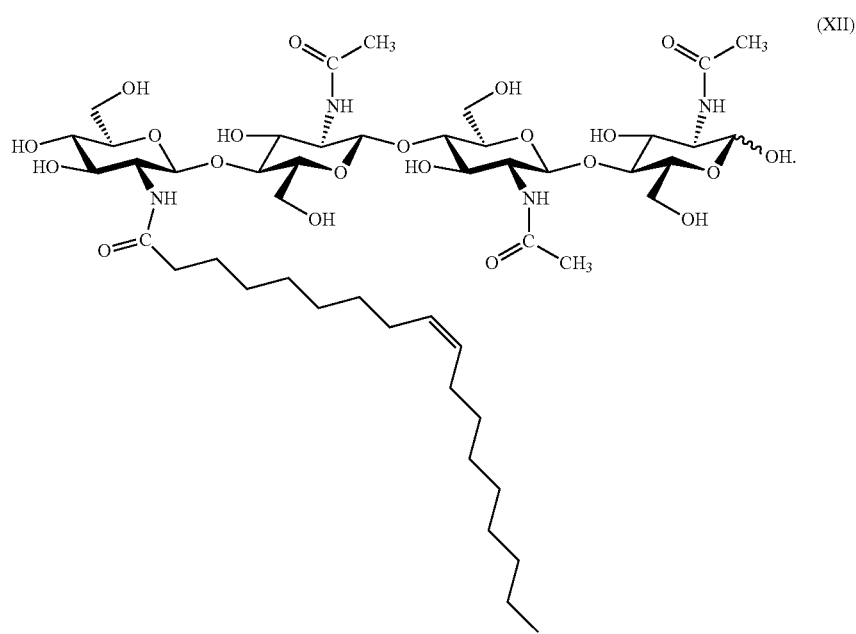
(XII)

In some embodiments, inoculant compositions of the present disclosure comprise one or more of the LCO compositions described in International Patent Publication No. WO 2019/136198.

LCOs may be obtained from any suitable source. In some embodiments, the LCO is obtained (i.e., isolated and/or purified) from a bacterial strain. For example, in some embodiments, inoculant compositions of the present disclosure comprise one or more LCOs obtained from a of *Azorhizobium, Bradyrhizobium* (e.g., *B. japonicum*), *Mesorhizobium, Rhizobium* (e.g., *R. leguminosarum*), or *Sinorhizobium* (e.g., *S. meliloti*). In some embodiments, the LCO is obtained (i.e., isolated and/or purified) from a mycorrhizal fungus. For example, in some embodiments, inoculant compositions of the present disclosure comprise one or more LCOs obtained from a strain of Glomerocycota (e.g., *Glomus intraradicus*). See, e.g., WO 2010/049751 (in which the LCOs are referred to as "Myc factors"). In some embodiments, the LCO is synthetic. For example, in some embodiments, inoculant compositions of the present disclosure comprise one or more of the synthetic LCOs described in WO 2005/063784, WO 2007/117500 and/or WO 2008/071674. In some embodiments, the synthetic LCO contains one or more modifications or substitutions, such as those described in Spaink, CRIT. REV. PLANT SCI. 54:257 (2000) and D'Haeze, supra. LCOs and precursors for the construction of LCOs (e.g., chitin oligomers, which are themselves useful as plant signal molecules) may be synthesized by genetically engineered organisms. See, e.g., Samain et al., CARBOHYDRATE RES. 302:35 (1997); Cottaz, et al., METH. ENG. 7(4):311 (2005); and Samain, et al., J. BIOTECHNOL. 72:33 (1999).

It is to be understood that compositions and methods of the present disclosure may comprise analogues, derivatives, hydrates, isomers, salts and/or solvates of LCOs. Thus, in some embodiments, inoculant compositions of the present disclosure comprise one, two, three, four, five, six, seven, eight, nine, ten, or more LCOs represented by one or more of formulas I-IV and/or structures V-XXXIII as set forth in International Patent Publication No. WO 2019/136198 and/or one, two, three, four, five, six, seven, eight, nine, ten, or more analogues, derivatives, hydrates, isomers, salts and/or solvates of LCOs represented by one or more of formulas IIV and/or structures V-XXXIII as set forth in International Patent Publication No. WO 2019/136198.

LCOs (and derivatives thereof) may be utilized in various forms of purity and may be used alone or in the form of a culture of LCO-producing bacteria or fungi. In some embodiments, the LCO(s) included in inoculant compositions of the present disclosure is/are at least 50%, 55%, 60%, 65%, 70%, 75%, 80%, 85%, 90%, 91%, 92%, 93%, 94%, 95%, 96%, 97%, 98%, 99%, 99.5% or more pure.

Inoculant compositions of the present disclosure may comprise any suitable chitin oligomer(s) and/or chitosan oligomer(s). See, e.g., D'Haeze et al., GLYCOBIOL. 12(6):79R (2002); Demont-Caulet et al., PLANT PHYSIOL. 120(1):83 (1999); Hanel et al., PLANTA 232:787 (2010); Muller et al., PLANT PHYSIOL. 124:733 (2000); Robina et al., TETRAHEDRON 58:521-530 (2002); Rouge et al., *Docking of Chitin Oligomers and Nod Factors on Lectin Domains of the LysM-RLK Receptors in the Medicago-Rhizobium Symbiosis*, in THE MOLECULAR IMMUNOLOGY OF COMPLEX CARBOHYDRATES-3 (Springer Science, 2011); Van der Holst et al., CURR. OPIN. STRUC. BIOL. 11:608 (2001); Wan et al., PLANT CELL 21:1053 (2009); and PCT/F100/00803 (2000).

In some embodiments, inoculant compositions of the present disclosure comprise one or more of the chitin oligomers described in International Patent Publication No. WO 2019/136198.

In some embodiments, inoculant compositions of the present disclosure comprise one or more of the chitosan oligomers described in International Patent Publication No. WO 2019/136198.

Chitin oligosaccharides and chitosan oligosaccharides may be obtained from any suitable source. Chitin oligosaccharides and chitosan oligosaccharides may be harvested from chitin/chitosan (see, e.g., Aam et al., MAR. DRUGS 8:1482 (2010); D'Haeze et al., GLYCOBIOL. 12(6):79R (2002); Demont-Caulet et al., PLANT PHYSIOL. 120(1):83 (1999); Hanel et al., PLANTA 232:787 (2010); Limpanavech et al., SCIENTIA HORTICULTURAE 116:65 (2008); Lodhi et al., BIOMED RES. INTL. Vol. 2014 Art. 654913 (March 2014); Mourya et al., POLYMER SCI. 53(7):583 (2011); Muller et al., PLANT PHYSIOL. 124:733 (2000); Robina et al., TETRAHEDRON 58:521 (2002); Rouge et al., *The Molecular Immunology of Complex Carbohydrates*, in ADVANCES IN EXPERIMENTAL MEDICINE AND BIOLOGY (Springer Science, 2011); Van der Holst et al., CURR. OPIN. STRUC. BIOL. 11:608 (2001); Wan et al., PLANT CELL 21:1053 (2009); Xia et al., FOOD HYDROCOLLOIDS 25:170 (2011); PCT/F100/00803 (2000)). They may also be synthetically generated (see, e.g., Cottaz et al., METH. ENG. 7(4):311 (2005); Samain et al., CARBOHYDRATE RES. 302:35 (1997); Samain et al., J. BIOTECHNOL. 72:33 (1999)). In some embodiments, they are derived from a naturally occurring LCO. For example, in some embodiments, inoculant compositions of the present disclosure comprise one or more chitin/chitosan oligosaccharides derived from an LCO obtained (i.e., isolated and/or purified) from a strain of *Azorhizobium, Bradyrhizobium* (e.g., *B. japonicum*), *Mesorhizobium, Rhizobium* (e.g., *R. leguminosarum*), *Sinorhizobium* (e.g., *S. meliloti*), or mycorhizzal fungus (e.g., *Glomus intraradicus*). In some embodiments, inoculant compositions of the present disclosure comprise one or more chitin oligosaccharides and/or chitosan oligosaccharides derived from an LCO obtained (i.e., isolated and/or purified) from a strain of *Azorhizobium, Bradyrhizobium* (e.g., *B. japonicum*), *Mesorhizobium, Rhizobium* (e.g., *R. leguminosarum*), *Sinorhizobium* (e.g., *S. meliloti*), or mycorhizzal fungus (e.g., *Glomus intraradicus*). In some embodiments, the chitin oligosaccharide(s) and/or chitosan oligosaccharide(s) is/are derived from an LCO represented by one or more of formulas I-IV and/or structures V-XXXIII as set forth in International Patent Publication No. WO 2019/136198. Thus, in some embodiments, inoculant compositions of the present disclosure may comprise one or more chitin oligosaccharides represented by one or more of formulas IIV and/or structures V-XXXIII as set forth in International Patent Publication No. WO 2019/136198 except that the pendant fatty acid is replaced with a hydrogen or methyl group.

It is to be understood that compositions of the present disclosure may comprise analogues, derivatives, hydrates, isomers, salts and/or solvates of chitin oligosaccharides and/or chitosan oligosaccharides. Thus, in some embodiments, inoculant compositions of the present disclosure comprise one, two, three, four, five, six, seven, eight, nine, ten, or more chitin oligosaccharides represented by one or more of formulas XXXIV-XXXV and/or structures XXXVI-LXXXIII as set forth in International Patent Publication No. WO 2019/136198 and/or one, two, three, four, five, six, seven, eight, nine, ten, or more analogues, derivatives, hydrates, isomers, salts and/or solvates of chitin oligosaccharides represented by one or more of formulas XXXIV-XXXV and/or structures XXXVI-LXXXIII as set forth in International Patent Publication No. WO 2019/136198.

Chitin oligosaccharides and chitosan oligosaccharides (and analogues, derivatives, hydrates, isomers, salts and/or solvates thereof) may be utilized in various forms of purity and may be used alone or in the form of a culture of CO-producing bacteria or fungi. In some embodiments, the chitin oligosaccharides and/or chitosan oligosaccharides included in inoculant compositions of the present disclosure is/are at least 50%, 55%, 60%, 65%, 70%, 75%, 80%, 85%, 90%, 91%, 92%, 93%, 94%, 95%, 96%, 97%, 98%, 99%, 99.5% or more pure.

Inoculant compositions of the present disclosure may comprise any suitable chitinous compound(s), including, but not limited to, chitin (IUPAC: N-[5-[[3-acetylamino-4,5-dihydroxy-6-(hydroxymethyl)oxan-2yl]methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), chitosan (IUPAC: 5-amino-6-[5-amino-6-[5-amino-4,6-dihydroxy-2 (hydroxymethyloxan-3-yl]oxy-4-hydroxy-2-(hydroxymethyl)oxan-3-yl]oxy-2 (hydroxymethyl)oxane-3,4-diol) and isomers, salts and solvates thereof.

Chitins and chitosans, which are major components of the cell walls of fungi and the exoskeletons of insects and crustaceans, are composed of GIcNAc residues.

Chitins and chitosans may be obtained commercially or prepared from insects, crustacean shells, or fungal cell walls. Methods for the preparation of chitin and chitosan are known in the art. See, e.g., U.S. Pat. No. 4,536,207 (preparation from crustacean shells) and U.S. Pat. No. 5,965,545 (preparation from crab shells and hydrolysis of commercial chitosan); Pochanavanich, et al., LETT. APPL. MICROBIOL. 35:17 (2002) (preparation from fungal cell walls).

Deacetylated chitins and chitosans may be obtained that range from less than 35% to greater than 90% deacetylation and cover a broad spectrum of molecular weights, e.g., low molecular weight chitosan oligomers of less than 15 kD and chitin oligomers of 0.5 to 2 kD; "practical grade" chitosan with a molecular weight of about 15 kD; and high molecular weight chitosan of up to 70 kD. Chitin and chitosan compositions formulated for seed treatment are commercially available. Commercial products include, for example, ELEXA® (Plant Defense Boosters, Inc.) and BEYOND™ (Agrihouse, Inc.).

Inoculant compositions of the present disclosure may comprise any suitable flavonoid(s), including, but not limited to, anthocyanidins, anthoxanthins, chalcones, coumarins, flavanones, flavanonols, flavans and isoflavonoids, as well as analogues, derivatives, hydrates, isomers, polymers, salts and solvates thereof.

Flavonoids are phenolic compounds having the general structure of two aromatic rings connected by a three-carbon bridge. Classes of flavonoids include are known in the art. See, e.g., Jain et al., J. PLANT BIOCHEM. & BIOTECHNOL. 11:1 (2002); Shaw et al., ENVIRON. MICROBIOL. 11:1867 (2006). Flavonoid compounds are commercially available, e.g., from Novozymes BioAg, Saskatoon, Canada; Natland International Corp., Research Triangle Park, NC; MP Biomedicals, Irvine, CA; LC Laboratories, Woburn MA. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast, as described in Ralston et al., PLANT PHYSIOL. 137:1375 (2005).

In some embodiments, inoculant compositions of the present disclosure comprise one or more anthocyanidins. According to some embodiments, the inoculant composition comprises cyanidin, delphinidin, malvidin, pelargonidin, peonidin and/or petunidin.

In some embodiments, inoculant compositions of the present disclosure comprise one or more anthoxanthins According to some embodiments, the inoculant composition comprises one or more flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin).

In some embodiments, inoculant compositions of the present disclosure comprise one or more flavanones. According to some embodiments, the inoculant composition comprises butin, eriodictyol, hesperetin, hesperidin, homoeriodictyol, isosakuranetin, naringenin, naringin, pinocembrin, poncirin, sakuranetin, sakuranin and/or sterubin.

In some embodiments, inoculant compositions of the present disclosure comprise one or more flavanonols. According to some embodiments, the inoculant composition comprises dihydrokaempferol and/or taxifolin.

In some embodiments, inoculant compositions of the present disclosure comprise one or more flavans. According to some embodiments, the inoculant composition comprises one or more flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin) and/or dimers, trimers, oligomers and/or polymers thereof (e.g., one or more proanthocyanidins).

In some embodiments, inoculant compositions of the present disclosure comprise one or more isoflavonoids. According to some embodiments, the inoculant composition comprises one or more isoflavones (e.g, biochanin A, daidzein, formononetin, genistein and/or glycitein), isoflavanes (e.g., equol, ionchocarpane and/or laxifloorane), isoflavandiols, isoflavenes (e.g., glabrene, haginin D and/or 2-methoxyjudaicin), coumestans (e.g., coumestrol, plicadin and/or wedelolactone), pterocarpans and/or roetonoids.

Inoculant compositions of the present disclosure may comprise any suitable flavonoid derivative, including, but not limited to, neoflavonoids (e.g, calophyllolide, coutareagenin, dalbergichromene, dalbergin, nivetin) and pterocarpans (e.g., bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine, trifolirhizin).

Flavonoids and derivatives thereof may be incorporated into inoculant compositions of the present disclosure in any suitable form, including, but not limited to, polymorphic and crystalline forms.

Inoculant compositions of the present disclosure may comprise any suitable non-flavonoid nod-gene inducer(s), including, but not limited to, jasmonic acid ([1R-[1α,2β(Z)]]-3-oxo-2-(pentenyl)cyclopentaneacetic acid; JA), linoleic acid ((Z,Z)-9,12-Octadecadienoic acid) and linolenic acid ((Z,Z,Z)-9,12,15-octadecatrienoic acid), as well as analogues, derivatives, hydrates, isomers, polymers, salts and solvates thereof.

Jasmonic acid and its methyl ester, methyl jasmonate (MeJA), collectively known as jasmonates, are octadecanoid-based compounds that occur naturally in some plants (e.g., wheat), fungi (e.g., *Botryodiplodia theobromae, Gibberella fujikuroi*), yeast (e.g., *Saccharomyces cerevisiae*) and bacteria (e.g., *Escherichia coli*). Linoleic acid and linolenic acid may be produced in the course of the biosynthesis of jasmonic acid. Jasmonates, linoleic acid and linolenic acid (and their derivatives) are reported to be inducers of nod gene expression or LCO production by rhizobacteria. See, e.g., Mabood, et al. PLANT PHYSIOL. BIOCHEM. 44(11):759 (2006); Mabood et al., AGR. J. 98(2):289 (2006); Mabood, et al., FIELD CROPS RES. 95(2-3):412 (2006); Mabood & Smith, *Linoleic and linolenic acid induce the expression of nod genes in Bradyrhizobium japonicum USDA* 3, PLANT BIOL. (2001). Non-limiting examples of derivatives of jasmonic acid, linoleic acid, linolenic acid include esters, amides, glycosides and salts. Representative esters are compounds in which the carboxyl group of linoleic acid, linolenic acid, or jasmonic acid has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a —COR group, where R is an NR$^2$R$^3$ group, in which R$^2$ and R$^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salts may be precipitated from solution and be collected by filtration or may be recovered by other means such as by evaporation of the solvent.

Inoculant compositions of the present disclosure may comprise any suitable karrakin(s), including, but not limited to, 2H-furo[2,3-c]pyran-2-ones, as well as analogues, derivatives, hydrates, isomers, polymers, salts and solvates thereof.

In some embodiments, the inoculant composition comprises one or more karrakins represented by formula LXXXIV as set forth in International Patent Publication No. WO 2019/136198.

Examples of biologically acceptable salts of karrakins include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by formula XXXX and which may be suitable for use in the present disclosure include 3-methyl-2H-furo[2,3-c]pyran-2-one (where $R_1$=$CH_3$, $R_2$, $R_3$, $R_4$=H), 2H-furo[2,3-c]pyran-2-one (where $R_1$, $R_2$, $R_3$, $R_4$=H), 7-methyl-2H-furo[2,3-c]pyran-2-one (where $R_1$, $R_2$, $R_4$=H, $R_3$=$CH_3$), 5-methyl-2H-furo[2,3-c]pyran-2-one (where $R_1$, $R_2$, $R_3$=H, $R_4$=$CH_3$), 3,7-dimethyl-2H-furo[2,3-c]pyran-2-one (where $R_1$, $R_3$=$CH_3$, $R_2$, $R_4$=H), 3,5-dimethyl-2H-furo[2,3-c]pyran-2-one (where $R_1$, $R_4$=$CH_3$, $R_2$, $R_3$=H), 3,5,7-trimethyl-2H-furo[2,3-c]pyran-2-one (where $R_1$, $R_3$, $R_4$=$CH_3$, $R_2$=H), 5-methoxymethyl-3-methyl-2H-furo[2,3-c]pyran-2-one (where $R_1$=CH3, $R_2$, $R_3$=H, $R_4$=$CH_2OCH_3$), 4-bromo-3,7-dimethyl-2H-furo[2,3-c]pyran-2-one (where $R_1$, $R_3$=CH3, $R_2$=Br, $R_4$=H), 3-methylfuro[2,3-c]pyridin-2(3H)-one (where Z=NH, $R_1$=$CH_3$, $R_2$, $R_3$, $R_4$=H) and 3,6-dimethylfuro[2,3-c]pyridin-2(6H)-one (where Z=N—$CH_3$, $R_1$=$CH_3$, $R_2$, $R_3$, $R_4$=H). See, e.g., U.S. Pat. No. 7,576,213; Halford, *Smoke Signals*, in CHEM. ENG. NEWS (Apr. 12, 2010) (reporting that karrikins or butenolides contained in smoke act as growth stimulants and spur seed germination after a forest fire and can invigorate seeds such as corn, tomatoes, lettuce and onions that had been stored).

Inoculant compositions of the present disclosure may comprise gluconolactone and/or one or more analogues, derivatives, hydrates, isomers, polymers, salts and/or solvates thereof.

Inoculant compositions of the present disclosure may comprise any suitable excipient(s), including, but not limited to, dispersants, drying agents, anti-freezing agents, seed flowability agents, safeners, anti-settllgn agents, pH buffers and adhesives.

Inoculant compositions of the present disclosure may comprise any suitable agriculturally acceptable dispersant(s), including, but not limited to, surfactants and wetting agents. Selection of appropriate dispersants will depend on the intended application(s) and the microorganism(s) present in the inoculant composition. In general, the dispersant(s) will have low toxicity for the microorganism(s) in the inoculant composition and for the plant part(s) to which the inoculant composition is to be applied. In some embodiments, the dispersant(s) will be selected to wet and/or emulsify one or more soils. Non-limiting examples of dispersants include Atlox™ (e.g., 4916, 4991; Croda International PLC, Edison, NJ), Atlox METASPERSE™ (Croda International PLC, Edison, NJ), BIO-SOFT® (e.g., N series, such as N1-3, N1-7, N1-5, N1-9, N23-3, N2.3-6.5, N25-3, N25-7, N25-9, N91-2.5, N91-6, N91-8; Stepan Company, Northfield, IL), MAKON® nonionic surfactants (e.g., DA-4, DA-6 and DA-9; Stepan Company, Northfield, IL), MORWET® powders (Akzo Nobel Surface Chemistry LLC, Chicago, IL), MULTIWET™ surfactants (e.g., MO-85P-PW-(AP); Croda International PLC, Edison, NJ), SILWET® L-77 (Helena Chemical Company, Collierville, TN), SPAN™ surfactants (e.g., 20, 40, 60, 65, 80 and 85; Croda Inc., Edison NJ), TAMOL™ dispersants (The Dow Chemical Company, Midland, MI), TERGITOL™ surfactants (e.g., TMN-6 and TMN-100×; The Dow Chemical Company, Midland, MI), TERSPERSE surfactants (e.g., 2001, 2020, 2100, 2105, 2158, 2700, 4894 and 4896; Hunstman Corp., The Woodlands, TX), TRITON™ surfactants (e.g., X-100; The Dow Chemical Company, Midland, MI), TWEEN® surfactants (e.g., TWEEN® 20, 21, 22, 23, 28, 40, 60, 61, 65, 80, 81 and 85; Croda International PLC, Edison, NJ) and combinations thereof. Additional examples of dispersants may be found in BAIRD & ZUBLENA. 1993. SOIL FACTS: USING WETTING AGENTS (NONIONIC SURFACTANTS) ON SOIL (North Carolina Cooperative Extension Service Publication AG-439-25) (1993); BURGES, FORMULATION OF MICROBIAL BIOPESTICIDES: BENEFICIAL MICROORGANISMS, NEMATODES AND SEED TREATMENTS (Springer Science & Business Media) (2012); MCCARTY, WETTING AGENTS (Clemson University Cooperative Extension Service Publication) (2001).

In some embodiments, inoculant compositions of the present disclosure comprise one or more anionic surfactants. According to some embodiments, the inoculant composition comprises one or more water-soluble anionic surfactants and/or one or more water-insoluble anionic surfactants, optionally one or more anionic surfactants selected from the group consisting of alkyl carboxylates (e.g., sodium stearate), alkyl sulfates (e.g., alkyl lauryl sulfate, sodium lauryl sulfate), alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and xylene sulfonates.

In some embodiments, inoculant compositions of the present disclosure comprise one or more cationic surfactants. According to some embodiments, the inoculant composition comprises one or more pH-dependent amines and/or one or more quaternary ammonium cations, optionally one or more cationic surfactants selected from the group consisting of alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide and/or octenidine dihydrochloride.

In some embodiments, inoculant compositions of the present disclosure comprise one or more nonionic surfactants. According to some embodiments, the inoculant composition comprises one or more water-soluble nonionic surfactants and/or one or more water-insoluble nonionic surfactants, optionally one or more nonionic surfactants selected from the group consisting of alcohol ethoxylates (e.g., TERGITOL™ 15-S surfactants, such as TERGITOL™ 15-S-9 (The Dow Chemical Company, Midland, MI)), alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers, glycerol esters, glycol alkyl ethers (e.g., polyoxyethylene glycol alkyl ethers, polyoxypropylene glycol alkyl ethers), glycol alkylphenol ethers (e.g., polyoxyethylene glycol alkylphenol ethers,), glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols.

In some embodiments, inoculant compositions of the present disclosure comprise at least one nonionic surfactant. According to some embodiments, the inoculant composition comprises at least one water insoluble nonionic surfactant and at least one water soluble nonionic surfactant. In some embodiments, inoculant compositions of the present disclosure comprise a combination of nonionic surfactants having hydrocarbon chains of substantially the same length.

In some embodiments, inoculant compositions of the present disclosure comprise one or more zwitterionic surfactants. According to some embodiments, the inoculant composition comprises one or more betaines and/or one or more sultaines, optionally one or more zwitterionic surfactants selected from the group consisting of 3-[(3-Cholamidopropyl)dimethylammonio]-1-propanesulfonate, cocamidopropyl betaine, cocamidopropyl hydroxysultaine, phosphatidylserine, phosphatidylethanolamine, phosphatidylcholine and/or one or more sphingomyelins.

In some embodiments, inoculant compositions of the present disclosure comprise one or more soaps and/or organosilicone surfactants. According to some embodiments, the inoculant composition comprises one or more alkali metal salts of fatty acids.

In some embodiments, inoculant compositions of the present disclosure comprise one or more wetting agents. According to some embodiments, the inoculant composition comprises one or more naphthalene sulfonates, optionally one or more alkyl naphthalene sulfonates (e.g., sodium alkyl naphthalene sulfonate), one or more isopropyl naphthalene sulfonates (e.g., sodium isopropyl naphthalene sulfonate) and/or one or more butyl naphthalene sulfonates (e.g., sodium n-butyl naphthalene sulfonate).

Inoculant compositions of the present disclosure may comprise any suitable drying agent(s), including, but not limited to, drying powders. Non-limiting examples of drying agents include AEROSIL® hydrophobic fumed silica powders (Evonik Corporation, Parsippany, NJ), BENTOLITE® powders (BYK-Chemie GmbH, Wesel, Germany), INCOTEC® powders (INCOTEC Inc., Salinas, CA), SIPERNAT® silica powders (Evonik Corporation, Parsippany, NJ) and combinations thereof. Additional examples of drying agents may be found in BURGES, FORMULATION OF MICROBIAL BIOPESTICIDES: BENEFICIAL MICROORGANISMS, NEMATODES AND SEED TREATMENTS (Springer Science & Business Media) (2012). In some embodiments, inoculant compositions of the present disclosure comprise calcium stearate, clay (e.g., attapulgite clay, montmorillonite clay), graphite, magnesium stearate, magnesium sulfate, powdered milk, silica (e.g., fumed silica, hydrophobically-coated silica, precipitated silica), soy lecithin and/or talc.

Inoculant compositions of the present disclosure may comprise any suitable anti-freezing agent(s), including, but not limited to, ethylene glycol, glycerin, propylene glycol and urea.

Inoculant compositions of the present disclosure may comprise any seed flowability agent to improve the lubricity of the treated seeds. The flowability agent may comprise one or more liquid lubricants, solid lubricants, liquid emulsions, or suspensions of solid lubricants. Non-limiting examples of flowability agents include, for example, lubricants such as fats and oils, natural and synthetic waxes, graphite, talc, fluoropolymers (e.g., polytetrafluoroethylene), and solid lubricants such as molybdenum disulfide and tungsten disulfide. In some instances, the flowability agent comprises a wax material. Non-limiting examples of wax materials that can be incorporated into the liquid seed treatment composition include plant and animal-derived waxes such as carnauba wax, candelilla wax, ouricury wax, beeswax, spermaceti, and petroleum derived waxes, such as paraffin wax. For example, in some instances, the flowability agent comprises carnauba wax. In some instances, the flowability agent comprises an oil. For example, the flowability agent may comprise soybean oil. Non-limiting examples of commercially available wax materials suitable for use as flowability agents include AQUAKLEAN 418 supplied by Micro Powders, Inc. (an anionic aqueous emulsion comprising extra light carnauba wax at 35% solids content).

Inoculant compositions of the present disclosure may comprise any suitable safener(s), including, but not limited to, napthalic anhydride.

Inoculant compositions of the present disclosure may comprise any suitable pH buffer(s), including, but not limited to, potassium phosphate monobasic and potassium phosphate dibasic. In some embodiments, the inoculant composition comprises one or more pH buffers selected to provide a composition having a pH of less than 10, typically from about 4.5 to about 9.5, from about 6 to about 8, or about 7.

Inoculant compositions of the present disclosure may comprise any suitable anti-settling agent(s), including, but not limited to, polyvinyl acetate, polyvinyl alcohols with different degrees of hydrolysis, polyvinylpyrrolidones, polyacrylates, acrylate-, polyol- or polyester-based paint system binders which are soluble or dispersible in water, moreover copolymers of two or more monomers such as acrylic acid, methacrylic acid, itaconic acid, maleic acid, fumaric acid, maleic anhydride, vinylpyrrolidone, ethylenically unsaturated monomers such as ethylene, butadiene, isoprene, chloroprene, styrene, divinylbenzene, ot-methylstyrene or p-methylstyrene, further vinyl halides such as vinyl chloride and vinylidene chloride, additionally vinyl esters such as vinyl acetate, vinyl propionate or vinyl stearate, moreover vinyl methyl ketone or esters of acrylic acid or methacrylic acid with monohydric alcohols or polyols such as methyl acrylate, methyl methacrylate, ethyl acrylate, ethylene methacrylate, lauryl acrylate, lauryl methacrylate, decyl acrylate, N,N-dimethylamino-ethyl methacrylate, 2-hydroxyethyl methacrylate, 2-hydroxypropyl methacrylate or glycidyl methacrylate, furthermore diethyl esters or monoesters of unsaturated dicarboxylic acids, furthermore (meth)acrylamido-N-methylol methyl ether, amides or nitriles such as acrylamide, methacrylamide, N-methylol(meth)acrylamide, acrylonitrile, methacrylonitrile, and also N-substituted maleiraides and ethers such as vinyl butyl ether, vinyl isobutyl ether or vinyl phenyl ether, and combinations thereof.

Inoculant compositions of the present disclosure may comprise any suitable adhesive(s), including, but not limited to, adhesive compositions comprising, consisting essentially of or consisting of one or more disaccharides (e.g. maltose), gums (e.g., cellulose gum, guar gum, gum arabic, gum combretum, xantham gum), maltodextrins (e.g., one or more maltodextrins (each and/or collectively) having a DEV of about 10 to about 20), monosaccharides, oils (e.g., mineral oil, olive oil, peanut oil, soybean oil and/or sunflower oil) and/or oligosaccharides.

Inoculant compositions of the present disclosure may comprise any suitable effect pigment(s). Effect pigments, which are sometimes also referred to in the art as "pearl pigments," are a class of materials that provide reflectivity, shine, and/or a pearlescent effect when applied as a coating. In some instances, the effect pigment is in the form of a powder comprising a substrate material and a metal oxide coating. For example, the effect pigment may comprise a substrate material including but not limited to talc, silicate materials (e.g., mica), clay minerals, calcium carbonate, kaolin, phlogopite, alumina, and similar substances. In some instances, the substrate material comprises a hydrophilic material. The substrate material may be coated with a semi-transparent layer of a metal oxide, including but not limited to titanium dioxide, iron oxide, chromium oxide, or zirconium oxide. Alternatively, in some instances, the effect pigment comprises metal powder or metal flakes. The metal powder or metal flakes may comprise a metal including, but not limited to aluminum, copper, silver, or bronze. In some instances, the effect pigment comprises a silicate based substrate. Non-limiting examples of particulate silicates that can be incorporated into the dry powder coating include mica coated with titanium dioxide (e.g., SUNMICA FINE WHITE 2800102, which is commercially available from Sun Chemical Corp.). Other non-limiting examples of commercially available effect pigments that can be incorporated into the dry powder include MAGNA PEARL, LUMINA and MEARLIN pigments from BASF Corporation; PHIBRO PEARL from PhibroChem; and IRIDESIUM 120 from Aakash Chemicals. In some instances, the dry powder has a mean particle size of from about 1 to about 25 microns.

Inoculant compositions of the present disclosure may comprise any suitable growth medium suitable for culturing one or more of the microorganisms in the inoculant composition. For example, in some embodiments, inoculant compositions of the present disclosure comprise Czapek-Dox medium, glycerol yeast extract, mannitol yeast extract, potato dextrose broth and/or YEM media.

Carriers, stabilizing compounds, biostimulants, microbial extracts, nutrients, pest attractants and/or feeding stimulants, pesticides, plant signal molecules, dispersants, drying agents, safeners, flowability agents, anti-settling agents, buffers, adhesives, etc. may be incorporated into inoculant compositions of the present disclosure in any suitable amount(s)/concentration(s). The absolute value of the amount/concentration that is/are sufficient to cause the desired effect(s) may be affected by factors such as the type, size and volume of material to which the composition will be applied, the type(s) of microorganisms in the composition, the number of microorganisms in the composition, the stability of the microorganisms in the composition and storage conditions (e.g., temperature, relative humidity, duration). Those skilled in the art will understand how to select effective amounts/concentrations/combinations using routine dose-response experiments. Guidance for the selection of appropriate amounts/concentrations/combinations can be found, for example, in International Patent Publication Nos. WO2017/044473, WO2017/044545, WO2017/116837, WO2017/116846, WO2017/210163, WO2017/210166, WO2018/118740, WO2018/175681, WO2018/183491, WO2018/218008, WO2018/218016 and WO2018/218035.

In some embodiments, inoculant compositions of the present disclosure comprise one or more carriers in an amount/concentration of about 1 to about 99% or more (by weight, based upon the total weight of the inoculant composition). For example, inoculant compositions of the present disclosure may comprise about 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98 or 99% (by weight) of one or more non-aqueous carriers.

In some embodiments, inoculant compositions of the present disclosure comprise one or more stabilizing compounds in an amount/concentration of about 0.0001 to about 95% or more (by weight, based upon the total of the inoculant composition). For example, inoculant compositions of the present disclosure may comprise about 0.0001 to about 0.001, about 0.001 to about 1%, about 0.25 to about 5%, about 1 to about 10%, about 5 to about 25%, about 10% to about 30%, about 20% to about 40%, about 25% to about 50%, about 30 to about 60%, about 50 to about 75%, or about 75 to about 95% (by weight), optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95%, of one or more maltodextrins, monosaccharides, disaccharides, sugar alcohols, humic acids, betaines, prolines, sarcosines, peptones, oxidation control components, hygroscopic polymers and/or UV protectants.

In some embodiments, inoculant compositions of the present disclosure comprise one or more stabilizing compounds at a concentration of about $1\times10^{-20}$ M to about $1\times10^{-1}$ M. For example, inoculant compositions of the present disclosure may comprise about $1\times10^{-15}$ M to about $1\times10^{-10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M, optionally about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more, of one or more maltodextrins, monosaccharides, disaccharides, sugar alcohols, humic acids, betaines, prolines, sarcosines, peptones, oxidation control components, hygroscopic polymers and/or UV protectants.

In some embodiments, inoculant compositions of the present disclosure comprise one or more monosaccharides in an amount/concentration of about 0.005 to about 50% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 10, 15, 20, 25% (by weight) of one or more monosaccharides (e.g., arabinose, fructose and/or glucose). In some embodiments, one or more monosaccharides is/are present in a concentration ranging from about $1\times10^{-20}$ M to about $1\times10^{-1}$ M. For example, one or more monosaccharides may be included at a concentration of about/at least/less than $1\times10^{-20}$ M, $1\times10^{-19}$M, $1\times10^{-18}$ M, $1\times10^{-17}$ M, $1\times10^{-16}$M, $1\times10^{-15}$ M, $1\times10^{-14}$M, $1\times10^{-13}$ M, $1\times10^{-12}$ M, $1\times10^{-11}$M, $1\times10^{-10}$ M.

In some embodiments, inoculant compositions of the present disclosure comprise one or more disaccharides in an amount/concentration of about 0.005 to about 50% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 10, 15, 20, 25% (by weight) of one or more disaccharides (e.g., maltose, sucrose and/or trehalose). In some embodiments, one or more disaccharides is/are present in a concentration ranging from about $1\times10^{-20}$ M to about $1\times10^{-1}$ M. For example, one or more disaccharides may be included at a concentration of about/at least/less than $1\times10^{-20}$ M, $1\times10^{-19}$ M, $1\times10^{-18}$ M, $1\times10^{-17}$M, $1\times10^{-16}$M, $1\times10^{-15}$ M, $1\times10^{-14}$ M, $1\times10^{-13}$ M, $1\times10^{-12}$M, $1\times10^{-11}$M, $1\times10^{-10}$ M.

In some embodiments, inoculant compositions of the present disclosure comprise one or more maltodextrins in an amount/concentration of about 0.001 to about 95% or more (by weight) of the inoculant composition. In some embodiments, the maltodextrin(s) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more maltodextrins (e.g., one or more maltodextrins (each and/or collectively) having a DEV value of about 15 to about 20).

In some embodiments, inoculant compositions of the present disclosure comprise one or more sugar alcohols in an amount/concentration of about 0.001 to about 95% or more (by weight) of the inoculant composition. In some embodiments, the sugar alcohol(s) (e.g., arabitol, mannitol, sorbitol and/or xylitol) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more sugar alcohols (e.g., arabitol, mannitol, sorbitol and/or xylitol).

In some embodiments, inoculant compositions of the present disclosure comprise one or more humic acids in an amount/concentration of about 0.001 to about 95% or more (by weight) of the inoculant composition. In some embodiments, the humic acid(s) (e.g., potassium humate) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more humic acids (e.g., potassium humate and/or sodium humate).

In some embodiments, inoculant compositions of the present disclosure comprise one or more UV protectants in an amount/concentration of about 0.0001 to about 5% or more (by weight) of the inoculant composition. In some embodiments, the UV protectant(s) (e.g., calcium lignosulfate and/or sodium lignosulfate) comprise(s) about 0.0001 to about 0.001, about 0.001 to about 1%, about 0.25 to about 5%, (by weight) of the inoculant composition. For example, inoculant compositions of the present disclosure may comprise about/at least/less than 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more (by weight) of one or more UV protectants (e.g., calcium lignosulfate and/or sodium lignosulfate).

In some embodiments, inoculant compositions of the present disclosure comprise one or more oxidation control components in an amount/concentration of about 0.0001 to about 5% or more (by weight) of the composition. For example, inoculant compositions of the present disclosure may comprise about/at least/less than 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% of one or more oxidation control components. In some embodiments, the amount/concentration of oxidation control components is about 0.005 to about 2% (by weight) of the composition. In some embodiments, the oxidation control component(s) is/are present in a concentration ranging from about $1\times10^{-20}$ M to about $1\times10^{-1}$ M. For example, one or more oxidation control components may be added at a concentration of about/at least/less than $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M. In some embodiments, inoculant compositions of the present disclosure comprise one or more commercial antioxidants used in accordance with the manufacturer's recommended amounts/concentrations. In some embodiments, inoculant compositions of the present disclosure comprise one or more commercial oxygen scavengers used in accordance with the manufacturer's recommended amounts/concentrations.

In some embodiments, inoculant compositions of the present disclosure comprise one or more stabilizing compounds in an amount/concentration sufficient to ensure strains of the present disclosure remain viable following storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more fora period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, inoculant compositions of the present disclosure comprise one or more stabilizing compounds in an amount/concentration sufficient to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of strains of the present disclosure remain viable following storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, inoculant compositions of the present disclosure comprise one or more stabilizing compounds in an amount/concentration sufficient to ensure at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$ or more colony-forming units of strains of the present disclosure remain viable per gram and/or milliliter of inoculant composition following storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed); application to plant propagation material and desiccation by about 5, 10, 15, 20, 25, 30, 35, 40, 45, 50, 55, 60, 65, 70, 75, 80, 85, 90, 95% or more; application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application; foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, inoculant compositions of the present disclosure comprise one or more stabilizing compounds in an amount/concentration sufficient to ensure the deliquescence relative humidity (DRH) of the inoculant composition is less than 5, 10, 15, 20, 25, 30, 35, 40, 45, 50, 55, 60, 65, 70, 75, 80, 85 or 90 at the temperature(s) at which the composition is to be stored (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C.).

In some embodiments, inoculant compositions of the present disclosure comprise two or more stabilizing compounds that synergistically enhance the stability and/or survival of strains of the present disclosure remain.

Stabilizing compounds may be incorporated into inoculant compositions of the present disclosure in any suitable ratio(s).

In some embodiments, inoculant compositions of the present disclosure comprise one or more maltodextrins and one or more monosaccharides, disaccharides, sugar alcohols and/or humic acids in a maltodextrin:(monosaccharide, disaccharide, sugar alcohol and/or humic acid) ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5. For example, inoculant compositions of the present disclosure may comprise one or more maltodextrins (e.g., one or more maltodextrins (each and/or collectively) having a DEV of about 15 to about 20) and one or more sugar alcohols (e.g., sorbitol and/or xylitol) and/or humic acids (e.g., potassium humate) in a maltodextrin:(sugar alcohol/humic acid) ratio of about 5:95, about 15:85, about 25:75 or about 50:50.

In some embodiments, inoculant compositions of the present disclosure comprise one or more biostimulants in an amount/concentration of about 0.0001 to about 5% or more (by weight) of the inoculant composition. In some embodiments, the biostimulant(s) (e.g., glycine and/or seaweed extract) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more biostimulants (e.g., glycine and/or seaweed extract).

In some embodiments, inoculant compositions of the present disclosure comprise one or more microbial extracts in an amount/concentration of about 0.0001 to about 5% or more (by weight) of the inoculant composition. In some embodiments, the microbial extract(s) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more microbial extracts.

In some embodiments, inoculant compositions of the present disclosure comprise one or more nutrients in an amount/concentration of about 0.0001 to about 5% or more (by weight) of the inoculant composition. In some embodiments, the nutrient(s) (e.g., phosphorous, boron, chlorine, copper, iron, manganese, molybdenum and/or zinc) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more the nutrients (e.g., phosphorous, boron, chlorine, copper, iron, manganese, molybdenum and/or zinc).

In some embodiments, inoculant compositions of the present disclosure comprise one or more pest attractant(s) and/or feeding stimulant(s) in an amount/concentration of about 0.0001 to about 5% or more (by weight) of the inoculant composition. In some embodiments, the pest attractant(s) and/or feeding stimulant(s) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more pest attractants and/or feeding stimulants.

In some embodiments, inoculant compositions of the present disclosure comprise one or more LCOs at a concentration of about $1 \times 10^{-15}$ M to about $1 \times 10^{-10}$ M, about $1 \times 10^{-14}$ M to about $1 \times 10^{-8}$ M, about $1 \times 10^{-14}$ M to about $1 \times 10^{-6}$ M, about $1 \times 10^{-12}$ M to about $1 \times 10^{-8}$ M, about $1 \times 10^{-12}$ M to about $1 \times 10^{-6}$ M, about $1 \times 10^{-10}$ M to about $1 \times 10^{-6}$ M, or about $1 \times 10^{-8}$ M to about $1 \times 10^{-2}$ M. For example, inoculant compositions of the present disclosure may comprise about $1 \times 10^{-20}$ M, $1 \times 10^{-19}$ M, $1 \times 10^{-18}$ M, $1 \times 10^{-17}$ M, $1 \times 10^{-16}$ M, $1 \times 10^{-15}$ M, $1 \times 10^{-14}$ M, $1 \times 10^{-13}$ M, $1 \times 10^{-12}$ M, $1 \times 10^{-11}$ M, $1 \times 10^{-10}$ M, $1 \times 10^{-9}$ M, $1 \times 10^{-8}$ M, $1 \times 10^{-7}$ M, $1 \times 10^{-6}$ M, $1 \times 10^{-5}$ M, $1 \times 10^{-4}$ M, $1 \times 10^{-3}$ M, $1 \times 10^{-2}$ M, $1 \times 10^{-1}$ M or more of one or more LCOs (e.g., one, two, three, four or more of the LCOs set forth as structures V-XXXIII above).

In some embodiments, inoculant compositions of the present disclosure comprise one or more chitin oligomers at a concentration of about $1 \times 10^{-15}$ M to about $1 \times 10^{-10}$ M, about $1 \times 10^{-14}$ M to about $1 \times 10^{-8}$ M, about $1 \times 10^{-14}$ M to about $1 \times 10^{-6}$ M, about $1 \times 10^{-12}$ M to about $1 \times 10^{-8}$ M, about $1 \times 10^{-12}$ M to about $1 \times 10^{-6}$ M, about $1 \times 10^{-10}$ M to about $1 \times 10^{-6}$ M, or about $1 \times 10^{-8}$ M to about $1 \times 10^{-2}$ M. For example, inoculant compositions of the present disclosure may comprise about $1 \times 10^{-20}$ M, $1 \times 10^{-19}$ M, $1 \times 10^{-18}$ M, $1 \times 10^{-17}$ M, $1 \times 10^{-16}$ M, $1 \times 10^{-15}$ M, $1 \times 10^{-14}$ M, $1 \times 10^{-13}$ M, $1 \times 10^{-12}$ M, $1 \times 10^{-11}$ M, $1 \times 10^{-10}$ M, $1 \times 10^{-9}$ M, $1 \times 10^{-8}$ M, $1 \times 10^{-7}$ M, $1 \times 10^{-6}$ M, $1 \times 10^{-5}$ M, $1 \times 10^{-4}$ M, $1 \times 10^{-3}$ M, $1 \times 10^{-2}$ M, $1 \times 10^{-1}$ M or more of one or more chitin oligomers (e.g., one, two, three, four or more of the chitin oligomers set forth as structures XXXVI-LXXXIII above).

In some embodiments, inoculant compositions of the present disclosure comprise one or more chitosan oligomers at a concentration of about $1 \times 10^{-15}$ M to about $1 \times 10^{-10}$ M, about $1 \times 10^{-14}$ M to about $1 \times 10^{-8}$ M, about $1 \times 10^{-14}$ M to about $1 \times 10^{-6}$ M, about $1 \times 10^{-12}$ M to about $1 \times 10^{-8}$ M, about $1 \times 10^{-12}$ M to about $1 \times 10^{-6}$ M, about $1 \times 10^{-10}$ M to about $1 \times 10^{-6}$ M, or about $1 \times 10^{-8}$ M to about $1 \times 10^{-2}$ M. For example, inoculant compositions of the present disclosure may comprise about $1 \times 10^{-20}$ M, $1 \times 10^{-19}$ M, $1 \times 10^{-18}$ M, $1 \times 10^{-17}$ M, $1 \times 10^{-16}$ M, $1 \times 10^{-15}$ M, $1 \times 10^{-14}$ M, $1 \times 10^{-13}$ M, $1 \times 10^{-12}$ M, $1 \times 10^{-11}$ M, $1 \times 10^{-10}$ M, $1 \times 10^{-9}$ M, $1 \times 10^{-8}$ M, $1 \times 10^{-7}$ M, $1 \times 10^{-6}$ M, $1 \times 10^{-5}$ M, $1 \times 10^{-4}$ M, $1 \times 10^{-3}$ M, $1 \times 10^{-2}$ M, $1 \times 10^{-1}$ M or more of one or more chitosan oligomers (e.g., one, two, three, four or more of the oligosaccharides set forth as structures XXXVI-LXXXIII above in a deacetylated form).

In some embodiments, inoculant compositions of the present disclosure comprise one or more chitins at a concentration of about $1 \times 10^{-15}$ M to about $1 \times 10^{-10}$ M, about $1 \times 10^{-14}$ M to about $1 \times 10^{-8}$ M, about $1 \times 10^{-14}$ M to about $1 \times 10^{-6}$ M, about $1 \times 10^{-12}$ M to about $1 \times 10^{-8}$ M, about $1 \times 10^{-12}$ M to about $1 \times 10^{-6}$ M, about $1 \times 10^{-10}$ M to about $1 \times 10^{-6}$ M, or about $1 \times 10^{-8}$ M to about $1 \times 10^{-2}$ M. For example, inoculant compositions of the present disclosure may comprise about $1 \times 10^{-20}$ M, $1 \times 10^{-19}$ M, $1 \times 10^{-18}$ M, $1 \times 10^{-17}$ M, $1 \times 10^{-16}$ M, $1 \times 10^{-15}$ M, $1 \times 10^{-14}$ M, $1 \times 10^{-13}$ M, $1 \times 10^{-12}$ M, $1 \times 10^{-11}$ M, $1 \times 10^{-10}$ M, $1 \times 10^{-9}$ M, $1 \times 10^{-8}$ M, $1 \times 10^{-7}$ M, $1 \times 10^{-6}$ M, $1 \times 10^{-5}$ M, $1 \times 10^{-4}$ M, $1 \times 10^{-3}$ M, $1 \times 10^{-2}$ M, $1 \times 10^{-1}$ M or more of one or more chitins.

In some embodiments, inoculant compositions of the present disclosure comprise one or more chitosans at a concentration of about $1 \times 10^{-15}$ M to about $1 \times 10^{-10}$ M, about $1 \times 10^{-14}$ M to about $1 \times 10^{-8}$ M, about $1 \times 10^{-14}$ M to about $1 \times 10^{-6}$ M, about $1 \times 10^{-12}$ M to about $1 \times 10^{-8}$ M, about $1 \times 10^{-12}$ M to about $1 \times 10^{-6}$ M, about $1 \times 10^{-10}$ M to about $1 \times 10^{-6}$ M, or about $1 \times 10^{-8}$ M to about $1 \times 10^{-12}$ M. For example, inoculant compositions of the present disclosure may comprise about $1 \times 10^{-20}$ M, $1 \times 10^{-19}$ M, $1 \times 10^{-18}$ M, $1 \times 10^{-17}$ M, $1 \times 10^{-16}$ M, $1 \times 10^{-15}$ M, $1 \times 10^{-14}$ M, $1 \times 10^{-13}$ M, $1 \times 10^{-12}$ M, $1 \times 10^{-11}$ M, $1 \times 10^{-10}$ M, $1 \times 10^{-9}$ M, $1 \times 10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more of one or more chitosans.

In some embodiments, inoculant compositions of the present disclosure comprise one or more dispersants in an amount/concentration of about 0.001 to about 25% or more (by weight) of the inoculant composition. In some embodiments, the dispersant(s) comprise(s) 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9 or 10 to about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20% or more (by weight) of one or more dispersants (e.g., one or more surfactants and/or wetting agents).

In some embodiments, inoculant compositions of the present disclosure comprise one or more drying agents in an amount/concentration of about 0.001 to about 95% or more (by weight) of the inoculant composition. In some embodiments, the drying agent(s) comprise(s) about) 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9 or 10 to about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more drying agents (e.g., lecithin and/or talc).

In some embodiments, the inoculant compositions of the present disclosure comprise about 0.5 to about 10 grams of drying powder per liter of inoculant composition. For example, inoculant compositions of the present disclosure may comprise about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder per liter of inoculant composition.

In some embodiments, inoculant compositions of the present disclosure comprise one or more buffers in an amount/concentration of about 0.0001 to about 5% or more (by weight) of the inoculant composition. In some embodiments, the buffer(s) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more buffers (e.g., potassium phosphate monobasic and/or potassium phosphate dibasic).

In some embodiments, inoculant compositions of the present disclosure comprise one or more commercial carriers, antioxidants, oxygen scavengers, hygroscopic polymers, UV protectants, biostimulants, microbial extracts, nutrients, pest attractants and/or feeding stimulants, pesticides, plant signal molecules, disperants, drying agents, anti-freezing agents, buffers and/or adhesives used in accordance with the manufacturer's recommended amounts/concentrations.

In some embodiments, strains of the present disclosure are the only microbial strains in inoculant compositions of the present disclosure.

In some embodiments, inoculant compositions of the present disclosure comprise one or more microorganisms in addition to strains of the present disclosure. Any suitable microorganism(s) may be added, including, but not limited to, agriculturally beneficial microorganisms such as diazotrophs (e.g., symbiotic diazotrophs), phosphate-solubilizing microorganisms, mycorrhizal fungi and biopesticides. In some embodiments, inoculant compositions of the present disclosure comprise one or more microorganisms selected from the genera and species listed in Appendix A. Selection of additional microbes (if any) will depend on the intended application(s).

Non-limiting examples of bacteria that may be included in inoculant compositions of the present disclosure include *Azospirillum brasilense* INTA Az-39, *Bacillus amyloliquefaciens* D747, *Bacillus amyloliquefaciens* NRRL B 50349, *Bacillus amyloliquefaciens* TJ1000, *Bacillus amyloliquefaciens* FZB24, *Bacillus amyloliquefaciens* FZB42, *Bacillus amyloliquefaciens* IN937a, *Bacillus amyloliquefaciens* IT-45, *Bacillus amyloliquefaciens* TJ1000, *Bacillus amyloliquefaciens* MB1600, *Bacillus amyloliquefaciens* BS27 (deposited as NRRL B-5015), *Bacillus amyloliquefaciens* BS2084 (deposited as NRRL B-50013), *Bacillus amyloliquefaciens* 15AP4 (deposited as ATCC PTA-6507), *Bacillus amyloliquefaciens* 3AP4 (deposited as ATCC PTA-6506), *Bacillus amyloliquefaciens* LSSA01 (deposited as NRRL B-50104), *Bacillus amyloliquefaciens* ABP278 (deposited as NRRL B-50634), *Bacillus amyloliquefaciens* 1013 (deposited as NRRL B-50509), *Bacillus amyloliquefaciens* 918 (deposited as NRRL B-50508), *Bacillus amyloliquefaciens* 22CP1 (deposited as ATCC PTA-6508) and *Bacillus amyloliquefaciens* BS18 (deposited as NRRL B-50633), *Bacillus cereus* 1-1562, *Bacillus firmus* 1-1582, *Bacillus lichenformis* BA842 (deposited as NRRL B-50516), *Bacillus lichenformis* BL21 (deposited as NRRL B-50134), *Bacillus mycoides* NRRL B-21664, *Bacillus pumilus* NRRL B 21662, *Bacillus pumilus* NRRL B-30087, *Bacillus pumilus* ATCC 55608, *Bacillus pumilus* ATCC 55609, *Bacillus pumilus* GB34, *Bacillus pumilus* KFP9F, *Bacillus pumilus* QST 2808, *Bacillus subtilis* ATCC 55078, *Bacillus subtilis* ATCC 55079, *Bacillus subtilis* MBI 600, *Bacillus subtilis* NRRL B-21661, *Bacillus subtilis* NRRL B-21665, *Bacillus subtilis* CX-9060, *Bacillus subtilis* GB03, *Bacillus subtilis* GB07, *Bacillus subtilis* QST-713, *Bacillus subtilis* FZB24, *Bacillus subtilis* D747, *Bacillus subtilis* 3BP5 (deposited as NRRL B-50510), *Bacillus thuringiensis*

ATCC 13367, *Bacillus thuringiensis* GC-91, *Bacillus thuringiensis* NRRL B-21619, *Bacillus thuringiensis* ABTS-1857, *Bacillus thuringiensis* SAN 401 I, *Bacillus thuringiensis* ABG-6305, *Bacillus thuringiensis* ABG-6346, *Bacillus thuringiensis* AM65-52, *Bacillus thuringiensis* SA-12, *Bacillus thuringiensis* SB4, *Bacillus thuringiensis* ABTS-351, *Bacillus thuringiensis* HD-1, *Bacillus thuringiensis* EG 2348, *Bacillus thuringiensis* EG 7826, *Bacillus thuringiensis* EG 7841, *Bacillus thuringiensis* DSM 2803, *Bacillus thuringiensis* NB-125, *Bacillus thuringiensis* NB-176, BRADY, *Mesorhizobium huakii* LL32, *Pseudomonas jessenii* PS06, *Rhizobium leguminosarum* 162BB1, *Rhizobium leguminosarum* 162P17, *Rhizobium leguminosarum* 175G10b, *Rhizobium leguminosarum* D36, *Rhizobium leguminosarum SO*12A-2 (IDAC 080305-01), *Rhizobium loti* 95C11, *Rhizobium loti* 95C14, *Sinorhizobium fredii* CCBAU114, *Sinorhizobium fredii* USDA 205, *Sinorhizobium meliloti* 102F34a, *Sinorhizobium meliloti* 102F51a, *Sinorhizobium meliloti* 102F77b, *Sinorhizobium meliloti* B401, *Yersinia entomophaga* O82KB8 and combinations thereof, as well as microorganisms having at least at least 75, 80, 85, 90, 95, 96, 97, 97.5, 98, 98.5, 99, 99.5, 99.6, 99.7, 99.8, 99.9% or more identical to any of the aforementioned strains on the basis of 16S rDNA sequence identity.

Non-limiting examples of fungi that may be included in inoculant compositions of the present disclosure include *Gliocladium virens* ATCC 52045, *Gliocladium virens* GL-21, *Glomus intraradices* RTI-801, *Metarhizium anisopliae* F52, PENT, *Trichoderma asperellum* SKT-1, *Trichoderma asperellum* ICC 012, *Trichoderma atroviride* LC52, *Trichoderma atroviride* CNCM 1-1237, *Trichoderma fertile* JM41R, *Trichoderma gamsii* ICC 080, *Trichoderma hamatum* ATCC 52198, *Trichoderma harzianum* ATCC 52445, *Trichoderma harzianum* KRL-AG2, *Trichoderma harzianum* T-22, *Trichoderma harzianum* TH-35, *Trichoderma harzianum* T-39, *Trichoderma harzianum* ICC012, *Trichoderma reesi* ATCC 28217, *Trichoderma virens* ATCC 58678, *Trichoderma virens* G1-3, *Trichoderma virens* GL-21, *Trichoderma virens* G-41, *Trichoderma viridae* ATCC 52440, *Trichoderma viridae* ICC080, *Trichoderma viridae* TV1 and combinations thereof, as well as microorganisms having at least at least 75, 80, 85, 90, 95, 96, 97, 97.5. 98, 98.5, 99, 99.5, 99.6, 99.7, 99.8, 99.9% or more identical to any of the aforementioned strains on the basis of internal transcribed spacer (ITS) and/or cytochrome c oxidase (CO1) sequence identity.

Non-limiting examples of mycorrhizal fungi that may be included in inoculant compositions of the present disclosure include mycorrhizal strains such as *Gigaspora margarita, Glomus aggregatum, Glomus brasilianum, Glomus clarum, Glomus deserticola, Glomus etunicatum, Glomus intraradices, Glomus monosporum, Glomus mosseae, Laccaria bicolor, Laccaria laccata, Paraglomus brazilianum, Pisolithus tinctorius, Rhizopogon amylopogon, Rhizopogon fulvigleba, Rhizopogon luteolus, Rhizopogon villosuli, Scleroderma cepa* and *Scleroderma citrinum* and combinations thereof.

Additional examples of microorganisms that may be added to inoculant compositions of the present disclosure can be found in Appendix A.

Additional microorganisms may be incorporated into inoculant compositions of the present disclosure in any suitable amount(s)/concentration(s). The absolute value of the amount/concentration that is/are sufficient to cause the desired effect(s) may be affected by factors such as the type, size and volume of material to which the composition will be applied, the microorganisms in the composition, the number of microorganisms in the composition, the stability of the microorganisms in the composition and storage conditions (e.g., temperature, relative humidity, duration). Those skilled in the art will understand how to select an effective amount/concentration using routine dose-response experiments. Guidance for the selection of appropriate amounts/concentrations can be found, for example, in International Patent Publication Nos. WO2003/000051, WO2009/015266, WO2010/037228, WO2011/140051, WO2012/135704, WO2013/090884, WO2014/078647, WO2015/069708, WO2017/027821, WO2017/044473, WO2017/044545, WO2017/077104, WO2017/083623, WO2017/116837, WO2017/116846, WO2017/131971, WO2017/205258, WO2017/210163, WO2017/210166, WO2018/118740, WO2018/129016, WO2018/129018, WO2018/175677, WO2018/175681, WO2018/183491, WO2018/218008, WO2018/218016 and WO2018/218035, and in U.S. Patent Publication Nos. 2006/258534, 2011/230345 and 2018/201549.

In some embodiments, one or more additional microorganisms is/are present in an effective amount/concentration for fixing atmospheric nitrogen, solubilizing phosphate, controlling one or more phytopathogenic pests, enhancing stress tolerance and/or enhancing plant growth/yield when the inoculant composition is introduced into a plant growth medium (e.g., a soil).

In some embodiments, one or more additional microorganisms is/are present in an effective amount/concentration for fixing atmospheric nitrogen, solubilizing phosphate, controlling one or more phytopathogenic pests, enhancing stress tolerance and/or enhancing plant growth/yield when the inoculant composition is applied to a plant or plant part.

In some embodiments, one or more additional microorganisms is/are present in an amount ranging from about $1\times10^1$ to about $1\times10^{12}$ colony-forming units (cfu) per gram and/or milliliter of inoculant composition. According to some embodiments, the inoculant composition comprises about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more cfu of one or more additional microorganisms per gram and/or milliliter of inoculant composition (e.g., about $1\times10^4$ to about 1 xo $10^9$ cfu/g of *Bacillus amyloliquefaciens* TJ1000 (also known as 1BE, isolate ATCC BAA-390), BRADY, *Metarhizium anisopliae* F52, PENT, *Trichoderma virens* G1-3, and/or *Yersinia entomophaga* O82KB8). In some embodiments, inoculant compositions of the present disclosure comprise at least $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu of one or more additional microorganisms per gram and/or millilitre of inoculant composition.

In some embodiments, spores from one or more additional microorganism comprise about 0.1 to about 90% (by weight) of the inoculant composition. According to some embodiments, the inoculant composition comprises about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95% or more (by weight) of microbial spores from one or more additional microorganisms (e.g., about 10% *Bacillus amyloliquefaciens* TJ1000, *Metarhizium anisopliae* F52, *Penicillium bilaiae* ATCC 20851, *Penicillium bilaiae* RS7B-SD1 and/or *Trichoderma virens* G1-3 spores). In some embodiments, the amount/concentration of microbial spores from one or more additional microorganisms is about 1 to about 25%, about 5 to about 20%, about 5 to about 15%, about 5 to about 10% or about 8 to about 12% (by weight) of the inoculant composition.

It is to be understood that additional microorganisms in inoculant compositions of the present disclosure may comprise vegetative cells and/or dormant spores. According to some embodiments, at least 1, 5, 10, 15, 20, 25, 30, 35, 40, 45, 50, 55, 60, 65, 70, 75, 80, 85, 90, 95, 96, 97, 98, 99% or more additional microorganism are present in inoculant compositions of the present disclosure as vegetative cells. According to some embodiments, at least 1, 5, 10, 15, 20, 25, 30, 35, 40, 45, 50, 55, 60, 65, 70, 75, 80, 85, 90, 95, 96, 97, 98, 99% or more additional microorganism are present in inoculant compositions of the present disclosure as spores.

Inoculant compositions of the present disclosure may be formulated as any suitable type of composition, including, but not limited to, foliar inoculants, seed coatings and soil inoculants.

In some embodiments, inoculant compositions of the present disclosure are formulated as amorphous solids.

In some embodiments, inoculant compositions of the present disclosure are formulated as amorphous liquids.

In some embodiments, inoculant compositions of the present disclosure are formulated as wettable powders.

In some embodiments, inoculant compositions of the present disclosure are formulated as liquid compositions that are subsequently dried to produce a powder or granuale. For example, in some embodiments, liquid inoculant compositions of the present disclosure are drum dried, evaporation dried, fluidized bed dried, freeze dried, spray dried, spray-freeze dried, tray dried and/or vacuum dried to produce powders/granuales. Such powders/granuales may be further processed using any suitable method(s), including, but not limited to, flocculation, granulation and milling, to achieve a desired particle size or physical format. The precise method(s) and parameters of processing dried powders/granuales that are appropriate in a given situation may be affected by factors such as the desired particle size(s), the type, size and volume of material to which the composition will be applied, the type(s) of microorganisms in the composition, the number of microorganisms in the composition, the stability of the microorganisms in the composition and the storage conditions (e.g., temperature, relative humidity, duration). Those skilled in the art will understand how to select appropriate methods and parameters using routine experiments.

In some embodiments, inoculant compositions of the present disclosure are frozen for cryopreservation. For example, in some embodiments, liquid inoculant compositions of the present disclosure are flash-frozen and stored in a cryopreservation storage unit/facility. The precise method(s) and parameters of freezing and preserving inoculant compositions of the present disclosure that are appropriate in a given situation may be affected by factors such as the type(s) of microorganisms in the composition, the number of microorganisms in the composition, the stability of the microorganisms in the composition and the storage conditions (e.g., temperature, relative humidity, duration). Those skilled in the art will understand how to select appropriate methods and parameters using routine experiments.

Inoculant compositions of the present disclosure may be formulated as aqueous or non-aqueous compositions. In some embodiments, inoculant compositions of the present disclosure comprise no water. In some embodiments, inoculant compositions of the present disclosure comprise a trace amount of water. In some embodiments, inoculant compositions of the present disclosure comprise less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5% water by weight, based upon the total weight of the composition.

In some embodiments, inoculant compositions of the present disclosure are formulated to have a pH of about 4.5 to about 9.5. In some embodiments, inoculant compositions of the present disclosure have a pH of about 6 to about 7.5. In some embodiments, inoculant compositions of the present disclosure have a pH of about 5, 5.5, 6, 6.5, 7, 7.5, 8 or 8.5.

In some embodiments, one or more strains of the present disclosure is incorporated into an ACCELERON®, ACTINOVATE®, CELL-TECH®, JUMPSTART®, MET52®, NEMASTRIKE™, NITRAGIN®, OPTIMIZE®, QUICKROOTS®, TAGTEAM®, or TORQUE® product. Strains of the present disclosure may also be beneficially incorporated into AVAIL®, BAR MAX NORTE, BAR MAX SUR, BIOBOOST®, BIOPOWER, BIOSINC®, COMO PLATINUM, CROP+®, DEFENDR™ DIAMONBRAND®, DYNA-START™, EXCALIBRE-SA™, EXCEED®, EXCELLORATE™, FIRST UP®, FLEXCONNECT™, FORZA™, FUNGI-PHITE®, GRAPH-EX®, GRAPH-EX SA®, GUARD.N®, HEADSUP®, ILEVO®, INTRACEPT™, LAUNCHER™, LEGACY™, MARAUDER®, MASTERFIX L PREMIER, MAXIMIZE™, MEGA-PACK™, MICROAZ-IF LIQUID™, MICROAZ-ST DRY™, MICROSTAR®, MICROSYNC™, MORE THAN MANURE®, NATURALL™, N-CHARGE®, N-DURE™, N-FORCE, N-TAKE™, NODULATOR®, NUE CHARGE G™, NUTRI-GROW®, NUTRIPACTION®, NUTRIPHITE®, NUTRISPHERE-N®, OBVIUS®, PBX™, PONCHO®, PREMAX®, PREMAXR®, PRE-VAIL™, PRE-SIDE CL®, PRESIDE ULTRA®, PRIMACY ALPHA®, PRIMO, PROSURGE™, PULSERHIZO®, RECOVER®, SABREX®, RILEGUM®, RIZOFOS®, RIZOLIQ®, SAFE ZONE™, SEED+™, SIGNUM®, SIMBIOSE®, SOYRHIZO®, SOYSUPERB®, STAMINA®, STATUS®, STERICS®, STIMUCONTROL®, SYSTIVA®, TAKE OFF®, TAKE OFF ST®, TERRAMAX DRY™, TERRAMAX LIQUID-IF, TRIDENT™, TUXEDO®, VAULT®, VERTEX-IF, VIGOR®, VIGOR SEED, VOTIVO®, WUXAL TERIOS and XITEBIO® YIELD+ products.

As noted above, inoculant compositions of the present disclosure may contain a variety of carriers, stabilizers, nutrients, pesticides, plant signal molcules, dispersants, etc. It is to be understood that the components to be included in the inoculant composition and the order in which components are incorporated into the inoculant composition may be chosen or designed to maintain or enhance the dispersion, stability and/or survival of the strains of the present disclosure during storage, distribution, and/or application of the inoculant composition.

It is to be understood that inoculant compositions of the present disclosure are non-naturally occurring compositions. According to some embodiments, the inoculant composition comprises one or more non-naturally occurring components. According to some embodiments, the inoculant composition comprises a non-naturally occurring combination of naturally occurring components.

The present disclosure extends to kits comprising, consisting essentially of, or consisting of two or more containers, each comprising one or more components of an inoculant composition of the present disclosure. For example, one or more strains of the present disclosure and the agriculturally acceptable carrier may be housed in separate containers for long-term storage, then combined prior to applying the inoculant composition to a plant or plant propagation material. Optional constituents, such as stabilizing compounds, pesticides and plant signaling molecules, may be added to either of the two containers or housed in one or more separate containers for long-term storage. In some embodiments, the kit further comprises one or more oxygen scavengers, such as activated carbon, ascorbic acid, iron powder, mixtures of ferrous carbonate and metal halide catalysts, sodium chloride and/or sodium hydrogen carbonate.

The containers may comprise any suitable material(s), including, but not limited to, materials that reduce the amount of light, moisture and/or oxygen that contact the coated plant propagation material when the container is sealed. In some embodiments, the containers comprise, consist essentially of, or consist of a material having light permeability of less than about 1, 2, 3, 4, 5, 6, 7, 8, 9, 10, 15, 20, 25, 30, 35, 40, 45, 50, 55, 60, 65, 70 or 75%. In some embodiments, the containers comprise, consist essentially of, or consist of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 $cm^3/m^2 \cdot day$ (as measured in accordance with ASTM D3985).

In some embodiments, the containers reduce the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

In some embodiments, the containers reduce the amount of ambient moisture that reaches said plant propagation material by about 5, 10, 15, 20, 25, 30, 35, 40, 45, 50, 55, 60, 65, 70, 75, 80, 85, 90, 95 or 100% when sealed.

In some embodiments, the containers reduce the amount of ambient oxygen that reaches said plant propagation material by about 5, 10, 15, 20, 25, 30, 35, 40, 45, 50, 55, 60, 65, 70, 75, 80, 85, 90, 95 or 100% when sealed.

Strains of the present disclosure and inoculant compositions of the present disclosure may be applied to any plant type, including, but not limited to, row crops and vegetables. In some embodiments, strains of the present disclosure and inoculant compositions of the present disclosure are formulated for the treatment of one or more plants selected from the families Amaranthaceae (e.g., chard, spinach, sugar beet, quinoa), Asteraceae (e.g., artichoke, asters, chamomile, chicory, chrysanthemums, dahlias, daisies, echinacea, goldenrod, guayule, lettuce, marigolds, safflower, sunflowers, zinnias), Brassicaceae (e.g., arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, *Arabidopsis thaliana*), Cucurbitaceae (e.g., cantaloupe, cucumber, honeydew, melon, pumpkin, squash (e.g., acorn squash, butternut squash, summer squash), watermelon, zucchini), Fabaceae (e.g., alfalfa, beans, carob, clover, guar, lentils, mesquite, peas, peanuts, soybeans, tamarind, tragacanth, vetch), Malvaceae (e.g., cacao, cotton, durian, hibiscus, kenaf, kola, okra), Poaceae (e.g., bamboo, barley, corn, fonio, lawn grass (e.g., Bahia grass, Bermudagrass, bluegrass, Buffalograss, Centipede grass, Fescue, or *Zoysia*), millet, oats, ornamental grasses, rice, rye, sorghum, sugar cane, triticale, wheat and other cereal crops, Polygonaceae (e.g., buckwheat), Rosaceae (e.g., almonds, apples, apricots, blackberry, blueberry, cherries, peaches, plums, quinces, raspberries, roses, strawberries), Solanaceae (e.g., bell peppers, chili peppers, eggplant, *petunia*, potato, tobacco, tomato) and Vitaceae (e.g., grape). In some embodiments, strains of the present disclosure and inoculant compositions of the present disclosure are formulated for the treatment of one or more plants with which the strain(s) is/are not naturally associated (e.g., one or more plants that does not naturally exist in the geographical location(s) from which the strain(s) was/were isolated). In some embodiments, strains of the present disclosure and inoculant compositions of the present disclosure are formulated for the treatment of one or more acaricide-, fungicide-, gastropodicide-, herbicide-, insecticide-, nematicide-, rodenticide- and/or virucide-resistant plants (e.g., one or more plants resistant to acetolactate synthase inhibitors (e.g., imidazolinone, pryimidinyoxy(thio)benzoates, sulfonylaminocarbonyltriazolinone, sulfonylurea, triazolopyrimidines), bialaphos, glufosinate, glyphosate, hydroxyphenylpyruvatedioxygenase inhibitors and/or phosphinothricin). Non-limiting examples of plants that may be treated with strains of the present disclosure and inoculant compositions of the present disclosure include plants sold under the BOLLGARD DROUGHTGARD®, GENUITY®, RIB COMPLETE®, ROUNDUP READY®, ROUNDUP READY 2 YIELD®, ROUNDUP READY 2 EXTEND™, SMARTSTAX®, VT DOUBLE PRO®, VT TRIPLE PRO®, YIELDGARD®, YIELDGARD VT ROOTWORM/RR2®, YIELDGARD VT TRIPLE® and/or XTENDFLEX™ tradenames.

Strains of the present disclosure and inoculant compositions of the present disclosure may be applied to any part/portion of a plant. In some embodiments, one or more strains of the present disclosure (or an inoculant composition of the present disclosure) is applied to plant propagation materials (e.g., cuttings, rhizomes, seeds and tubers). In some embodiments, one or more strains of the present disclosure (or an inoculant composition of the present disclosure) is applied to the roots of a plant. In some embodiments, one or more strains of the present disclosure (or an inoculant composition of the present disclosure) is applied to the foliage of a plant. In some embodiments, one or more strains of the present disclosure (or an inoculant composition of the present disclosure) is applied to both the roots and the foliage of a plant. In some embodiments, one or more strains of the present disclosure (or an inoculant composition of the present disclosure) is applied to plant propagation materials and to the plants that grow from said plant propagation materials.

Strains of the present disclosure and inoculant compositions of the present disclosure may be applied to any plant growth medium, including, but not limited to, soil.

Strains of the present disclosure and inoculant compositions of the present disclosure may be applied to plants, plant parts and/or plant growth media in any suitable manner, including, but not limited to, on-seed application, in-furrow application and foliar application.

Strains of the present disclosure and inoculant compositions of the present disclosure may be applied using any suitable method(s), including, but not limited to, coating, dripping, dusting, encapsulating, immersing, spraying and soaking. Batch systems, in which predetermined batch sizes of material and inoculant composition are delivered into a mixer, may be employed. Continuous treatment systems, which are calibrated to apply inoculant composition at a predefined rate in proportion to a continuous flow of material, may also be employed.

In some embodiments, one or more strains of the present disclosure (or an inoculant composition of the present disclosure) is applied directly to plant propagation material (e.g., seeds). According to some embodiments, plant propagation materials are soaked in a composition comprising one or more strains of the present disclosure for at least 0.1, 0.2, 0.3, 0.4, 0.5, 0.6, 0.7, 0.8, 0.9, 1, 1.25, 1.5, 1.75, 2, 3, 4, 5, 6, 9, 12, 15, 18, 21, 24, 36, 48 hours. According to some embodiments, plant propagation materials are coated with one or more strains of the present disclosure (or an inoculant composition of the present disclosure). Plant propagation materials may be coated with one or more additional layers (e.g., one or more protective layers that serves to enhance the stability and/or survival of the strain(s) of the present disclosure and/or one or more sequestration layers comprising substances that may reduce the stability and/or survival of strains of the present disclosure if included in same layer strains of the present disclosure). In some embodiments, the coating comprises, consists essentially of, or consists of an inoculant composition of the present disclosure and a drying powder.

In some embodiments, one or more strains of the present disclosure (or an inoculant composition of the present disclosure) is applied directly to a plant growth medium (e.g., a soil). According to some embodiments, one or more strains of the present disclosure (or an inoculant composition of the present disclosure) is applied in the vicinity of a plant propagation material (e.g., a seed). According to some embodiments, one or more strains of the present disclosure (or an inoculant composition of the present disclosure) is applied to the root zone of a plant. According to some embodiments, one or more strains of the present disclosure (or an inoculant composition of the present disclosure) is applied using a drip irrigation system.

In some embodiments, one or more strains of the present disclosure (or an inoculant composition of the present disclosure) is applied directly to plants. According to some embodiments, one or more strains of the present disclosure (or an inoculant composition of the present disclosure) is sprayed and/or sprinkled on the plant(s) to be treated.

In some embodiments, one or more strains of the present disclosure (or an inoculant composition of the present disclosure) is freeze- spray- or spray-freeze-dried and then applied to plants/plant parts. For examples, in some embodiments, an inoculant composition comprising one or more strains of the present disclosure and one or more stabilizing components (e.g., one or more maltodextrins having a DEV of about 15 to about 20) is freeze- spray- or spray-freeze-dried, mixed with a drying powder (e.g., a drying powder comprising calcium stearate, attapulgite clay, montmorillonite clay, graphite, magnesium stearate, silica (e.g., fumed silica, hydrophobically-coated silica and/or precipitated silica) and/or talc), then coated on seed that was been pre-treated with one or more adhesives (e.g., an adhesive composition comprising one or more maltodextrins, one or more mono-, di- or oligosaccharides, one or more peptones, etc.), one or more pesticides and/or one or more plant signal molecules (e.g., one or more LCDs).

Strains of the present disclosure and inoculant compositions of the present disclosure may be applied to plants, plant parts and/or plant growth media in any suitable amount(s)/concentration(s).

In some embodiments, one or more strains of the present disclosure is applied at a rate of about $1\times10^1$ to about $1\times10^{20}$ cfu per kilogram of plant propagation material. According to some embodiments, one or more strains of the present disclosure is applied in an amount sufficient to ensure the plant propagation materials are coated with about/at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of *P. koreensis* NRRL B-67883 per kilogram of plant propagation material. According to some embodiments, one or more strains of the present disclosure is applied in an amount sufficient to ensure that an average of about/at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of *P. koreensis* NRRL B-67883 is applied to each seed.

In some embodiments, one or more strains of the present disclosure is applied at a rate of about $1\times10^1$ to about $1\times10^{20}$ cfu per plant. According to some embodiments, one or more strains of the present disclosure is applied in an amount sufficient to ensure each plant is treated with about/at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of *P. koreensis* NRRL B-67883. According to some embodiments, one or more strains of the present disclosure is applied in an amount sufficient to ensure that an average of about/at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of *P. koreensis* NRRL B-67883 is applied to each plant.

In some embodiments one or more strains of the present disclosure is applied at a rate of about $1\times10^1$ to about $1\times10^{20}$ cfu per acre of treated crops. According to some embodiments, one or more strains of the present disclosure is applied in an amount sufficient to ensure each acre of treated crops is treated with about/at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of *P. koreensis* NRRL B-67883. According to some embodiments, one or more strains of the present disclosure is applied in an amount sufficient to ensure that an average of about/at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of *P. koreensis* NRRL B-67883 is applied to each acre of treated crops.

In some embodiments, one or more strains of the present disclosure is applied at a rate of about $1\times10^1$ to about $1\times10^{20}$ cfu per acre of plant growth media. According to some embodiments, one or more strains of the present disclosure is applied in an amount sufficient to ensure each acre of plant growth media is treated with about/at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of *P. koreensis* NRRL B-67883. According to some embodiments, one or more strains of the present disclosure is applied in an amount sufficient to ensure that an average of about/at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of *P. koreensis* NRRL B-67883 is applied to each acre of plant growth media.

In some embodiments, inoculant compositions of the present disclosure are applied at a rate of about 0.05 to about 100 milliliters and/or grams of inoculant composition per kilogram of plant propagation material. According to some embodiments, one or more inoculant compositions of the present disclosure is/are applied in an amount sufficient to ensure the plant propagation materials are coated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of inoculant compositions per kilogram of plant propagation material. According to some embodiments, one or more inoculant compositions of the present disclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 milliliters and/or grams of inoculant composition is applied to each seed.

In some embodiments, inoculant compositions of the present disclosure are applied at a rate of about 0.5 to about 100 milliliters and/or grams of inoculant composition per plant. According to some embodiments, one or more inoculant compositions of the present disclosure is/are applied in an amount sufficient to ensure each plant is treated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of inoculant composition. According to some embodiments, one or more inoculant compositions of the present disclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 milliliters and/or grams of inoculant composition is applied to each plant.

In some embodiments, inoculant compositions of the present diclosure are applied at a rate of about 0.5 to about 100 milliliters and/or grams of inoculant composition per acre of treated crops. According to some embodiments, one or more inoculant compositions of the present diclosure is/are applied in an amount sufficient to ensure each acre of treated crops is treated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of inoculant composition. According to some embodiments, one or more inoculant compositions of the present disclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 milliliters and/or grams of inoculant composition is applied to each acre of treated crops.

In some embodiments, inoculant compositions of the present disclosure are applied at a rate of about 0.5 to about 100 milliliters and/or grams of inoculant composition per acre of plant growth media. According to some embodiments, one or more inoculant compositions of the present disclosure is/are applied in an amount sufficient to ensure each acre of plant growth media is treated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of inoculant composition. According to some embodiments, one or more inoculant compositions of the present disclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 milliliters and/or grams of inoculant composition is applied to each acre of plant growth media.

In some embodiments, inoculant compositions of the present disclosure are applied in an amount sufficient to ensure the plant propagation materials are coated with about/at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of $P.$ $koreensis$ NRRL B-67883 per kilogram of plant propagation material. According to some embodiments, one or more inoculant compositions of the present disclosure is/are applied in an amount sufficient to ensure that an average of about/at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of $P.$ $koreensis$ NRRL B-67883 is applied to each seed.

In some embodiments, inoculant compositions of the present disclosure are applied in an amount sufficient to ensure each plant is treated with about/at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of $P.$ $koreensis$ NRRL B-67883. According to some embodiments, one or more inoculant compositions of the present disclosure is/are applied in an amount sufficient to ensure that an average of about/at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of $P.$ $koreensis$ NRRL B-67883 is applied to each plant.

In some embodiments, inoculant compositions of the present disclosure are applied in an amount sufficient to ensure each acre of treated crops is treated with about/at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of $P.$ $koreensis$ NRRL B-67883. According to some embodiments, one or more inoculant compositions of the present disclosure is/are applied in an amount sufficient to ensure that an average of about/at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of $P.$ $koreensis$ NRRL B-67883 is applied to each acre of treated crops.

In some embodiments, inoculant compositions of the present disclosure are applied in an amount sufficient to ensure each acre of plant growth media is treated with about/at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of $P.$ $koreensis$ NRRL B-67883. According to some embodiments, one or more inoculant compositions of the present disclosure is/are applied in an amount sufficient to ensure that an average of about/at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cfu of $P.$ $koreensis$ NRRL B-67883 is applied to each acre of plant growth media.

Strains of the present disclosure and inoculant compositions of the present disclosure may be applied to plants, plant parts and/or plant growth media at any time, including, but not limited to, prior to planting, at the time of planting, after planting, prior to germination, at the time of germination, after germination, prior to seedling emergence, at the time of seedling emergence, after seedling emergence, prior to the vegetative stage, during the vegetative stage, after the vegetative stage, prior to the reproductive stage, during the reproductive stage, after the reproductive stage, prior to flowering, at the time of flowering, after flowering, prior to fruiting, at the time of fruiting, after fruiting, prior to ripening, at the time of ripening, and after ripening. In some embodiments, one or more strains of the present disclosure (or an inoculant composition of the present disclosure) is applied to plant propagation materials (e.g., seeds) about/at least 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks prior to planting.

In some embodiments, one or more strains of the present disclosure (or an inoculant composition of the present disclosure) is applied to plant propagation materials (e.g., seeds) at the time of planting.

In some embodiments, one or more strains of the present disclosure (or an inoculant composition of the present disclosure) is applied to plant propagation materials (e.g., seeds) after planting but before germination.

In some embodiments, one or more strains of the present disclosure (or an inoculant composition of the present disclosure) is applied to plants following emergence.

The present disclosure extends to plants and plant parts (e.g., coated plant propagation materials) that have been treated with one or more strains of the present disclosure (or an inoculant composition of the present disclosure), to plants that grow from plant parts (e.g., coated plant propagation materials) that have been treated with one or more strains of the present disclosure (or an inoculant composition of the present disclosure), to plant parts harvested from plants that have been treated with one or more strains of the present disclosure (or an inoculant composition of the present disclosure), to plant parts harvested from plants that grow from plant parts (e.g., coated plant propagation materials) that have been treated with one or more strains of the present disclosure (or an inoculant composition of the present disclosure), to processed products derived from plants that have been treated with one or more strains of the present disclosure (or an inoculant composition of the present disclosure), to processed products derived from plants that grow from plant parts (e.g., coated plant propagation materials) that have been treated with one or more strains of the present disclosure (or an inoculant composition of the present disclosure), to crops comprising a plurality of plants that have been treated with ne or more strains of the present disclosure (or an inoculant composition of the present disclosure), and to crops comprising a plurality of plants that grow from plant parts (e.g., coated plant propagation materials) that have been treated with one or more strains of the present disclosure (or an inoculant composition of the present disclosure).

In some embodiments, the present disclosure provides coated plant propagation materials comprising, consisting essentially of, or consisting of a plant propagation material and a coating that covers at least a portion of the outer surface of the plant propagation material, said coating comprising, consisting essentially of, or consisting of one or more strains of the present disclosure or an inoculant composition of the present disclosure.

In some embodiments, the coating comprises two, three, four, five or more layers. According to some embodiments, the coating comprises an inner layer that contains one or more strains of the present disclosure and one or more outer layers free or substantially free of microorganisms. In some embodiments, the coating comprises an inner layer that is an inoculant composition of the present disclosure and an outer layer that is equivalent to an inoculant composition of the present disclosure except that it does not contain the strain(s) of the present disclosure.

In some embodiments, the coating comprises, consists essentially of, or consists of an inoculant composition of the present disclosure and a drying powder. Drying powders may be applied in any suitable amount(s)/concentration(s). The absolute value of the amount/concentration that is/are sufficient to cause the desired effect(s) may be affected by factors such as the type, size and volume of material to which the composition will be applied, the type(s) of microorganisms in the composition, the number of microorganisms in the composition and the stability of the microorganisms in the composition and storage conditions (e.g., temperature, relative humidity, duration). Those skilled in the art will understand how to select an effective amount/concentration using routine dose-response experiments. Guidance for the selection of appropriate amounts/concentrations can be found, for example, in International Patent Publication Nos. WO2017/044473, WO2017/044545, WO2017/116837, WO2017/116846, WO2017/210163 and WO2017/210166 and in U.S. Provisional Patent Application Nos. 62/296,798; 62/271,857; 62/347,773; 62/343,217; 62/296,784; 62/271,873; 62/347,785; 62/347,794; and 62/347,805. In some embodiments, the drying powder is applied in an amount ranging from about 0.5 to about 10 grams of drying powder per kilogram of plant propagation material. For example, in some embodiments, about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder (e.g., drying powder comprising magnesium stearate, magnesium sulfate, powdered milk, silica, soy lecithin and/or talc) is applied per kilogram of seed. In some embodiments, a drying powder comprising calcium stearate, attapulgite clay, montmorillonite clay, graphite, magnesium stearate, silica (e.g., fumed silica, hydrophobically-coated silica and/or precipitated silica) and/or talc is applied to seeds coated with an inoculant composition of the present disclosure at a rate of about 1, 1.25, 1.5, 1.75, 2, 2.25, 2.5, 2.75, or 3 grams per kilogram of seed.

In some embodiments, the coating completely covers the outer surface of the plant propagation material.

In some embodiments, the average thickness of the coating is at least 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 4, 4.5, 5 µm or more. In some embodiments, the average thickness of the coating is about 1.5 to about 3.0 µm.

The present disclosure extends to kits comprising, consisting essentially of, or consisting of one or more plants and/or plant parts (e.g., coated plant propagation materials) that have been treated with one or more strains of the present disclosure or an inoculant composition of the present disclosure and a container housing the treated plant(s) and/or plant part(s). In some embodiments, the kit further comprises one or more oxygen scavengers, such as activated carbon, ascorbic acid, iron powder, mixtures of ferrous carbonate and metal halide catalysts, sodium chloride and/or sodium hydrogen carbonate.

The container may comprise any suitable material(s), including, but not limited to, materials that reduce the amount of light, moisture and/or oxygen that contact the coated plant propagation material when the container is sealed. In some embodiments, the container comprises, consists essentially of, or consists of a material having light permeability of less than about 1, 2, 3, 4, 5, 6, 7, 8, 9, 10, 15, 20, 25, 30, 35, 40, 45, 50, 55, 60, 65, 70 or 75%. In some embodiments, the container comprises, consists essentially of, or consists of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 $cm^3/m^2 \cdot day$ (as measured in accordance with ASTM D3985).

In some embodiments, the container reduces the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

In some embodiments, the container reduces the amount of ambient moisture that reaches said plant propagation material by about 5, 10, 15, 20, 25, 30, 35, 40, 45, 50, 55, 60, 65, 70, 75, 80, 85, 90, 95 or 100% when sealed.

In some embodiments, the container reduces the amount of ambient oxygen that reaches said plant propagation material by about 5, 10, 15, 20, 25, 30, 35, 40, 45, 50, 55, 60, 65, 70, 75, 80, 85, 90, 95 or 100% when sealed.

In some embodiments, kits of the present disclosure comprise 1, 2, 3, 4, 5 or more additional containers. The additional containers may comprise any suitable component(s) or composition(s), including, but not limited to, agriculturally beneficial microorganisms, biostimulants, drying agents, nutrients, oxidation control components and pesticides. Examples of agriculturally beneficial microorganisms, biostimulants, drying agents, nutrients, oxidation control components and pesticides that may be included in the additional containers are described above.

The present disclosure extends to animal feed compositions comprising, consisting essentially of or consisting of a food component and a microbial component, said microbial component comprising, consisting essentially of, or consisting of one or more strains of the present disclosure and/or an inoculant composition of the present disclosure.

Animal feed compositions of the present disclosure may comprise any suitable food component, including, but not limited to, fodder (e.g., grains, hay, legumes, silage and/or straw) and forage (e.g., grass).

Animal feed compositions of the present disclosure may be fed to any suitable animal, including, but not limited to, farm animals, zoo animals, laboratory animals and/or companion animals. In some embodiments, the animal feed composition is formulated to meet the dietary needs of birds (e.g., chickens, ducks, quails and/or turkeys), bovids (e.g., antelopes, bison, cattle, gazelles, goats, impala, oxen, sheep and/or wildebeests), canines, cervids (e.g., caribou, deer, elk and/or moose), equines (e.g., donkeys, horses and/or zebras), felines, fish, pigs, rabbits, rodents (e.g., guinea pigs, hamsters, mice and/or rats) and the like.

The present disclosure extends to methods and uses for strains of the present disclosure and inoculant compositions of the present disclosure.

In some embodiments, methods and uses of the present disclosure comprise, consist essentially of or consist of applying one or more strains of *P. koreensis* to a plant or plant part (e.g., plant propagation material). *P. koreensis* may be applied to any type of plant, to any part/portion of a plant, in any suitable manner, in any suitable amount(s)/concentration(s) and at any suitable time(s). According to some embodiments, methods and uses of the present disclosure comprise, consist essentially of or consist of applying one or more strains of *P. koreensis* to a dicotyledonous plant or plant part (e.g., a leguminous plant or plant part, optionally, alfalfa, beans, clover, lentils, peas, peanuts, or soybeans).

In some embodiments, methods and uses of the present disclosure comprise, consist essentially of or consist of applying one or more strains of *P. koreensis* to a plant growth medium. *P. koreensis* may be applied to any plant growth medium, in any suitable manner, in any suitable amount(s)/ concentration(s) and at any suitable time(s).

In some embodiments, methods and uses of the present disclosure comprise, consist essentially of or consist of introducing a plant or plant part (e.g., plant propagation material) that has been treated with one or more strains of *P. koreensis* into a plant growth medium (e.g., a soil). Such methods may further comprise introducing one or more nutrients (e.g., nitrogen and/or phosphorous) into the plant growth medium. Any suitable nutrient(s) may be added to the growth medium, including, but not limited to, rock phosphate, monoammonium phosphate, diammonium phosphate, monocalcium phosphate, super phosphate, triple super phosphate, ammonium polyphosphate, fertilizers comprising one or more phosphorus sources, and combinations thereof.

In some embodiments, methods and uses of the present disclosure comprise, consist essentially of or consist of growing a plant from a plant propagation material that has been treated with one or more strains of *P. koreensis*.

In some embodiments, methods and uses of the present disclosure comprise, consist essentially of or consist of applying one or more strains of the present disclosure (or an inoculant composition of the present disclosure) to a plant or plant part (e.g., plant propagation material). As noted above, strains of the present disclosure and inoculant compositions of the present disclosure may be applied to any type of plant, to any part/portion of a plant, in any suitable manner, in any suitable amount(s)/concentration(s) and at any suitable time(s). According to some embodiments, methods and uses of the present disclosure comprise, consist essentially of or consist of applying one or more strains of the present disclosure (or an inoculant composition of the present disclosure) to a dicotyledonous plant or plant part (e.g., a leguminous plant or plant part, optionally, alfalfa, beans, clover, lentils, peas, peanuts, or soybeans).

In some embodiments, methods and uses of the present disclosure comprise, consist essentially of or consist of applying one or more strains of the present disclosure (or an inoculant composition of the present disclosure) to a plant growth medium. As noted above, strains of the present disclosure and inoculant compositions of the present disclosure may be applied to any plant growth medium, in any suitable manner, in any suitable amount(s)/concentration(s) and at any suitable time(s).

In some embodiments, methods and uses of the present disclosure comprise, consist essentially of or consist of introducing a plant or plant part (e.g., plant propagation material) that has been treated with one or more strains of the present disclosure (or an inoculant composition of the present disclosure) into a plant growth medium (e.g., a soil). Such methods may further comprise introducing one or more nutrients (e.g., nitrogen and/or phosphorous) into the plant growth medium. Any suitable nutrient(s) may be added to the growth medium, including, but not limited to, rock phosphate, monoammonium phosphate, diammonium phosphate, monocalcium phosphate, super phosphate, triple super phosphate, ammonium polyphosphate, fertilizers comprising one or more phosphorus sources, and combinations thereof.

In some embodiments, methods and uses of the present disclosure comprise, consist essentially of or consist of growing a plant from a plant propagation material that has been treated with one or more strains of the present disclosure (or an inoculant composition of the present disclosure).

*P. koreensis* may be used to enhance the growth and/or yield of various plants, including, but not limited to, cereals and pseudocereals, such as barley, buckwheat, corn, millet, oats, *quinoa*, rice, rye, sorghum and wheat, and legumes, such as alfalfa, beans, carob, clover, guar, lentils, mesquite, peas, peanuts, soybeans, tamarind, tragacanth and vetch. In some embodiments, application of one or more strains of the present disclosure enhances 1, 2, 3, 4, 5 or more growth characteristics and/or 1, 2, 3, 4, 5 or more yield characteristics by about/at least 5, 10, 15, 20, 25, 30, 35, 40, 45, 50, 55, 60, 65, 70, 75, 80, 85, 90, 95, 100, 105, 110, 115, 120, 125, 150, 175, 200, 225, 250% or more as compared to one or more controls (e.g., untreated control plants and/or plants treated with an alternative microbial strain). For example, in some embodiments, application of *P. koreensis* NRRL B-67883 enhances cereal or pseudocereal yield by about/at least 0.25, 0.5, 0.75, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 4.1, 4.2, 4.3, 4.4, 4.5 or 4.6 bushels per acre as compared to the yield of untreated control plants and/or plants treated with an alternative microbial strain. Similarly, in some embodiments, application of *P. koreensis* NRRL B-67883 enhances legume yield by about/at least 0.25, 0.5, 0.75, 1, 1.1, 1.2, 1.3, 1.4, 1.5, 1.6, 1.7, 1.8, 1.9 or 2.0 bushels per acre as compared to the yield of untreated control plants and/or plants treated with an alternative microbial strain.

Inoculant compositions comprising one or more strains of *P. koreensis* may likewise be used to enhance the growth and/or yield of various plants, including, but not limited to, cereals and pseudocereals, such as barley, buckwheat, corn, millet, oats, *quinoa*, rice, rye, sorghum and wheat, and legumes, such as alfalfa, beans, carob, clover, guar, lentils, mesquite, peas, peanuts, soybeans, tamarind, tragacanth and vetch. In some embodiments, application of an inoculant composition of the present disclosure enhances 1, 2, 3, 4, 5 or more growth characteristics and/or 1, 2, 3, 4, 5 or more yield characteristics by about/at least 5, 10, 15, 20, 25, 30, 35, 40, 45, 50, 55, 60, 65, 70, 75, 80, 85, 90, 95, 100, 105, 110, 115, 120, 125, 150, 175, 200, 225, 250% or more as compared to a control composition (e.g., a control composition that is identical to the inoculant composition of the present disclosure except that it lacks at least one of the strains of the present disclosure found in the inoculant composition). For example, in some embodiments, application of an inoculant composition of the present disclosure enhances cereal or pseudocereal yield by about/at least 0.25, 0.5, 0.75, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 4.1, 4.2, 4.3, 4.4, 4.5 or 4.6 bushels per acre as compared to a control composition (e.g., a control composition that is identical to the inoculant composition of the present disclosure except that it lacks at least one of the strains of the present disclosure found in the inoculant composition). Similarly, in some embodiments, application of an inoculant composition of the present disclosure enhances legume yield by about/at least 0.25, 0.5, 0.75, 1, 1.1, 1.2, 1.3, 1.4, 1.5, 1.6, 1.7, 1.8, 1.9 or 2.0 bushels per acre as compared to a control composition (e.g., a control composition that is identical to the inoculant composition of the present disclosure except that it lacks at least one of the strains found in the inoculant composition).

Accordingly, in some embodiments, methods and uses of the present disclosure comprise, consist essentially of or consist of applying one or more strains of *P. koreensis* (e.g., one or more strains of the present disclosure) to cereal, pseudocereal or legume seed, to the plant growth medium in which said cereal, pseudocereal or legume seed is being or will be grown, and/or to the plant(s) that grow(s) from said cereal, pseudocereal or legume seed.

In some embodiments, one or more strains of the present disclosure (or an inoculant composition of the present disclosure) is applied to cereal or psuedocereal seed in an amount/concentration effective to enhance 1, 2, 3, 4, 5 or more plant growth characteristics (e.g., biomass) and/or 1, 2, 3, 4, 5 or more plant yield characteristics (e.g., bushels per acre) of the plant that grows from said seed by at least about 5, 10, 15, 20, 25, 30, 35, 40, 45, 50, 55, 60, 65, 70, 75, 80, 85, 90, 95, 100, 105, 110, 115, 120, 125, 150, 175, 200, 225, 250% or more as compared to one or more control plants (e.g., plants grown from untreated seed and/or plants grown from seed treated with a control composition that is identical to the inoculant composition of the present disclosure except that it lacks at least one of the strains of the present disclosure found in the inoculant composition). According to some embodiments, one or more strains of the present disclosure (or an inoculant composition of the present disclosure) is applied to cereal or psuedocereal seed in an amount effective to enhance yield by about/at least 0.25, 0.5, 0.75, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 4.1, 4.2, 4.3, 4.4, 4.5 or 4.6 bushels per acre.

In some embodiments, one or more strains of the present disclosure (or an inoculant composition of the present disclosure) is introduced into a plant growth medium (e.g., soil) in an amount/concentration effective to enhance 1, 2, 3, 4, 5 or more plant growth characteristics (e.g., biomass) and/or 1, 2, 3, 4, 5 or more plant yield characteristics (e.g., bushels per acre) of cereal or psuedocereal plants grown therein by at least about 5, 10, 15, 20, 25, 30, 35, 40, 45, 50, 55, 60, 65, 70, 75, 80, 85, 90, 95, 100, 105, 110, 115, 120, 125, 150, 175, 200, 225, 250% or more as compared to one or more controls (e.g., plants grown in untreated soil and/or plants grown in soil treated with an alternative microbial strain). According to some embodiments, one or more strains of the present disclosure (or an inoculant composition of the present disclosure) is introduced into the plant growth medium in an amount effective to enhance cereal or psuedocereal yield by about/at least 0.25, 0.5, 0.75, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 4.1, 4.2, 4.3, 4.4, 4.5 or 4.6 bushels per acre.

In some embodiments, one or more strains of the present disclosure (or an inoculant composition of the present disclosure) is applied to legume seed in an amount/concentration effective to enhance 1, 2, 3, 4, 5 or more plant growth characteristics (e.g., biomass) and/or 1, 2, 3, 4, 5 or more plant yield characteristics (e.g., bushels per acre) of the plant that grows from said seed by at least about 5, 10, 15, 20, 25, 30, 35, 40, 45, 50, 55, 60, 65, 70, 75, 80, 85, 90, 95, 100, 105, 110, 115, 120, 125, 150, 175, 200, 225, 250% or more as compared to one or more control plants (e.g., plants grown from untreated seed and/or plants grown from seed treated with a control composition that is identical to the inoculant composition of the present disclosure except that it lacks at least one of the strains found in the inoculant composition). According to some embodiments, one or more strains of the present disclosure (or an inoculant composition of the present disclosure) is applied to legume seed in an amount effective to enhance yield by about/at least 0.25, 0.5, 0.75, 1, 1.1, 1.2, 1.3, 1.4, 1.5, 1.6, 1.7, 1.8, 1.9 or 2.0 bushels per acre.

In some embodiments, one or more strains of the present disclosure (or an inoculant composition of the present disclosure) is introduced into a plant growth medium (e.g., soil) in an amount/concentration effective to enhance 1, 2, 3, 4, 5 or more plant growth characteristics (e.g., biomass) and/or 1, 2, 3, 4, 5 or more plant yield characteristics (e.g., bushels per acre) of legume plants grown therein by at least about 5, 10, 15, 20, 25, 30, 35, 40, 45, 50, 55, 60, 65, 70, 75, 80, 85, 90, 95, 100, 105, 110, 115, 120, 125, 150, 175, 200, 225, 250% or more as compared to one or more controls (e.g., plants grown in untreated soil and/or plants grown in soil treated with an alternative microbial strain). According to some embodiments, one or more strains of the present disclosure (or an inoculant composition of the present disclosure) is introduced into the plant growth medium in an amount effective to enhance legume yield by about/at least 0.25, 0.5, 0.75, 1, 1.1, 1.2, 1.3, 1.4, 1.5, 1.6, 1.7, 1.8, 1.9 or 2.0 bushels per acre.

*P. koreensis* may be used to enhance plant growth and/or yield under various growth conditions, including, but not limited to, nutritional deficits (e.g., calcium, iron, manganese, magnesium, nitrogen, phosphorous, potassium and/or sulfur deficiencies), humidity extremes, pH extremes, temperature extremes, (e.g., average daytime temperatures below 60, 61, 62, 63, 64, 65, 66, 67, 68, 69, 70, 71, 72, 73 74 or 75° C., average daytime temperatures above 85, 86, 87, 88, 89, 90, 91, 92, 93, 94, 95, 96, 97, 98, 99, 100° C. or more, average nighttime temperatures below 50, 51, 52, 53, 54, 55, 56, 57, 58, 59, 60, 61, 62, 63, 64, 65, 66, 67, 68, 69 or 70° C., average nighttime temperatures above 70, 71, 72, 73, 74, 75, 76, 77, 78, 79, 80, 81, 82, 83, 84, 85° C. or more, etc.) and drought conditions (e.g., less than 5, 6, 7, 8, 9, 10, 11, 12, 13, 14 or 15 inches of rainfall during the growing season). It is to be understood that any determination of what constitutes a nutritional deficit, temperature extreme, drought condition, etc. must account for the plant species/variety being grown, as different species/varieties may have different preferences and requirements.

*P. koreensis* may be used to enhance plant growth and/or yield in various geographical regions, including, but not limited to, agricultural regions in Afghanistan, Argentina, Australia, Bangladesh, Bolivia, Brazil, Canada, Chile, China, Columbia, Ecuador, Egypt, Ethiopia, Europe (e.g., agricultural regions in Austria, Belgium, Bulgaria, Czech Republic, Denmark, France, Germany, Hungary, Ireland, Italy, Lithuania, the Netherlands, Poland, Romania, Spain, Sweden and/or the United Kingdom), India, Indonesia, Iran, Iraq, Japan, Kazakhstan, Kenya, Malawi, Mexico, Morocco, Nigeria, Pakistan, Paraguay, Peru, the Philippines, Russia, South Africa, Taiwan, Tanzania, Thailand, Turkey, Ukraine, the United States (e.g., agricultural regions in Arkansas, Colorado, Idaho, Illinois, Indiana, Iowa, Kansas, Kentucky, Michigan, Minnesota, Mississippi, Missouri, Montana, Nebraska, North Dakota, Ohio, Oklahoma, South Dakota, Texas and/or Wisconsin), Uzbekistan, Venezuela, Vietnam, Zambia and/or Zimbabwe. In some embodiments, one or more strains of the present disclosure (or an inoculant composition of the present disclosure) is used to enhance plant growth and/or yield in a geographical region that encompasses multiple agricultural regions (e.g., agricultural regions in Illinois, Iowa, southern Minnesota and eastern Nebraska). Examples of such geographical regions include, but are not limited to, a northern corn region encompassing agricultural regions in Iowa (e.g., northern Iowa), Michigan, Minnesota, North Dakota, South Dakota and/or Wisconsin; a central corn region encompassing agricultural regions in Illinois (e.g., northern and/or central Illinois), Indiana (e.g., northern Indiana), Iowa (e.g., southern Iowa), Kansas (e.g., northern Kansas), Missouri (e.g, northern Missouri), Nebraska (e.g., northern and/or southern Nebraska) and/or Ohio; a southern corn region encompassing agricultural regions in Alabama (e.g., northern and/or southern Alabama), Arkansas, Georgia (e.g., northern and/or southern Georgia), Illinois (e.g., southern Illinois), Indiana (e.g., southern Indiana), Kansas, Kentucky, Louisiana, Maryland, Missouri (e.g., central and/or southern Missouri), Mississippi (e.g., northern and/or southern Mississippi), Nebraska (e.g., southern Nebraska), North Carolina, Oklahoma, South Carolina, Tennessee, Texas and/or Virginia; a northern wheat region encompassing agricultural regions in Minnesota, Montana (e.g., eastern Montana), Nebraska, North Dakota, South Dakota and/or Wyoming (e.g., eastern Wyoming); a northern wheat region encompassing agricultural regions in Idaho, Oregon and/or Washington; a central wheat region encompassing agricultural regions in Colorado, Nebraska, South Dakota and/or Wyoming (e.g., eastern Wyoming); a central wheat region encompassing agricultural regions in Illinois, Indiana, Iowa, Missouri and/or Ohio; a central wheat region encompassing agricultural regions in Kansas, Oklahoma and/or Texas; and a southern wheat region encompassing agricultural regions in Oklahoma and/or Texas.

Particular embodiments of the present disclosure are described in the following numbered paragraphs:

1. The isolated microbial strain having the deposit accession number NRRL B-67883 (*P. koreensis* NRRL B-67883).

2. A biologically pure culture of *P. koreensis* NRRL B-67883.

3. An inoculant composition comprising, consisting essentially of or consisting of *P. koreensis* NRRL B-67883 and an agriculturally acceptable carrier.

4. The inoculant composition of paragraph 3, said composition comprising about $1 \times 10^3$ to about $1 \times 10^{12}$ colony-forming units (cfu) of *P. koreensis* NRRL B-67883 per gram and/or milliliter of inoculant composition, optionally about/at least $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, or $1 \times 10^{12}$ cfu of *P. koreensis* NRRL B-67883 per gram and/or milliliter of inoculant composition.

5. The inoculant composition of any one paragraphs 3-4, said composition further comprising one or more stabilizing compounds.

6. The inoculant composition of paragraph 5, said one or more stabilizing compounds comprising, consisting essentially of or consisting of:

one or more monosaccharides, optionally arabinose, fructose and/or glucose;

one or more disaccharides, optionally maltose, sucrose and/or trehalose;

one or more maltodextrins, optionally one or more maltodextrins (e.g., one or more maltodextrins (each and/or collectively) having a DEV value of about 15 to about 20;

one or more sugar alcohols, optionally arabitol, mannitol, sorbitol and/or xylitol;

one or more humic acids, optionally potassium humate and/or sodium humate;

one or more fulvic acids, optionally potassium fulvate and/or sodium fulvate;

one or more hygroscopic polymers, optionally one or more albumins, alginates, celluloses, gums (e.g., cellulose gum, guar gum, gum arabic, gum combretum, xantham gum), methyl celluloses, nylons, pectins, polyacrylic acids, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches;

one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid)

and/or one or more oxygen scavengers, optionally ascorbic acid and/or sodium hydrogen carbonate; and/or one or more UV protectants, optionally one or more lignosulfites.

7. The inoculant composition of any one paragraphs 5-6, said one or more stabilizing compounds comprising about 0.0001 to about 10% (by weight) of said composition, optionally about 2 to about 6% (by weight) of said composition, optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 1, 1.5, 2, 2.5, 3, 3.5, 4, 4.5, 5, 5.5, 6, 7, 7.5, 8, 8.5, 9, 9.5 or 10% (by weight) of said composition.

8. The inoculant composition of any one of paragraphs 5-7, wherein said one or more stabilizing compounds is/are present in an amount/concentration sufficient to ensure P. koreensis NRRL B-67883 remain(s) viable in inoculant compositions of the present disclosure following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application to plant propagation material (optionally, seed);

application to plant propagation material and desiccation by about 5, 10, 15, 20, 25, 30, 35, 40, 45, 50, 55, 60, 65, 70, 75, 80, 85, 90, 95% or more;

application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

foliar application;

foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

9. The inoculant composition of any one of paragraphs 5-7, wherein said one or more stabilizing compounds is/are present in an amount/concentration sufficient to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of P. koreensis NRRL B-67883 remains viable following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application to plant propagation material (optionally, seed);

application to plant propagation material and desiccation by about 5, 10, 15, 20, 25, 30, 35, 40, 45, 50, 55, 60, 65, 70, 75, 80, 85, 90, 95% or more;

application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

foliar application;

foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

10. The inoculant composition of any one of paragraphs 5-7, wherein said one or more stabilizing compounds is/are present in an amount/concentration sufficient to ensure at least $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$ or more colony-forming units of P.

*koreensis* NRRL B-67883 per gram and/or milliliter of inoculant composition remain viable following:
  storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
  desiccation by about 5, 10, 15, 20, 25, 30, 35, 40, 45, 50, 55, 60, 65, 70, 75, 80, 85, 90, 95% or more;
  desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
  cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
  application to plant propagation material (optionally, seed);
  application to plant propagation material and desiccation by about 5, 10, 15, 20, 25, 30, 35, 40, 45, 50, 55, 60, 65, 70, 75, 80, 85, 90, 95% or more;
  application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
  foliar application;
  foliar application and desiccation by about 5, 10, 15, 20, 25, 30, 35, 40, 45, 50, 55, 60, 65, 70, 75, 80, 85, 90, 95% or more; and/or
  foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

11. The inoculant composition of any one paragraphs 3-10, said composition further comprising one or more biostimulants, optionally one or more seaweed extracts, myo-inositol and/or glycine.

12. The inoculant composition of any one paragraphs 3-11, said composition further comprising one or more microbial extracts, optionally one or more of the microbial extracts expressly disclosed above.

13. The inoculant composition of any one paragraphs 3-12, said composition further comprising one or more nutrients, optionally one or more vitamins (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$ and/or choline) vitamin C, vitamin D, vitamin E and/or vitamin K), carotenoids (α-carotene, β-carotene, cryptoxanthin, lutein, lycopene and/or zeaxanthin), macro-minerals (e.g., calcium, iron, magnesium, phosphorous, potassium and/or sodium), trace minerals (e.g., boron, cobalt, chloride, chromium, copper, fluoride, iodine, iron, manganese, molybdenum, selenium and/or zinc) and/or organic acids (e.g., acetic acid, citric acid, lactic acid, malic aclid and/or taurine).

14. The inoculant composition of any one paragraphs 3-13, said composition further comprising one or more pest attractant and/or feeding stimulants, optionally brevicomin, ceralure, codlelure, cue-lure, disparlure, dominicalure, eugenol, frontalin, gossyplure, grandlure, hexalure, ipsdienol, ipsenol, japonilure, latitlure, lineatin, litlure, looplure, medlure, megatomic acid, methyl eugenol, moguchun, α-multistriatin, muscalure, orfalure, oryctalure, ostramone, rescalure, siglure, sulcatol, trimedlure and/or trunc-call.

15. The inoculant composition of any one paragraphs 3-14, said composition further comprising one or more pesticides, optionally:
  one or more fungicides, optionally one or more of the fungicides expressly disclosed above;
  one or more herbicides, optionally one or more of the herbicides expressly disclosed above;
  one or more insecticides, optionally one or more of the insecticides expressly disclosed above; and/or
  one or more nematicides, optionally one or more of the nematicides expressly disclosed on above.

16. The inoculant composition of any one paragraphs 3-15, said composition further comprising one or more lipo-chitooligosaccharides, optionally one or more of the lipo-chitooligosaccharides represented by formulas I-IV as set forth in International Patent Publication No. WO 2019/136198.

17. The inoculant composition of any one paragraphs 3-15, said composition further comprising one or more of the lipo-chitooligosaccharides represented by structures V-XXXIII as set forth in International Patent Publication No. WO 2019/136198.

18. The inoculant composition of any one paragraphs 3-17, said composition further comprising one or more chitooligosaccharides, optionally one or more of the chitin oligosaccharides represented by formulas XXXIV-XXXV as set forth in International Patent Publication No. WO 2019/136198.

19. The inoculant composition of any one paragraphs 3-17, said composition further comprising one or more of the chitin oligosaccharides represented by structures XXXVI-LXXXIII as set forth in International Patent Publication No. WO 2019/136198.

20. The inoculant composition of any one paragraphs 3-19, said composition further comprising one or more chitinous compounds, optionally one or more chitins and/or one or more chitosans.

21. The inoculant composition of any one paragraphs 3-20, said composition further comprising one or more flavonoids, optionally one or more anthocyanidins, such as cyanidin, delphinidin, malvidin, pelargonidin, peonidin and/or petunidin; anthoxanthins, such as flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin); flavanones, such as butin, eriodictyol, hesperetin, hesperidin, homoeriodictyol, isosakuranetin, naringenin, naringin, pinocembrin, poncirin, sakuranetin, sakuranin and/or sterubin; flavanonols, such as dihydrokaempferol and/or taxifolin; flavans, such as flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin); and/or isoflavonoids, such as isoflavones (e.g, biochanin A, daidzein, formononetin, genistein and/or glycitein), isoflavanes (e.g., equol, ionchocarpane and/or laxifloorane), isoflavandiols, isoflavenes (e.g., glabrene, haginin D and/or 2-methoxyjudaicin), coumestans (e.g., coumestrol, plicadin and/or wedelolactone), pterocarpans and/or roetonoids; and/or one oor more analogues, derivatives, hydrates, isomers, polymers, salts and solvates thereof, such as neoflavonoids (e.g, calophyllolide, coutareagenin, dalbergichromene, dalbergin and/or nivetin) and/or pterocarpans (e.g., bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine and/or trifolirhizin).

22. The inoculant composition of any one paragraphs 3-21, said composition further comprising jasmonic acid and/or one or more derivatives thereof.

23. The inoculant composition of any one paragraphs 3-22, said composition further comprising linoleic acid and/or one or more derivatives thereof.

24. The inoculant composition of any one paragraphs 3-23, said composition further comprising linolenic acid and/or one or more derivatives thereof.

25. The inoculant composition of any one paragraphs 3-24, said composition further comprising one or more karrakins, optionally one or more karrakins represented by formula LXXXIV as set forth in International Patent Publication No. WO 2019/136198.

26. The inoculant composition of any one paragraphs 3-25, said composition further comprising gluconolactone.

27. The inoculant composition of any one of paragraphs 3-26, said composition further comprising one or more additional microorganisms.

28. The inoculant composition of paragraph 27, said one or more additional microorganisms comprising, consisting essentially of or consisting of one or more microorganisms that improve the availability of a soil nutrient, optionally one or more diazotrophs and/or phosphate-solubilixing microorganisms.

29. The inoculant composition of paragraph 27, said one or more additional microorganisms comprising, consisting essentially of or consisting of *Azospirillum brasilense* INTA Az-39, *Bacillus amyloliquefaciens* D747, *Bacillus amyloliquefaciens* NRRL B-50349, *Bacillus amyloliquefaciens* TJ1000, *Bacillus amyloliquefaciens* FZB24, *Bacillus amyloliquefaciens* FZB42, *Bacillus amyloliquefaciens* IN937a, *Bacillus amyloliquefaciens* IT-45, *Bacillus amyloliquefaciens* TJ1000, *Bacillus amyloliquefaciens* MBI600, *Bacillus amyloliquefaciens* BS27 (deposited as NRRL B-5015), *Bacillus amyloliquefaciens* BS2084 (deposited as NRRL B-50013), *Bacillus amyloliquefaciens* 15AP4 (deposited as ATCC PTA-6507), *Bacillus amyloliquefaciens* 3AP4 (deposited as ATCC PTA-6506), *Bacillus amyloliquefaciens* LSSA01 (deposited as NRRL B-50104), *Bacillus amyloliquefaciens* ABP278 (deposited as NRRL B-50634), *Bacillus amyloliquefaciens* 1013 (deposited as NRRL B-50509), *Bacillus amyloliquefaciens* 918 (deposited as NRRL B-50508), *Bacillus amyloliquefaciens* 22CP1 (deposited as ATCC PTA-6508) and *Bacillus amyloliquefaciens* BS18 (deposited as NRRL B-50633), *Bacillus cereus* I-1562, *Bacillus firmus* I-1582, *Bacillus lichenformis* BA842 (deposited as NRRL B-50516), *Bacillus lichenformis* BL21 (deposited as NRRL B-50134), *Bacillus mycoides* NRRL B-21664, *Bacillus pumilus* NRRL B-21662, *Bacillus pumilus* NRRL B-30087, *Bacillus pumilus* ATCC 55608, *Bacillus pumilus* ATCC 55609, *Bacillus pumilus* GB34, *Bacillus pumilus* KFP9F, *Bacillus pumilus* QST 2808, *Bacillus subtilis* ATCC 55078, *Bacillus subtilis* ATCC 55079, *Bacillus subtilis* MBI 600, *Bacillus subtilis* NRRL B-21661, *Bacillus subtilis* NRRL B-21665, *Bacillus subtilis* CX-9060, *Bacillus subtilis* GB03, *Bacillus subtilis* GB07, *Bacillus subtilis* QST-713, *Bacillus subtilis* FZB24, *Bacillus subtilis* D747, *Bacillus subtilis* 3BP5 (deposited as NRRL B-50510), *Bacillus thuringiensis* ATCC 13367, *Bacillus thuringiensis* GC-91, *Bacillus thuringiensis* NRRL B-21619, *Bacillus thuringiensis* ABTS-1857, *Bacillus thuringiensis* SAN 401 I, *Bacillus thuringiensis* ABG-6305, *Bacillus thuringiensis* ABG-6346, *Bacillus thuringiensis* AM65-52, *Bacillus thuringiensis* SA-12, *Bacillus thuringiensis* SB4, *Bacillus thuringiensis* ABTS-351, *Bacillus thuringiensis* HD-1, *Bacillus thuringiensis* EG 2348, *Bacillus thuringiensis* EG 7826, *Bacillus thuringiensis* EG 7841, *Bacillus thuringiensis* DSM 2803, *Bacillus thuringiensis* NB-125, *Bacillus thuringiensis* NB-176, BRADY, *Mesorhizobium huakii* LL32, *Pseudomonas jessenii* PS06, *Rhizobium leguminosarum* 162BB1, *Rhizobium leguminosarum* 162P17, *Rhizobium leguminosarum* 175G10b, *Rhizobium leguminosarum* D36, *Rhizobium leguminosarum* SO12A-2 (IDAC 080305-01), *Rhizobium loti* 95C11, *Rhizobium loti* 95C14, *Sinorhizobium fredii* CCBAU114, *Sinorhizobium fredii* USDA 205, *Sinorhizobium meliloti* 102F34a, *Sinorhizobium meliloti* 102F51a, *Sinorhizobium meliloti* 102F77b, *Sinorhizobium meliloti* B401, and/or *Yersinia entomophaga* O82KB8.

30. The inoculant composition of paragraph 27, said one or more additional microorganisms comprising, consisting essentially of or consisting of *Gliocladium virens* ATCC 52045, *Gliocladium virens* GL-21, *Glomus intraradices* RTI-801, *Metarhizium anisopliae* F52, PENT, *Trichoderma asperellum* SKT-1, *Trichoderma asperellum* ICC 012, *Trichoderma atroviride* LC52, *Trichoderma atroviride* CNCM 1-1237, *Trichoderma fertile* JM41R, *Trichoderma gamsii* ICC 080, *Trichoderma hamatum* ATCC 52198, *Trichoderma harzianum* ATCC 52445, *Trichoderma harzianum* KRL-AG2, *Trichoderma harzianum* T-22, *Trichoderma harzianum* TH-35, *Trichoderma harzianum* T-39, *Trichoderma harzianum* ICC012, *Trichoderma reesi* ATCC 28217, *Trichoderma virens* ATCC 58678, *Trichoderma virens* G1-3, *Trichoderma virens* GL-21, *Trichoderma virens* G-41, *Trichoderma viridae* ATCC 52440, *Trichoderma viridae* ICC080, and/or *Trichoderma viridae* TV1.

31. The inoculant composition of paragraph 27, said one or more additional microorganisms comprising, consisting essentially of or consisting of one or more biopesticides, optionally one or more acaricidal, insecticidal and/or nematicidal microorganisms and one or more fungicidal microorganisms.

32. The inoculant composition of any one of claims 27-31, said composition comprising about $1 \times 10^3$ to about $1 \times 10^{12}$ colony-forming units (cfu) of said one or more additional microorganisms per gram and/or milliliter of inoculant composition, optionally about/at least $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, or $1 \times 10^{12}$ cfu of said one or more additional microorganisms per gram and/or milliliter of inoculant composition.

33. The inoculant composition of any one paragraphs 3-32, wherein said composition is non-aqueous.

34. The inoculant composition of any one paragraphs 3-32, wherein said composition is aqueous.

35. The inoculant composition of any one paragraphs 3-32, wherein said composition comprises less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5% water (by weight, based upon the total weight of the composition).

36. The inoculant composition of any one paragraphs 3-35, wherein said composition is an amorphous liquid.

37. The inoculant composition of any one paragraphs 3-35, wherein said composition is an amorphous solid.

38. The inoculant composition of any one paragraphs 3-35, wherein said composition is a freeze-, spray- or spray-freeze-dried composition, optionally a freeze-, spray- or spray-freeze-dried powder.

39. A non-naturally occurring composition, comprising the isolated strain of paragraph 1 and a plant or plant part to which the isolated strain of paragraph 1 has been applied.

40. A non-naturally occurring composition, comprising the isolated strain of paragraph 1 and a plant or plant part infected with the isolated strain of paragraph 1.

41. A non-naturally occurring composition, comprising the biologically pure culture of paragraph 2 and a plant or plant part to which the biologically pure culture of paragraph 2 has been applied.

42. A non-naturally occurring composition, comprising the inoculant composition of any one of paragraphs 3-38 and a plant or plant part to which the inoculant composition of any one of paragraphs 3-38 has been applied.

43. The non-naturally occurring composition of paragraph 42, comprising, consisting essentially of, or consisting of: a plant propagation material, optionally a seed; and a coating that covers at least a portion of the outer surface of said plant propagation material, said coating comprising, consisting essentially of, or consisting of the inoculation composition of any one of paragraphs 3-38.

44. The non-naturally occurring composition of paragraph 43, said coating comprising, consisting essentially of, or consisting of an inner coating layer that comprises *P. koreensis* NRRL B-67883 and an outer coating layer that is devoid (or essentially devoid) of *P. koreensis* NRRL B-67883.

45. The non-naturally occurring composition of any one of paragraphs 43-44, wherein said coating comprises about $1 \times 10^1$ to about $1 \times 10^{15}$ colony-forming units of *P. koreensis* NRRL B-67883, optionally $1 \times 10^4$, $1 \times 10^5$, $1 \times 10^6$, $1 \times 10^7$ or more colony-forming units.

46. A plant germinated from the plant part of any one of paragraphs 39-45.

47. A plant part harvested from the plant of any one of paragraphs 39-42 and 46.

48. A processed product produced from the plant part of paragraph 47.

49. A crop comprising, consisting essentially of, or consisting of a plurality of the plant of any one of paragraphs 39-42 and 47.

50. A kit, comprising: the plant or plant part of any one of paragraphs any one of paragraphs 39-45; and a container housing said plant or plant part.

51. The kit of claim 50, said container reducing the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

52. The kit of any one of paragraphs 50-51, said container reducing the amount of ambient oxygen that reaches said plant propagation material by about 5, 10, 15, 20, 25, 30, 35, 40, 45, 50, 55, 60, 65, 70, 75, 80, 85, 90, 95 or 100% when sealed.

53. The kit of any one of paragraphs 50-52, said container comprising, consisting essentially of, or consisting of a material having light permeability of less than about 1, 2, 3, 4, 5, 6, 7, 8, 9, 10, 15, 20, 25, 30, 35, 40, 45, 50, 55, 60, 65, 70 or 75%.

54. The kit of any one of paragraphs 50-53, said container comprising, consisting essentially of, or consisting of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 $cm^3/m^2$·day (as measured in accordance with ASTM D3985).

55. The kit of any one of paragraphs 50-54, said kit furthering comprising one or more oxygen-absorbing compound, optionally activated carbon, iron powder, sodium chloride, ferrous carbonate, one or more metal halide catalysts and/or sodium hydrogen carbonate.

56. A method, comprising, consisting essentially of or consisting of: applying the isolated strain of paragraph 1, the biologically pure culture of paragraph 2 or the inoculant composition of any one of paragraphs 3-38 to a plant or plant part, optionally a seed.

57. The method of paragraph 56, in which said isolated strain, biologically pure culture or inoculant composition is applied to the plant or plant part in an effective amount/concentration for enhancing growth and/or yield; chlorophyll production/accumulation/content; nutrient uptake/accumulation/content, optionally calcium, copper, iron, manganese, mangenisum, nitrogen, potassium, phosphorous and/or zinc uptake/accumulation/content; heme production/accumulation/content; and/or root growth, in/of said plant or plant part.

58. A method, comprising, consisting essentially of or consisting of: applying the isolated strain of paragraph 1, the biologically pure culture of paragraph 2 or the inoculant composition of any one of paragraphs 3-38 to a plant propagation material, optionally a seed, at the time of planting said plant propagation material in a plant growth medium, optionally a soil.

59. A method, comprising, consisting essentially of or consisting of: applying the isolated strain of paragraph 1, the biologically pure culture of paragraph 2 or the inoculant composition of any one of paragraphs 3-38 to a plant propagation material, optionally a seed, about/at least 1, 2, 3, 4, 5, 6, 7, 8, 9, 10, 11, 12, 15, 18, 21, 24, 27, 30, 33, 36, 39, 42, 45, 48 hours or more prior to planting said plant propagation material in a plant growth medium, optionally a soil.

60. A method, comprising, consisting essentially of or consisting of: applying the isolated strain of paragraph 1, the biologically pure culture of paragraph 2 or the inoculant composition of any one of paragraphs 3-38 to a plant propagation material, optionally a seed, about/at least 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more prior to planting said plant propagation material in a plant growth medium, optionally a soil.

61. A method, comprising, consisting essentially of or consisting of: applying the isolated strain of paragraph 1, the biologically pure culture of paragraph 2 or the inoculant composition of any one of paragraphs 3-38 to a plant propagation material, optionally a seed, about/at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months or more prior to planting said plant propagation material in a plant growth medium, optionally a soil.

62. The method of any one of paragraphs 58-61, in which said isolated strain, biologically pure culture or inoculant composition is applied to the plant propagation material in an effective amount/concentration for enhancing growth and/or yield; chlorophyll production/accumulation/content; nutrient uptake/accumulation/content, optionally calcium, copper, iron, manganese, mangenisum, nitrogen, potassium, phosphorous and/or zinc uptake/accumulation/content; heme production/accumulation/content; and/or root growth, of a plant that grows from said plant propagation material.

63. A method, comprising, consisting essentially of or consisting of: introducing the isolated strain of paragraph 1, the biologically pure culture of paragraph 2 or the inoculant composition of any one of paragraphs 3-38 into a plant growth medium, optionally a soil.

64. The method of paragraph 63, in which said isolated strain, biologically pure culture or inoculant composition is introduced into said plant growth medium about/at least 1, 2, 3, 4, 5, 6, 7, 8, 9, 10, 11, 12, 15, 18, 21, 24, 27, 30, 33, 36, 39, 42, 45, 48 hours or more prior to planting a plant propagation material, optionally a seed, in said plant growth medium.

65. The method of paragraph 63, in which said isolated strain, biologically pure culture or inoculant composition is introduced into said plant growth medium about/at least 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more prior to planting a plant propagation material, optionally a seed, in said plant growth medium.

66. The method of paragraph 63, in which said isolated strain, biologically pure culture or inoculant composition is introduced into said plant growth medium about/at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months or more prior to planting a plant propagation material, optionally a seed, in said plant growth medium.

67. The method of paragraph 63, in which said isolated strain, biologically pure culture or inoculant composition is introduced into said plant growth medium at the time of planting a plant propagation material, optionally a seed, in said plant growth medium.

68. The method of paragraph 63, in which said isolated strain, biologically pure culture or inoculant composition is introduced into said plant growth medium after planting a plant propagation material, optionally a seed, in said plant growth medium.

69. The method of any one of paragraphs 63-68, in which said isolated strain, biologically pure culture or inoculant composition is introduced into the plant growth medium in an effective amount/concentration for enhancing growth and/or yield; chlorophyll production/accumulation/content; nutrient uptake/accumulation/content, optionally calcium, copper, iron, manganese, mangenisum, nitrogen, potassium, phosphorous and/or zinc uptake/accumulation/content; heme production/accumulation/content; and/or root growth, of a plant or plant part grown therein.

70. The method of any one of paragraphs 56-69, in which one or more symbiotic diazotrophs is/are applied to the plant, plant part or plant growth medium.

71. The method of any one of paragraphs 56-69, in which *Azospirillum brasilense* INTA Az-39, BRADY, *Mesorhizobium huakii* LL32, *Rhizobium leguminosarum* 162BB1, *Rhizobium leguminosarum* 162P17, *Rhizobium leguminosarum* 175G10b, *Rhizobium leguminosarum* D36, *Rhizobium leguminosarum* SO12A-2 (IDAC 080305-01), *Rhizobium loti* 95C11, *Rhizobium loti* 95C14, *Sinorhizobium fredii* CCBAU114, *Sinorhizobium fredii* USDA 205, *Sinorhizobium meliloti* 102F34a, *Sinorhizobium meliloti* 102F51a, *Sinorhizobium meliloti* 102F77b, and/or *Sinorhizobium meliloti* B401 is/are applied to the plant, plant part or plant growth medium.

72. The method of any one of paragraphs 56-71, in which one or more phosphate-solubilizing microorganisms is/are applied to the plant, plant part or plant growth medium.

73. The method of any one of paragraphs 56-71, in which PENI is/are applied to the plant, plant part or plant growth medium.

74. A method, comprising, consisting essentially of or consisting of: introducing the non-naturally occurring composition of any one of paragraphs 39-45 into a plant growth medium, optionally a soil.

75. A method, comprising, consisting essentially of or consisting of: introducing the non-naturally occurring composition of any one of paragraphs 39-45 into soil in which plants of the same genus as said plant or plant part were cultivated in at least one of the three years prior to said introducing, optionally in each of the one, two or three years immediately preceding said introducing.

76. The method of any one of paragraphs 74-75, further comprising introducing one or more sources of phosphorous, optionally rock phosphate, monoammonium phosphate, diammonium phosphate, monocalcium phosphate, super phosphate, triple super phosphate, ammonium polyphosphate and/or one or more fertilizers comprising phosphorus, into said plant growth medium.

77. The method of any one of paragraphs 74-76, in which *P. koreensis* NRRL B-67883 is present in said non-naturally occurring composition in an effective amount/concentration for enhancing growth and/or yield; chlorophyll content; nutrient uptake/accumulation/content, optionally calcium, copper, iron, manganese, mangenisum, nitrogen, potassium, phosphorous and/or zinc uptake/accumulation/content; heme production/accumulation/content; and/or root growth, of the plant or plant part in said non-naturally occurring composition following introduction into said plant growth medium.

78. The method of any one of paragraphs 74-77, in which one or more symbiotic diazotrophs is/are introduced into the plant growth medium.

79. The method of any one of paragraphs 74-77, in which *Azospirillum brasilense* INTA Az-39, BRADY, *Mesorhizobium huakii* LL32, *Rhizobium leguminosarum* 162BB1, *Rhizobium leguminosarum* 162P17, *Rhizobium leguminosarum* 175G10b, *Rhizobium leguminosarum* D36, *Rhizobium leguminosarum* SO12A-2 (IDAC 080305-01), *Rhizobium loti* 95C11, *Rhizobium loti* 95C14, *Sinorhizobium fredii* CCBAU114, *Sinorhizobium fredii* USDA 205,

*Sinorhizobium meliloti* 102F34a, *Sinorhizobium meliloti* 102F51a, *Sinorhizobium meliloti* 102F77b, and/or *Sinorhizobium meliloti* B401 is/are introduced into the plant growth medium.

80. The method of any one of paragraphs 74-79, in which one or more phosphate-solubilizing microorganisms is/are introduced into the plant growth medium.

81. The method of any one of paragraphs 74-79, in which PENI is/are introduced into the plant growth medium.

82. Use of a *Pseudomonas*, optionally a *P. koreensis*, optionally *P. koreensis* NRRL B-67883, for treating a plant or plant part.

83. Use of a *Pseudomonas*, optionally a *P. koreensis*, optionally *P. koreensis* NRRL B-67883, for enhancing plant growth, optionally root area, root biomass, root length, root surface area, root volume, shoot diameter, shoot length, shoot girth:length ratio, shoot biomass, shoot surface area and/or shoot volume, and/or yield, optionally average pod count per plant, average pod weight per plant and/or bushels per acre.

84. Use of a *Pseudomonas*, optionally a *P. koreensis*, optionally *P. koreensis* NRRL B-67883, for enhancing chlorophyll production and/or accumulation and/or content in a plant or plant part.

85. Use of a *Pseudomonas*, optionally a *P. koreensis*, optionally *P. koreensis* NRRL B-67883, for solubilizing potassium, phosphorous and/or zinc in a plant growth medium.

86. Use of a *Pseudomonas*, optionally a *P. koreensis*, optionally *P. koreensis* NRRL B-67883, for enhancing nutrient uptake and/or accumulation and/or content, optionally calcium, copper, iron, manganese, mangenisum, nitrogen, potassium, phosphorous and/or zinc uptake and/or accumulation and/or content, in a plant or plant part.

87. Use of a *Pseudomonas*, optionally a *P. koreensis*, optionally *P. koreensis* NRRL B-67883, for increasing heme production and/or accumulation and/or content in a plant or plant part.

88. Use of a *Pseudomonas*, optionally a *P. koreensis*, optionally *P. koreensis* NRRL B-67883, for enhancing root growth, in a plant.

89. Use of a biologically pure culture of *Pseudomonas*, optionally a *P. koreensis*, optionally *P. koreensis* NRRL B-67883, for treating a plant or plant part.

90. Use of a biologically pure culture of *Pseudomonas*, optionally a *P. koreensis*, optionally *P. koreensis* NRRL B-67883, for enhancing plant growth and/or yield. 91. Use of a biologically pure culture of *Pseudomonas*, optionally a *P. koreensis*, optionally *P. koreensis* NRRL B-67883, for enhancing chlorophyll production and/or accumulation and/or content in a plant or plant part.

92. Use of a biologically pure culture of *Pseudomonas*, optionally a *P. koreensis*, optionally *P. koreensis* NRRL B-67883, for solubilizing potassium, phosphorous and/or zinc in a plant growth medium.

93. Use of a biologically pure culture of *Pseudomonas*, optionally a *P. koreensis*, optionally *P. koreensis* NRRL B-67883, for enhancing nutrient uptake and/or accumulation and/or content, optionally optionally calcium, copper, iron, manganese, mangenisum, nitrogen, potassium, phosphorous and/or zinc uptake and/or accumulation and/or content, in a plant or plant part.

94. Use of a biologically pure culture of *Pseudomonas*, optionally a *P. koreensis*, optionally *P. koreensis* NRRL B-67883, for increasing heme production and/or accumulation and/or content in a plant or plant part.

95. Use of a biologically pure culture of *Pseudomonas*, optionally a *P. koreensis*, optionally *P. koreensis* NRRL B-67883, for enhancing root growth, in a plant.

96. Use of a composition comprising one or more strains of *Pseudomonas*, optionally a *P. koreensis*, optionally *P. koreensis* NRRL B-67883, for treating a plant or plant part.

97. Use of a composition comprising one or more strains of *Pseudomonas*, optionally a *P. koreensis*, optionally *P. koreensis* NRRL B-67883, for enhancing plant growth and/or yield.

98. Use of a composition comprising one or more strains of *Pseudomonas*, optionally a *P. koreensis*, optionally *P. koreensis* NRRL B-67883, for enhancing chlorophyll production and/or accumulation and/or content in a plant or plant part.

99. Use of a composition comprising one or more strains of *Pseudomonas*, optionally a *P. koreensis*, optionally *P. koreensis* NRRL B-67883, for solubilizing potassium, phosphorous and/or zinc in a plant growth medium.

100. Use of a composition comprising one or more strains of *Pseudomonas*, optionally a *P. koreensis*, optionally *P. koreensis* NRRL B-67883, for enhancing nutrient uptake and/or accumulation and/or content, optionally calcium, copper, iron, manganese, mangenisum, nitrogen, potassium, phosphorous and/or zinc uptake and/or accumulation and/or content, in a plant or plant part.

101. Use of a composition comprising one or more strains of *Pseudomonas*, optionally a *P. koreensis*, optionally *P. koreensis* NRRL B-67883, for increasing heme production and/or accumulation and/or content in a plant or plant part.

102. Use of a composition comprising one or more strains of *Pseudomonas*, optionally a *P. koreensis*, optionally *P. koreensis* NRRL B-67883, for enhancing root growth, in a plant.

103. The use of any one of claims 82-102, in which said plant or plant part has previously been and/or is concurrently/subsequently treated with one or more symbiotic diazotrophs.

104. The use of any one of claims 82-102, in which said plant or plant part has previously been and/or is concurrently/subsequently treated with *Azospirillum brasilense* INTA Az-39, BRADY, *Mesorhizobium* huakii LL32, *Rhizobium leguminosarum* 162BB1, *Rhizobium leguminosarum* 162P17, *Rhizobium leguminosarum* 175G10b, *Rhizobium leguminosarum* D36, *Rhizobium leguminosarum* SO12A-2 (IDAC 080305-01), *Rhizobium loti* 95C11, *Rhizobium loti* 95C14, *Sinorhizobium fredii* CCBAU114, *Sinorhizobium fredii* USDA 205, *Sinorhizobium meliloti* 102F34a, *Sinorhizobium meliloti* 102F51a, *Sinorhizobium meliloti* 102F77b, and/or *Sinorhizobium meliloti* B401.

105. The use of any one of claims 82-104, in which said plant or plant part has previously been and/or is concurrently/subsequently treated with one or more phosphate-solubilizing microorganisms.

106. The use of any one of claims 82-104, in which said plant or plant part has previously been and/or is concurrently/subsequently treated with PENI.

107. The non-naturally occurring composition of any one of claims 39-45, plant of paragraph 46, plant part of paragraph 47, processed product of paragraph 48, crop of paragraph 49, kit of any one of paragraphs 50-55, method of any one of claims 56-81, or use of any one of claims 82-106, in which said plant or plant part is a monocot.

108. The non-naturally occurring composition of any one of claims 39-45, plant of paragraph 46, plant part of paragraph 47, processed product of paragraph 48, crop of paragraph 49, kit of any one of paragraphs 50-55, method of any one of claims 56-81, or use of any one of claims 82-106, in which said plant or plant part is a dicot.

109. The non-naturally occurring composition of any one of claims 39-45, plant of paragraph 46, plant part of paragraph 47, processed product of paragraph 48, crop of paragraph 49, kit of any one of paragraphs 50-55, method of any one of claims 56-81, or use of any one of claims 82-106, in which said plant or plant part is leguminous.

110. The non-naturally occurring composition of any one of claims 39-45, plant of paragraph 46, plant part of paragraph 47, processed product of paragraph 48, crop of paragraph 49, kit of any one of paragraphs 50-55, method of any one of claims 56-81, or use of any one of claims 82-106, in which said plant or plant part is non-leguminous.

111. The non-naturally occurring composition of any one of claims 39-45, plant of paragraph 46, plant part of paragraph 47, processed product of paragraph 48, crop of paragraph 49, kit of any one of paragraphs 50-55, method of any one of claims 56-81, or use of any one of claims 82-106, in which said plant or plant part is of the family Amaranthaceae, optionally chard, spinach, sugar beet, or quinoa; of the family Asteraceae, optionally artichoke, asters, chamomile, chicory, chrysanthemums, dahlias, daisies, echinacea, goldenrod, guayule, lettuce, marigolds, safflower, sunflowers, or zinnias; of the family Brassicaceae, optionally arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, or *Arabidopsis thaliana*; of the family Cucurbitaceae, optionally cantaloupe, cucumber, honeydew, melon, pumpkin, squash (e.g., acorn squash, butternut squash, summer squash), watermelon, or zucchini; of the family Fabaceae, optionally alfalfa, beans, carob, clover, guar, lentils, mesquite, peas, peanuts, soybeans, tamarind, tragacanth, or vetch; of the family Malvaceae, optionally cacao, cotton, durian, hibiscus, kenaf, kola, or okra; of the family Poaceae, optionally bamboo, barley, corn, fonio, lawn grass (e.g., Bahia grass, Bermudagrass, bluegrass, Buffalograss, Centipede grass, Fescue, or *Zoysia*), millet, oats, ornamental grasses, rice, rye, sorghum, sugar cane, triticale, or wheat; of the family Polygonaceae, optionally buckwheat; of the family Rosaceae, optionally almonds, apples, apricots, blackberry, blueberry, cherries, peaches, plums, quinces, raspberries, roses, or strawberries; of the family Solanaceae, optionally bell peppers, chili peppers, eggplant, *petunia*, potato, tobacco, or tomato; or of the family Vitaceae, optionally grape.

112. Use of a *Pseudomonas*, optionally a *P. koreensis*, optionally *P. koreensis* NRRL B-67883, for treating a plant growth medium, optionally a soil.

113. Use of a biologically pure culture of *Pseudomonas*, optionally a *P. koreensis*, optionally *P. koreensis* NRRL B-67883, for treating a plant growth medium, optionally a soil.

114. Use of a composition comprising one or more strains of *Pseudomonas*, optionally a *P. koreensis*, optionally *P. koreensis* NRRL B-67883, for treating a plant growth medium, optionally a soil.

115. A method of making a seed treatment, comprising, consisting essentially of or consisting of: inoculating a culture medium with the isolated strain of paragraph 1 or the biologically pure culture of paragraph 2, incubating the inoculated culture medium at a temperature of about 4 to about 37° C. until the *P. koreensis* NRRL B-67883 density therein is about $1\times10^3$ to about $1\times10^{12}$ colony-forming units (cfu) per milligram and/or milliliter of inoculated culture medium, optionally about/at least $1\times10^3$, $1\times10^4$, $1\times10^5$, $1\times10^6$, $1\times10^7$, $1\times10^8$, $1\times10^9$, $1\times10^{10}$, $1\times10^{11}$, or $1\times10^{12}$ colony forming units per milligram/milliliter, and collecting *P. koreensis* NRRL B-67883 from the inoculated culture medium under conditions suitable for producing a seed treatment.

116. A synthetic microbial consortium, comprising, consisting essentially of or consisting of the isolated strain of paragraph 1 and one or more additional microorganisms, optionally one or more symbtiotic diazotrophs and/or one or more phosphate-solubilizing microorganisms.

The present disclosure extends to close relatives of strains of the present disclosure, including, but not limited to, closely related progeny of *P. koreensis* NRRL B-67883 (e.g., progeny having a 16S sequence that is about/at least 95, 95.5, 95.55, 95.6, 95.65, 95.7, 95.75, 95.8, 95.85, 95.9, 95.95, 96, 96.05, 96.1, 96.15, 96.2, 96.25, 96.3, 96.35, 96.4, 96.45, 96.5, 96.55, 96.6, 96.65, 96.7, 96.75, 96.8, 96.85, 96.9, 96.95, 97, 97.5, 97.55, 97.6, 97.65, 97.7, 97.75, 97.8, 97.85, 97.9, 97.95, 98, 98.05, 98.1, 98.15, 98.2, 98.25, 98.3, 98.35, 98.4, 98.45, 98.5, 98.55, 98.6, 98.65, 98.7, 98.75, 98.8, 98.85, 98.9, 98.95, 99, 99.05, 99.1, 99.15, 99.2, 99.25, 99.3, 99.35, 99.4, 99.45, 99.5, 99.55, 99.6, 99.65, 99.7, 99.75, 99.8, 99.85, 99.9, 99.91, 99.92, 99.93, 99.94, 99.95, 99.96, 99.97, 99.98, 99.99 or 100% identical to SEQ ID NO: 1 and/or a whole genome sequence that is about/at least 95, 95.5, 95.55, 95.6, 95.65, 95.7, 95.75, 95.8, 95.85, 95.9, 95.95, 96, 96.05, 96.1, 96.15, 96.2, 96.25, 96.3, 96.35, 96.4, 96.45, 96.5, 96.55, 96.6, 96.65, 96.7, 96.75, 96.8, 96.85, 96.9, 96.95, 97, 97.5, 97.55, 97.6, 97.65, 97.7, 97.75, 97.8, 97.85, 97.9, 97.95, 98, 98.05, 98.1, 98.15, 98.2, 98.25, 98.3, 98.35, 98.4, 98.45, 98.5, 98.55, 98.6, 98.65, 98.7, 98.75, 98.8, 98.85, 98.9, 98.95, 99, 99.05, 99.1, 99.15, 99.2, 99.25, 99.3, 99.35, 99.4, 99.45, 99.5, 99.55, 99.6, 99.65, 99.7, 99.75, 99.8, 99.85, 99.9 or 99.95% identical to the whole genome sequence of *P. koreensis* NRRL B-67883), closely related modified microbial strains derived from *P. koreensis* NRRL B-67883 (e.g., modified microbial strains derived from *P. koreensis* NRRL B-67883 and having a 16S sequence that is about/at least 95, 95.5, 95.55, 95.6, 95.65, 95.7, 95.75, 95.8, 95.85, 95.9, 95.95, 96, 96.05, 96.1, 96.15, 96.2, 96.25, 96.3, 96.35, 96.4, 96.45, 96.5, 96.55, 96.6, 96.65, 96.7, 96.75, 96.8, 96.85, 96.9, 96.95, 97, 97.5, 97.55, 97.6, 97.65, 97.7, 97.75, 97.8, 97.85, 97.9, 97.95, 98, 98.05, 98.1, 98.15, 98.2, 98.25, 98.3, 98.35, 98.4, 98.45, 98.5, 98.55, 98.6, 98.65, 98.7, 98.75, 98.8, 98.85, 98.9, 98.95, 99, 99.05, 99.1, 99.15, 99.2, 99.25, 99.3, 99.35, 99.4, 99.45, 99.5, 99.55, 99.6, 99.65, 99.7, 99.75, 99.8, 99.85, 99.9, 99.91, 99.92, 99.93, 99.94, 99.95, 99.96, 99.97, 99.98, 99.99 or 100% identical to SEQ ID NO: 1 and/or a whole genome sequence that is about/at least 95, 95.5, 95.55, 95.6, 95.65, 95.7, 95.75, 95.8, 95.85, 95.9, 95.95, 96, 96.05, 96.1, 96.15, 96.2, 96.25, 96.3, 96.35, 96.4, 96.45, 96.5, 96.55, 96.6, 96.65, 96.7, 96.75, 96.8, 96.85, 96.9, 96.95, 97, 97.5, 97.55, 97.6, 97.65, 97.7, 97.75, 97.8, 97.85, 97.9, 97.95, 98, 98.05, 98.1, 98.15, 98.2, 98.25, 98.3, 98.35, 98.4, 98.45, 98.5, 98.55, 98.6, 98.65, 98.7, 98.75, 98.8, 98.85, 98.9, 98.95, 99, 99.05, 99.1, 99.15, 99.2, 99.25, 99.3, 99.35, 99.4, 99.45, 99.5, 99.55, 99.6, 99.65, 99.7, 99.75, 99.8, 99.85, 99.9 or 99.95% identical to the whole genome sequence of *P. koreensis* NRRL B-67883), closely related modified microbial strains derived from progeny of *P. koreensis* NRRL B-67883 (e.g., modified microbial strains derived from one or more progeny of *P. koreensis* NRRL B-67883 and having a 16S sequence that is about/at least 95, 95.5, 95.55, 95.6, 95.65, 95.7, 95.75, 95.8, 95.85, 95.9, 95.95, 96, 96.05, 96.1, 96.15, 96.2, 96.25, 96.3, 96.35, 96.4, 96.45, 96.5, 96.55, 96.6, 96.65, 96.7, 96.75, 96.8, 96.85, 96.9, 96.95, 97, 97.5, 97.55, 97.6, 97.65, 97.7, 97.75, 97.8, 97.85, 97.9, 97.95, 98, 98.05, 98.1, 98.15, 98.2, 98.25, 98.3, 98.35, 98.4, 98.45, 98.5, 98.55, 98.6, 98.65, 98.7, 98.75, 98.8, 98.85, 98.9, 98.95, 99, 99.05, 99.1, 99.15, 99.2, 99.25, 99.3, 99.35, 99.4, 99.45, 99.5, 99.55, 99.6, 99.65, 99.7, 99.75, 99.8, 99.85, 99.9, 99.91, 99.92, 99.93, 99.94, 99.95, 99.96, 99.97, 99.98, 99.99 or 100% identical to SEQ ID NO: 1 and/or a whole genome sequence that is about/at least 95, 95.5, 95.55, 95.6, 95.65, 95.7, 95.75, 95.8, 95.85, 95.9, 95.95, 96, 96.05, 96.1, 96.15, 96.2, 96.25, 96.3, 96.35, 96.4, 96.45, 96.5, 96.55, 96.6, 96.65, 96.7, 96.75, 96.8, 96.85, 96.9, 96.95, 97, 97.5, 97.55, 97.6, 97.65, 97.7, 97.75, 97.8, 97.85, 97.9, 97.95, 98, 98.05, 98.1, 98.15, 98.2, 98.25, 98.3, 98.35, 98.4, 98.45, 98.5, 98.55, 98.6, 98.65, 98.7, 98.75, 98.8, 98.85, 98.9, 98.95, 99, 99.05, 99.1, 99.15, 99.2, 99.25, 99.3, 99.35, 99.4, 99.45, 99.5, 99.55, 99.6, 99.65, 99.7, 99.75, 99.8, 99.85, 99.9 or 99.95% identical to the whole genome sequence of *P. koreensis* NRRL B-67883), and other closely related strains (e.g., *Pseudomonas* strains having a 16S sequence that is about/at least 95, 95.5, 95.55, 95.6, 95.65, 95.7, 95.75, 95.8, 95.85, 95.9, 95.95, 96, 96.05, 96.1, 96.15, 96.2, 96.25, 96.3, 96.35, 96.4, 96.45, 96.5, 96.55, 96.6, 96.65, 96.7, 96.75, 96.8, 96.85, 96.9, 96.95, 97, 97.5, 97.55, 97.6, 97.65, 97.7, 97.75, 97.8, 97.85, 97.9, 97.95, 98, 98.05, 98.1, 98.15, 98.2, 98.25, 98.3, 98.35, 98.4, 98.45, 98.5, 98.55, 98.6, 98.65, 98.7, 98.75, 98.8, 98.85, 98.9, 98.95, 99, 99.05, 99.1, 99.15, 99.2, 99.25, 99.3, 99.35, 99.4, 99.45, 99.5, 99.55, 99.6, 99.65, 99.7, 99.75, 99.8, 99.85, 99.9, 99.91, 99.92, 99.93, 99.94, 99.95, 99.96, 99.97, 99.98, 99.99 or 100% identical to SEQ ID NO: 1 and/or a whole genome sequence that is about/at least 95, 95.5, 95.55, 95.6, 95.65, 95.7, 95.75, 95.8, 95.85, 95.9, 95.95, 96, 96.05, 96.1, 96.15, 96.2, 96.25, 96.3, 96.35, 96.4, 96.45, 96.5, 96.55, 96.6, 96.65, 96.7, 96.75, 96.8, 96.85, 96.9, 96.95, 97, 97.5, 97.55, 97.6, 97.65, 97.7, 97.75, 97.8, 97.85, 97.9, 97.95, 98, 98.05, 98.1, 98.15, 98.2, 98.25, 98.3, 98.35, 98.4, 98.45, 98.5, 98.55, 98.6, 98.65, 98.7, 98.75, 98.8, 98.85, 98.9, 98.95, 99, 99.05, 99.1, 99.15, 99.2, 99.25, 99.3, 99.35, 99.4, 99.45, 99.5, 99.55, 99.6, 99.65, 99.7, 99.75, 99.8, 99.85, 99.9 or 99.95% identical to the whole genome sequence of *P. koreensis* NRRL B-67883), which may themselves be useful for enhancing the growth and/or yield of various plants, including, but not limited to, cereals and pseudocereals, such as barley, buckwheat, corn, millet, oats, *quinoa*, rice, rye, sorghum and wheat, and legumes, such as alfalfa, beans, carob, clover, guar, lentils, mesquite, peas, peanuts, soybeans, tamarind, tragacanth and vetch.

Thus, it is to be understood that the present disclosure encompasses isolated microbial strains, biologically pure cultures, inoculant compostions, non-naturally occurring compositions, plants, plant parts, processed products, crops, kits, methods and uses, such as those set forth in the numbered paragraphs above, in which one or more closely related progeny of *P. koreensis* NRRL B-67883, one or more closely related modified microbial strains derived from *P. koreensis* NRRL B-67883, one or more closely related modified microbial strains derived from progeny of *P. koreensis* NRRL B-67883, and/or one or more other close relatives of *P. koreensis* NRRL B-67883 is/are substituted for *P. koreensis* NRRL B-67883.

Deposit of Biological Materials

*Pseudomonas koorensis* NRRL B-67883 was isolated from a soil sample and deposited on Nov. 14, 2019, at the Agricultural Research Service Culture Collection, 1815 North University Street, Peoria, Illinois 61604. U.S.A. under the terms of the Budapest Treaty on the International Recognition of the Deposit of Microorganisms for the Purposes of Patent Procedure and in compliance with 37 C.F.R. 1.801-1.809.

*Pseudomonas koorensis* NRRL B-67883 was deposited under conditions that assure access to the culture will be available during the pendency of this patent application to one determined by the Commissioner of Patents and Trademarks to be entitled thereto under 37 C.F.R. § 1.14 and 35 U.S.C. § 122. Each deposit represents a pure culture of the deposited strain. Each deposit is available as required by foreign patent laws in countries wherein counterparts of the subject application or its progeny are filed. However, it should be understood that the availability of a deposit does not constitute a license to practice the subject invention in derogation of patent rights granted by governmental action.

EXAMPLES

The following examples are not intended to be a detailed catalogue of all the different ways in which the present disclosure may be implemented or of all the features that may be added to the present disclosure. Subjects skilled in the art will appreciate that numerous variations and additions to the various embodiments may be made without departing from the present disclosure. Hence, the following descriptions are intended to illustrate some particular embodiments of the invention and not to exhaustively specify all permutations, combinations and variations thereof.

Example 1

Strain Isolation

*Pseudomonas* koorensis NRRL B-67883 was isolated from a soil sample collected in Salem, Virginia. Soil samples were serially diluted in phosphate buffer, plated on a variety of solid media, and incubated at 30° C. until colonies were visible. Cultures were purified using a sterile loop to transfer a portion of a single colony to fresh medium and streaking for isolation. Soil extract agar contained 1.0 g glucose, 0.50 g dipotassium phosphate, 17.75 g soil extract, and 15 g agar per liter, and the pH was adjusted to 6.8 prior to autoclaving. Standard method agar contained 2.5 g tryptone yeast extract, 1.0 g dextrose, and 15 g agar per liter, and the pH was adjusted to 7 prior to autoclaving. Tryptic soy agar contained 15 g pancreatic digest of casein, 5 g papaic digest of soybean, 5 g sodium chloride and 15 g agar per liter. YEM agar contained 1 g yeast extract, 10 g mannitol, 0.5 g dipotassium phosphate, 0.2 g magnesium sulfate, 0.1 g sodium chloride, and 15 g agar per liter, and the pH was adjusted to 6.8 prior to autoclaving.

Example 2

Identification and Sequencing of Strains

The isolated strain deposited as NRRL B-67883 was identified as *Pseudomonas koorensis* by MALDI Biotyper and 16S sequencing. MALDI Biotyping was performed using a Bruker MALDI-TOF (Matrix Assisted Laser Desorption Ionization-Time of Flight) Mass Spectrometer. NRRL B-67883 was applied to targets using the direct application method and the resulting protein spectrums were compared against the Bruker BDAL library and an internal Novozymes library of named microbial strains. 16S ribosomal DNA sequences were determined by colony PCR and Sanger sequencing with degenerate primers targeting the 16S ribosomal gene sequences. The 16S rDNA sequence for *Pseudomonas koorensis* NRRL B-67883 is provided as SEQ ID NO: 1.

(Pseudomonas koorensis NRRL B-67883 16S sequence)
SEQ ID NO: 1
TTCAGCGGCGGACGGGTGAGTAATGCCTAGGAATCT

GCCTGGTAGTGGGGGACAACGTTTCGAAAGGAACG

CTAATACCGCATACGTCCTACGGGAGAAAGCAGGG

GACCTTCGGGCCTTGCGCTATCAGATGAGCCTAGG

TCGGATTAGCTAGTTGGTGAGGTAATGGCTCACCA

AGGCGACGATCCGTAACTGGTCTGAGAGGATGATC

AGTCACACTGGAACTGAGACACGGTCCAGACTCCT

ACGGGAGGCAGCAGTGGGGAATATTGGACAATGGG

CGAAAGCCTGATCCAGCCATGCCGCGTGTGTGAAG

AAGGTCTTCGGATTGTAAAGCACTTTAAGTTGGGA

GGAAGGGTTGTAGATTAATACTCTGCAATTTTGAC

GTTACCGACAGAATAAGCACCGGCTAACTCTGTGC

CAGCAGCCGCGGTAATACAGAGGGTGCAAGCGTTA

ATCGGAATTACTGGGCGTAAAGCGCGCGTAGGTGG

TTCGTTAAGTTGGATGTGAAATCCCCGGGCTCAAC

CTGGGAACTGCATCCAAAACTGGCGAGCTAGAGTA

TGGTAGAGGGTGGTGGAATTTCCTGTGTAGCGGTG

AAATGCGTAGATATAGGAAGGAACACCAGTGGCGA

AGGCGACCACCTGGACTGATACTGACACTGAGGTG

CGAAAGCGTGGGGAGCAAACAGGATTAGATACCCT

GGTAGTCCACGCCGTAAACGATGTCAACTAGCCGT

TGGGAGCCTTGAGCTCTTAGTGGCGCAGCTAACGC

ATTAAGTTGACCGCCTGGGGAGTACGGCCGCAAGG

TTAAAACTCAAATGAATTGACGGGGGCCCGCACAA

GCGGTGGAGCATGTGGTTTAATTCGAAGCAACGCG

AAGAACCTTACCAGGCCTTGACATCCAATGAACTT

TCCAGAGATGGATTGGTGCCTTCGGGAACATTGAG

ACAGGTGCTGCATGGCTGTCGTCAGCTCGTGTCGT

GAGATGTTGGGTTAAGTCCCGTAACGAGCGCAACC

CTTGTCCTTAGTTACCAGCACGTTATGGTGGGCAC

TCTAAGGAGACTGCCGGTGACAAACCGGAGGAAGG

TGGGGATGACGTCAAGTCATCATGGCCCTTACGGC

CTGGGCTACACACGTGCTACAATGGTCGGTACAGA

GGGTTGCCAAGCCGCGAGGTGGAGCTAATCCCACA

AAACCGATCGTAGTCCGGATCGCAGTCTGCAACTC

GACTGCGTGAAGTCGGAATCGCTAGTAATCGCGAA

-continued
TCAGAATGTCGCGGTGAATACGTTCCCGGGCCTTG

TACACACCGCCCGTCACACCATGGGAGTGGGTT

Example 3

*Pseudomonas koorensis* NRRL B-67883 Exhibited Iron Chelation

*Pseudomonas koorensis* NRRL B-67883 was grown on an iron-free LB agar plate overnight at 30° C. Agar containing chrome azurol S and hexadecyltrimethylammonium bromide was overlaid on the aforementioned plate and incubated for three hours at 30° C. *Pseudomonas koorensis* NRRL B-67883 colonies exhibited zones of clearing indicative of iron chelation, suggesting the colonies produced one or more siderophores capable of freeing iron, thereby making it available for plant uptake.

Example 4

*Pseudomonas koorensis* NRRL B-67883 Exhibited Zinc Solubilization

*Pseudomonas koorensis* NRRL B-67883 was grown on zinc oxide or zinc carbonate plates for seven days at 28° C. *Pseudomonas koorensis* NRRL B-67883 colonies exhibited zones of clearing indicative of zinc solubilization.

Example 5

*Pseudomonas koreensis* NRRL B-67883 Enhanced *Arabidopsis* Shoot Growth

*Pseudomonas koreensis* NRRL B-67883 stock was streaked on an isolation plate of R2A media and incubated overnight. A single colony from the plate was used to inoculate 4 mL of R2A liquid media, then incubated at 30° C. and 200 RPM overnight. Agar plates for *Arabidopsis thaliana* growth were made with 50% Murishage and Skoog (MS) media, without supplemental sugars added. *Arabidopsis thaliana* (Col-0) seeds were gas sterilized and bleach sterilized, then applied to MS plates. Plates with seeds applied were cold treated at 4° C. for 48 hours. The liquid *Pseudomonas koreensis* NRRL B-67883 cultures were diluted to an OD of 0.01, and 100 μl of the diluted cultures were spread on MS agar plates and left to dry in a sterile hood. Cold-treated *Arabidopsis thaliana* (Col-0) seeds were then transferred to the microbe-treated plates, or to untreated control plates, 5 equally spaced seedlings per plate. Replicates of 3 plates were used per experiment. Treated and untreated control plates were placed vertically under plant growth lights at room temperature and left to grow for 6 days. After 6 days, the roots and shoots of each plant were weighed. Seedlings grown on plates treated with *Pseudomonas koreensis* NRRL B-67883 exhibited significantly larger shoot weights, as compared to seedlings grown on untreated control plates.

Example 6

*Pseudomonas koreensis* NRRL B-67883 Increased Boron and Iron Content in Corn

Bare corn seed was inoculated with *Pseudomonas koreensis* NRRL B-67883 (~$10^6$ cfu per seed). Treated seeds and untreated control seeds were sown in a growth chamber in custom-made soils comprising a 4:1 mixture of sand and BM2 soil mix. A subset of the untreated control seeds were sidedressed by introducing *Pseudomonas korensis* NRRL B-67883 (~$10^6$ cfu per seed) into a 1"×2" trough adjacent the seeds. Seeds were grown at 25° C. and 60% relative humidity under a 16 hr/8 hr light cycle with filtered milliQ water. Plants were harvested after three weeks. DNA was extracted from total root system samples and assayed using genomic quantitiave PCR (qPCR) with strain-specific primers to test for the presence of *Pseudomonas korensis* NRRL B-67883. Leaf tissue was analysed for nutrient content. *Pseudomonas korensis* NRRL B-67883 was present on the roots of plants grown from seeds treated prior to planting and plants grown from sidedressed seeds. *Pseudomonas korensis* NRRL B-67883 was not present on the roots of plants grown from untreated, unsidedressed seeds. Plants grown from seeds treated with *Pseudomonas koorensis* NRRL B-67883, whether prior to planting or as a sidedressing, exhibited increased boron content ($p<0.05$ prior to planting; $p<0.0001$ sidedressing), as compared to plants grown from untreated, unsidedressed control seeds. Plants grown from seeds treated with *Pseudomonas koorensis* NRRL B-67883 prior to planting also exhibited increased iron content ($p<0.0001$), as compared to plants grown from untreated, unsidedressed seeds.

Example 7

*Pseudomonas koorensis* NRRL B-67883 Increased Corn Boron Content and Iron Content

*Pseudomonas koorensis* NRRL B-67883 was grown in liquid culture medium, and then frozen in 15% glycerol prior to use. The frozen culture was later thawed, diluted to a predetermined concentration, and applied to the surface of hybrid corn seeds in a rotating mechanical drum to promote even microbe distribution and achieve a desired number of colony-forming units per seed. After the microbes were applied to the surface of the seeds, an overtreatment mixture comprising a polymer, colorant, and water was subsequently applied to the seeds to aid with sticking the microbe to the seeds. After these treatment steps, the seeds were allowed to continue tumbling for another 2 minutes for the seeds to dry. The same stock of frozen cultures was sent to a field trial location near Jackson, Mississippi for liquid furrow application for the trial.

Three treatments (untreated control seed, treated seed, and untreated control seed inoculated by liquid in furrow) were randomly blocked in three field plots for analysis of plant nutrient content and root persistence. For in furrow application, a liquid furrow treater attached to the planter delivered a liquid application of the strain at a five gallon per acre rate, to target of ~$1\times10^6$ cfu per seed. Each plot corresponded to two rows of about 15 feet in length and a row spacing of about 30 inches (i.e., a planting density of about 36,000 plants/acre).

Plants in each treatment were sampled at V2-3 and V7-8 stages (full development of the $8^{th}$ leaf), corresponding to 4 and 10 weeks, respectively. DNA was extracted from total root system samples and assayed using genomic quantitate PCR (qPCR) with strain-specific primers to test for the presence of *Pseudomonas korensis* NRRL B-67883. At 10 weeks, leaf tissue was analysed for nutrient content. *Pseudomonas korensis* NRRL B-67883 was present on the roots of plants grown from seeds treated prior to planting and plants grown from seeds treated in furrow. *Pseudomonas korensis* NRRL B-67883 was not present on the roots of plants grown from untreated seeds. Plants grown from seeds treated with *Pseudomonas koorensis* NRRL B-67883, whether prior to planting or as a sidedressing, exhibited increased boron content ($p<0.05$), as compared to plants grown from untreated control seeds. Plants grown from seeds treated with *Pseudomonas koorensis* NRRL B-67883 prior to planting also exhibited increased iron content ($p<0.05$), as compared to plants grown from untreated seeds.

Example 8

*Pseudomonas koorensis* NRRL B-67883 Increased Corn Root Length and Diameter

Bare corn seed was inoculated with *Pseudomonas koorensis* NRRL B-67883 (~$1\times10^5$ cfu per seed). Treated seeds and untreated control seeds were grown in custom-made soils using a 4:1 mixture of sand and BM2 soil mix and placed in a growth chamber at 25° C. under a 16 hr/8 hr light cycle with filtered milliQ water for approximately six days. After six days, plants grown from seeds treated with *Pseudomonas koorensis* NRRL B-67883 exhibited increased root length ($p=0.0313$) and root diameter ($p=0.616$), as compared to plants grown from untreated control seeds.

Example 9

*Pseudomonas koorensis* NRRL B-67883 Enhanced Corn Yield

*Pseudomonas koorensis* NRRL B-67883 was grown in liquid culture medium, and then frozen in 15% glycerol prior to use. The frozen culture was later thawed, diluted to a predetermined concentration, and applied to the surface of hybrid corn seeds in a rotating mechanical drum to promote even microbe distribution and achieve a desired number of colony-forming units per seed. After the microbes were applied to the surface of the seeds, an overtreatment mixture comprising a polymer, colorant, and water was subsequently applied to the seeds to aid with sticking the microbe to the seeds. After these treatment steps, the seeds were allowed to continue tumbling for another 2 minutes for the seeds to dry. The same stocks of frozen cultures were sent to field trial locations liquid furrow application for the trial.

The hybrid corn seeds were tested in broad acre yield (BAY) trials in 2018 at 28 field locations across a variety of corn-growing geographies within the United States utilizing a randomized complete block design—trials contained multiple control plots that were averaged by replicate (and by germplasm when more than one germplasm was used in a trial). The relative maturity of the germplasms tested in each year was matched to the geographical location (RM103, RM110 and RM113 in Year 1; RM101-103, RM110-111 and RM112-116 in Year 2; RM95-105, RM105-110 and RM110-120 in Year 3). The hybrid corn seeds were pretreated with ipconozole, metalaxyl and azoxystrobin. At each location testing the strain, five reps were conducted at each field location, with a total of 224 plots tested for each strain, and each plot corresponding to two rows of about 15 feet in length and a row spacing of about 30-38 inches (i.e., a planting density of about 34,000-36,000 plants/acre). For treatments corresponding to in furrow (over seed) application, the strain was delivered at a 5 gallons per acre rate, resulting in ~$1\times10^6$ cfu per seed.

At harvest, yield measurements from individual plots were combined and yield was calculated using the shell weight (SHW) for corn as well as moisture (MST), according to the following formula: corn yield=((100−MST)/84.5)×(SHW/56)×(43560/(length×width)).

When the strain was applied in furrow with viable CFU counts (84 plots), the delta yield over the untreated control was 5.26 bushels per acre (p=0.04).

Example 10

*Pseudomonas koorensis* NRRL B-67883 Enhanced Corn Yield

*Pseudomonas koreensis* NRRL B-67883 are grown in liquid culture medium, and then frozen in 15% glycerol prior to use. The frozen culture are later thawed, diluted to a predetermined concentration, and over-treated to the surface of hybrid corn seeds, with existing fungicide and insecticide seed treatments in a high-speed, centrifugal seed treater for 10 seconds to promote even microbe distribution and achieve a desired number of colony-forming units per seed. After these treatment steps, the seeds are allowed to dry in a cool room to maintain colony numbers.

The hybrid corn seeds are tested in small-plot research trials of 300-400 sqft per plot in 2020 at 30 field locations across a variety of corn-growing geographies within the United States utilizing a randomized complete block design—trials contained multiple control plots that were averaged by replicate (each site used one of four chosen hybrids provided by Novozymes). The hybrid corn seeds are pretreated with ipconazole, metalaxyl and azoxystrobin. At each location testing the strain, six reps are conducted at each field location, with a total of 180 plots tested for each individual strain as well as the combination treatments, and each plot corresponding to two rows of about 30-40 feet in length and a row spacing of about 30 inches (i.e., a planting density of about 30,000-36,000 plants/acre).

At harvest, yield measurements from individual plots are averaged and yield is calculated using the shell weight (SHW) for corn as well as moisture (MST), according to the following formula: corn yield=((100−MST)/84.5)×(SHW/56)×(43560/(harvested length×harvested width)). Final stand counts are collected to verify expected plant density to verify plot yield differences are not the result of fewer plants/acre an individual plot.

Plants grown from seeds treated with *Pseudomonas koorensis* NRRL B-67883 exhibit increased yield, as compared to plants grown from untreated control seeds.

APPENDIX A

*Acinetobacter, Actinomycetes, Aegerita, Agrobacterium* (e.g., *A. radiobacter* strains such as K1026 and K84), *Akanthomyces, Alcaligenes, Alternaria, Aminobacter* (e.g., *A. aganoensis, A. aminovorans, A. anthyllidis, A. ciceronei, A. lissarensis, A. niigataensis), Ampelomyces* (e.g., *A. quisqualis* strains such as M-10), *Anabaena* (e.g., *A. aequalis, A. affinis, A. angstumalis angstumalis, A. angstumalis marchita, A. aphanizomendoides, A. azollae, A. bornetiana, A. catenula, A. cedrorum, A. circinalis, A. confervoides, A. constricta, A. cyanobacterium, A. cycadeae, A. cylindrica, A. echinispora, A. felisii, A. flos-aquae flos-aquae, A. flos-aquae minor, A. flos-aquae treleasei, A. helicoidea, A. inaequalis, A. lapponica, A. laxa, A. lemmermannii, A. levanderi, A. limnetica, A. macrospora macrospora, A. macrospora robusta, A. monticulosa, A. nostoc, A. ascillarioides, A. planctonica, A. raciborski, A. scheremetievi, A. spha-erica, A. spiroides crassa, A. spiroides sprroides, A. subcylindrica, A. torulosa, A. unispora, A. variabilis, A. verrucosa, A. viguieri, A. wisconsinense, A. zierlingii), Arthrobacter, Arthrobotrys* (e.g., *A. aggregata, A. alaskana, A. ameropora, A. anomala, A. apscheronica, A. arthrobotryoides, A. azerbaijanica, A. bakunika, A. botryospora, A. brochopaga, A. chazarica, A. chilensis, A. cladodes, A. calvispora, A. compacta, A. conoides, A. constringens, A. cylindrospora, A. dactyloides, A. deflectans, A. dendroides, A. doliiformis, A. drechsleri, A. elegans, A. ellipsospora, A. entomopaga, A. ferox, A. foliicola, A. fruticulosa, A. globospora, A. hatospora, A. hertziana, A. indica, A. irregularis, A. javanica, A. kirghizica, A. longa, A. longiphora, A. longiramulifera, A. longispora, A. mangrovispora, A. megaspora, A. microscaphoides, A. microspora, A. multisecundaria, A. musiformis, A. nematopaga, A. nonseptata, A. oligospora, A. oudemansii, A. oviformis, A. perpasta, A. polycephala, A. pseudoclavata, A. pyriformis, A. recta, A. robusta, A. rosea, A. scaphoides, A. sclerohypha, A. shahriari, A. shizishanna, A. sinensis, A. soprunovii, A. stilbacea, A. straminicola, A. superba, A. tabrizica, A. venusta, A. vermicola, A. yunnanensis), Aschersonia, Ascophaera, Aspergillus* (e.g., *A. flavus* strains such as NRRL 21882, *A. parasiticus), Aulosira* (e.g., *A. aenigmatica, A. africana, A. bohemensis, A. bombayensis, A. confluens, A. fertilissima, A. fertilissma* var. *tenius, A. fritschii, A. godoyana, A. implexa, A. laxa, A. plantonica, A. prolifica, A. pseudoramosa, A. schauinslandii, A. striata, A. terrestris, A. thermalis), Aureobacterium, Aureobasidium* (e.g., *A. pullulans* strains such as DSM 14940 and DSM 14941), *Azobacter, Azorhizobium* (e.g., *A. caulinodans, A. doebereinerae, A. oxalatiphilum), Azospirillum* (e.g., *A. amazonense* strains such as BR 11140 (SpY2T), *A. brasilense* strains such as INTA Az-39, AZ39, XOH, BR 11002, BR 11005, Ab-V5 and Ab-V6, *A. canadense, A. doebereinerae, A. formosense, A. halopraeferans, A. irakense, A. largimobile, A. lipoferum* strains such as BR 11646, *A. melinis, A. oryzae, A. picis, A. rugosum, A. thiophilum, A. zeae), Azotobacter* (e.g., *A. agilis, A. armeniacus, A.* sp. *AR, A. beijerinckii, A. chroococcum, A.* DCU26, *A.* FAB, *A. nigricans, A. paspali, A. salinestris, A. tropicalis, A. vinelandii), Bacillus* (e.g., *B. amyloliquefaciens* strains such as D747, NRRL B-50349, TJ1000 (also known as 1BE, isolate ATCC BAA-390), FZB24, FZB42, IN937a, IT-45, TJ1000, MBI600, BS27 (deposited as NRRL B-5015), BS2084 (deposited as NRRL B-50013), 15AP4 (deposited as ATCC PTA-6507), 3AP4 (deposited as ATCC PTA-6506), LSSA01 (deposited as NRRL B-50104), ABP278 (deposited as NRRL B-50634), 1013 (deposited as NRRL B-50509), 918 (deposited as NRRL B-50508), 22CP1 (deposited as ATCC PTA-6508) and BS18 (deposited as NRRL B-50633), *B. cereus* strains such as I-1562, *B. firmus* strains such as I-1582, *B. laevolacticus, B. lichenformis* strains such as BA842 (deposited as NRRL B-50516) and BL21 (deposited as NRRL B-50134), *B. macerns, B. firmus, B. mycoides* strains such as NRRL B-21664, *B. pasteurii, B. pumilus* strains such as NRRL B-21662, NRRL B-30087, ATCC 55608, ATCC 55609, GB34, KFP9F and QST 2808, *B. sphaericus, B. subtilis* strains such as ATCC 55078, ATCC 55079, MBI 600, NRRL B-21661, NRRL B-21665, CX-9060, GB03, GB07, QST 713, FZB24, D747 and 3BP5 (deposited as NRRL B-50510), *B. thuringiensis* strains such as ATCC 13367, GC-91, NRRL B-21619, ABTS-1857, SAN 401

I, ABG-6305, ABG-6346, AM65-52, SA-12, SB4, ABTS-351, HD-1, EG 2348, EG 7826, EG 7841, DSM 2803, NB-125 and NB-176), *Beijerinckia, Beauveria* (e.g., *B. bassiana* strains such as ATCC 26851, ATCC 48023, ATCC 48585, ATCC 74040, ATCC-74250, DSM 12256 and PPRI 5339), *Beijerinckia, Blastodendrion, Bosea* (e.g., *B. eneae, B. lathyri, B. lupini, B. massiliensis, B. minatitlanensis, B. robiniae, B. thiooxidans, B. vestrisii*), *Bradyrhizobium* (e.g., *B. arachidis, B. bete, B. canariense, B. cytisi, B. daqingense, B. denitrificans, B. diazoefficiens, B. elkanii* strains such as SEMIA 501, SEMIA 587 and SEMIA 5019, *B. ganzhouense, B. huanghuauhaiense, B. icense, B. ingae, B. iriomotense, B. japonicum* strains such as 61A227, 61A228, 61A273, E-109 NRRL B-50586 (also deposited as NRRL B-59565), NRRL B-50587 (also deposited as NRRL B-59566), NRRL B-50588 (also deposited as NRRL B-59567), NRRL B-50589 (also deposited as NRRL B-59568), NRRL B-50590 (also deposited as NRRL B-59569), NRRL B-50591 (also deposited as NRRL B-59570), NRRL B-50592 (also deposited as NRRL B-59571), NRRL B-50593 (also deposited as NRRL B-59572), NRRL B-50594 (also deposited as NRRL B-50493), NRRL B-50608, NRRL B-50609, NRRL B-50610, NRRL B-50611, NRRL B-50612, NRRL B-50726, NRRL B-50727, NRRL B-50728, NRRL B-50729, NRRL B-50730, SEMIA 566, SEMIA 5079, SEMIA 5080, USDA 6, USDA 110, USDA 122, USDA 123, USDA 127, USDA 129 and USDA 532C, *B. jicamae, B. lablabi, B. liaoningense, B. manausense, B. neotropicale, B. oligotrophicum, B. ottawaense, B. pachyrhizi, B. paxllaeri, B. retamae, B. rifense, B. valentinum, B. yuanmingense*), *Burkholderia* (e.g., *B. acidipaludis, B. ambifaria, B. andropogonis, B. anthina, B. arboris, B. bannensis, B. bryophila, B. caledonica, B. caribensis, B. caryophylli, B. cenocepacua, B. choica, B. cocovenenans, B. contaminans, B. denitrificans, B. diazotrophica, B. diffusa, B. dilworthii, B. dolosa, B. eburnea, B. endofungorum, B. ferrariae, B. fungorum, B. ginsengisoli, B. gladioli, B. glathei, B. glumae, B. graminis, B. grimmiae, B. heleia, B. hospital, B. humi, B. kururiensis, B. lata, B. latens, B. mallei, B. megapolitana, B. metallica, B. mimosarum, B. multivorans, B. nodosa, B. norimbergensis, B. oklahomensis, B. phenazinium, B. phenoliruptrix, B. phymatum, B. phytofirmans, B. pickettii, B. plantarii, B. pseudomallei, B. pseudomultivorans, B. pyrrocinia, B. rhizoxinica, B. rhynchosiae, B. sabiae, B. sacchari, B. sartisoli, B. sediminicola, B. seminalis, B. silvatlantica, B. singaporensis, B. soli, B. sordidcola, B.* sp. strains such as A396, *B. sprentiae, B. stabilis, B. symbiotica, B. telluris, B. terrae, B. terrestris, B. terricola, B. thailandensis, B. tropica, B. tuberum, B. ubonensis, B. udeis, B. unamae, B. vandii, B. vietnamiensis, B. xenovorans, B. zhejiangensis*), *Brevibacillus, Burkholderia* (e.g., *B.* sp. A396 nov. rinojensis NRRL B-50319), *Calonectria, Candida* (e.g., *C. oleophila* such I-182, *C. saitoana*), *Candidatus* (e.g., *C. Burkholderia calva, C. Burkholderia crenata, C. Burkholderia hispidae, C. Burkholderia kirkii, C. Burkholderia mamillata, C. Burkholderia nigropunctata, C. Burkholderia rigidae, C. Burkholderia schumannianae, C. Burkholderia verschuerenii, C. Burkholderia vixens, C. Phytoplasma allocasuarinae, C. Phytoplasma americanum, C. Phytoplasma asteris, C. Phytoplasma aurantifolia, C. Phytoplasma australiense, C. Phytoplasma balanitae, C. Phytoplasma brasiliense, C. Phytoplasma caricae, C. Phytoplasma castaneae, C. Phytoplasma cocosnigeriae, C. Phytoplasma cocostanzaniae, C. Phytoplasma convolvuli, C. Phytoplasma costaricanum, C. Phytoplasma cynodontis, C. Phytoplasma fragariae, C. Phytoplasma fraxini, C. Phytoplasma graminis, C. Phytoplasma japonicum, C. Phytoplasma luffae, C. Phytoplasma lycopersici, C. Phytoplasma malasianum, C. Phytoplasma mali, C. Phytoplasma omanense, C. Phytoplasma oryzae, C. Phytoplasma palmae, C. Phytoplasma palmicola, C. Phytoplasma phoenicium, C. Phytoplasma pini, C. Phytoplasma pruni, C. Phytoplasma prunorum, C. Phytoplasma pyri, C. Phytoplasma rhamni, C. Phytoplasma rubi, C. Phytoplasma solani, C. Phytoplasma spartii, C. Phytoplasma sudamericanum, C. Phytoplasma tamaricis, C. Phytoplasma trifolii, C. Phytoplasma ulmi, C. Phytoplasma vitis, C. Phytoplasma ziziphi*), *Chromobacterium* (e.g., *C. subtsugae* NRRL B-30655 and PRAA4-1, *C. vaccinia* strains such as NRRL B-50880, *C. violaceum*), *Chryseomonas, Clavibacter, Clonostachys* (e.g., *C. rosea* f. *catenulata* (also referred to as *Gliocladium catenulatum*) strains such as J1446), *Clostridium, Coelemomyces, Coelomycidium, Colletotrichum* (e.g., *C. gloeosporioides* strains such as ATCC 52634), *Comomonas, Conidiobolus, Coniothyrium* (e.g., *C. minitans* strains such as CON/M/91-08), *Cordyceps, Corynebacterium, Couchia, Cryphonectria* (e.g., *C. parasitica*), *Cryptococcus* (e.g., *C. albidus*), *Cryptophlebia* (e.g., *C. leucotreta*), *Culicinomyces, Cupriavidus* (e.g., *C. alkaliphilus, C. basilensis, C. campinensis, C. gilardii, C. laharis, C. metallidurans, C. numazuensis, C. oxalaticus, C. pampae, C. pauculus, C. pinatubonensis, C. respiraculi, C. taiwanensis*), *Curtobacterium, Cydia* (e.g., *C. pomonella* strains such as V03 and V22), *Dactylaria* (e.g., *D. candida*), *Delftia* (e.g., *D. acidovorans* strains such as RAY209), *Desulforibtio, Desulfovibrio, Devosia* (e.g., *D. neptuniae*), *Dilophosphora* (e.g., *D. alopecuri*), *Engyodontium, Enterobacter, Entomophaga, Entomophthora, Erwinia* (e.g., *E. billingiae* strains such as NRRL B-67766), *Erynia, Escherichia* (e.g., *E. intermedia*), *Eupenicillium, Exiguobacaterium, Filariomyces, Filobasidiella, Flavobacterium* (e.g., F. H492 NRRL B-50584), *Frankia* (e.g., *F. alni*), *Fusarium* (e.g., *F. laterium, F. oxysporum, F. solani*), *Gibellula, Gigaspora* (e.g., *G. margarita*), *Gliocladium* (e.g., *G. virens* strains such as ATCC 52045 and GL-21), *Glomus* (e.g., *G. aggregatum, G. brasilianum clarum, G. deserticola, G. etunicatum, G. fasciculatum, G. intraradices* strains such as RTI-801, *G. monosporum, G. mosseae*), *Gluconobacter, Halospirulina, Harposporium* (e.g., *H. anguillulae*), *Hesperomyces, Hirsutella* (e.g., *H. minnesotensis, H. rhossiliensis, H. thomsonii* strains such as ATCC 24874), *Hydrogenophage, Hymenoscyphous* (e.g., *H. ericae*), *Hymenostilbe, Hypocrella, Isaria* (e.g., *I. fumosorosea* strains such as Apopka-97 (deposited as ATCC 20874)), *Klebsiella* (e.g., *K. pneumoniae, K. oxytoca*), *Kluyvera, Laccaria* (e.g., *L. bicolor, L. laccata*), *Lactobacillus, Lagenidium, Lecanicillium* (e.g., *L. lecanii* strains such as KV01, *L. longisporum* strains such as KV42 and KV71), *Leptolegnia, Lysobacter* (e.g., *L. antibioticus* strains such as 13-1 and HS124, *L. enzymogenes* strains such as 3.1T8), *Massospora, Meristacrum* (e.g., *M. asterospermum*), *Mesorhizobium* (e.g., *M. abyssinicae, M. albiziae, M. alhagi, M. amorphae, M. australicum, M. camelthorni, M. caraganae,*

*M. chacoense, M. ciceri, M. gobiense, M. hawassense, M. huakuii* strains such as LL32, *M. loti, M. mediterraneum, M. metallidurans, M. muleiense, M. opportunistum, M. plurifarium, M. qingshengii, M. robiniae, M. sangaii, M. septentrionale, M. shangrilense, M. shonense, M. silamurunense, M. tamadayense, M. tarimense, M. temperatum, M. thiogangeticum, M. tianshanense), Metarhizium* (e.g., *M. anisopliae* (also referred to as *M. brunneum, Metarrhizium anisopliae,* and green muscadine) strains such as IMI 330189, FI-985, FI-1045, F52 (deposited as DSM 3884, DSM 3885, ATCC 90448, SD 170 and ARSEF 7711) and ICIPE 69), *M. flavoviride* strains such as ATCC 32969), *Methylobacterium* (e.g., *M. adhaesivum, M. aerolatum, M. aminovorans, M. aquaticum, M. brachiatum, M. brachythecii, M. bullatum, M. cerastii, M. chloromethanicum, M. dankookense, M. dichloromethanicum, M. extorquens, M. fujisawaense, M. gnaphalii, M. goesingense, M. gossipiicola, M. gregans, M. haplocladii, M. hispanicum, M. iners, M. isbiliense, M. jeotgali, M. komagatae, M. longum, M. lusitanum, M. marchantiae, M. mesophilicum, M. nodulans, M. organophilum, M. oryzae, M. oxalidis, M. persicinum, M. phyllosphaerae, M. platani, M podarium, M. populi, M. radiotolerans, M. rhodesianum, M. rhodinum, M. salsuginis, M. soli, M. suomiense, M. tardum, M. tarhaniae, M. thiocyanatum, M. thurigiense, M. trifolii, M. variabile, M. zatmanii), Metschnikowia* (e.g., *M. fructicola), Microbacterium* (e.g., *M. laevaniformans, M. trichothecenolyticum* strains such as NRRL B-67602 and NRRL B-67822), *Microdochium* (e.g., *M. dimerum), Microsphaeropsis* (e.g., *M. ochracea* P130A), *Microvirga* (e.g., *M. aerilata, M. aerophila, M. flocculans, M. guangxiensis, M. lotononidis, M. lupini, M. subterranea, M. vignae, M. zambiensis), Monacrosporium* (e.g., *M. cionopagum), Mucor, Muscodor* (e.g., *M. albus* such NRRL 30547, QST 20799 and SA-13, *M. roseus* strains such as NRRL 30548), *Mycoderma, Myiophagus, Myriangium, Myrothecium* (e.g., *M. verrucaria), Nectria, Nematoctonus* (e.g., *N. geogenius, N. leiosporus), Neozygites, Nomuraea* (e.g., *N. rileyi* strains such as SA86101, GU87401, SR86151, CG128 and VA9101), *Nostoc* (e.g., *N. azollae, N. caeruleum, N. carneum, N. comminutum, N. commune, N. ellipsosporum, N. flagelliforme, N. linckia, N. longstaffi, N. microscopicum, N. muscorum, N. paludosum, N. pruniforme, N. punctifrome, N. sphaericum, N. sphaeroides, N. spongiaeforme, N. verrucosum), Ochrobactrum* (e.g., *O. anthropi, O. cicero, O. cytisi, O. daejeonense, O. gallinifaecis, O. grigonense, O. guangzhouense, O. haematophilum, O. intermedium, O. lupini, O. oryzae, O. pectoris, O. pituitosum, O. pseudointermedium, O. pseudogrignonense, O. rhizosphaerae, O. thiophenivorans, O. tritici), Oidiodendron, Paecilomyces* (e.g., *P. fumosoroseus* strains such as FE991 and FE9901, *P. lilacinus* strains such as 251, DSM 15169 and BCP2), *Paenibacillus* (e.g., *P. alvei* strains such as NAS6G6, *P. azotofixans, P. polymyxa* strains such as ABP166 (deposited as NRRL B-50211)), *Pandora, Pantoea* (e.g., *P. agglomerans* strains such as NRRL B-21856, *P. vagans* strains such as C9-1), *Paraglomus* (e.g., *P. brazilianum), Paraisaria, Pasteuria, Pasteuria* (e.g., *P. nishizawae* strains such as Pn1, *P. penetrans, P. ramose, P. sp.* strains such as ATCC PTA-9643 and ATCC SD-5832, *P. thornea, P. usage), Penicillium* (e.g., *P. albidum, P. aurantiogriseum, P. bilaiae* (formerly known as *P. bilaii* and *P. bilaji*) strains such as ATCC 18309, ATCC 20851, ATCC 22348, NRRL 50162, NRRL 50169, NRRL 50776, NRRL 50777, NRRL 50778, NRRL 50777, NRRL 50778, NRRL 50779, NRRL 50780, NRRL 50781, NRRL 50782, NRRL 50783, NRRL 50784, NRRL 50785, NRRL 50786, NRRL 50787, NRRL 50788 and RS7B-SD1, *P. brevicompactum* strains such as AgRF18, *P. canescens* strains such as ATCC 10419, *P. chyrsogenum, P. citreonigrum, P. citrinum, P. digitatum, P. expansum* strains such as ATCC 24692 and YT02, *P. fellatanum* strains such as ATCC 48694, *P. frequentas, P. fuscum, P. fussiporus, P. gaestrivorus* strains such as NRRL 50170, *P. glabrum* strains such as DAOM 239074 and CBS 229.28, *P. glaucum, P. griseofulvum, P. implicatum, P. janthinellum* strains such as ATCC 10455, *P. lanosocoeruleum* strains such as ATCC 48919, *P. lilacinum, P. minioluteum, P. montanense, P. nigricans, P. oxalicum, P. pinetorum, P. pinophilum, P. purpurogenum, P. radicum* strains such as ATCC 201836, FRR 4717, FRR 4719 and N93/47267, *P. raistrickii* strains such as ATCC 10490, *P. rugulosum, P. simplicissimum, P. solitum, P. variabile, P. velutinum, P. viridicatum), Phingobacterium, Phlebiopsis* (e.g., *P. gigantea), Photorhabdus, Phyllobacterium* (e.g., *P. bourgognense, P. brassicacearum, P. catacumbae, P. endophyticum, P. ifriqiyense, P. leguminum, P. loti, P. myrsinacearum, P. sophorae, P. trifolii), Pichia* (e.g., *P. anomala* strains such as WRL-076), *Pisolithus* (e.g., *P. tinctorius), Planktothricoides, Plectonema, Pleurodesmospora, Pochonia* (e.g., *P. chlamydopora), Podonectria, Polycephalomyces, Prochlorocoous* (e.g., *P. marinus), Prochloron* (e.g., *P. didemni), Prochlorothrix, Pseudogibellula, Pseudomonas* (e.g., *P. agarici, P. antartica, P. aurantiaca, P. aureofaciens, P. azotifigens, P. azotoformans, P. balearica, P. blatchfordae, P. brassicacearum, P. brenneri, P. cannabina, P. cedrina, P. cepacia, P. chlororaphis* strains such as MA 342, *P. congelans, P. corrugata, P. costantinii, P. denitrificans, P. entomophila, P. fluorescens* strains such as ATCC 27663, CL 145A and A506, *P. fragii, P. fuscovaginae, P. fitiva, P. gessardii* strains such as NRRL B-67767, *P. jessenii* strains such as PS06, *P. kilonensis, P. koreensis, P. libanensis* strains such as NRRL B-67769, *P. lili, P. lundensis, P. lutea, P. luteola, P. mandelii, P. marginalis, P. meditrranea, P. meridana, P. migulae, P. moraviensis, P. mucidolens, P. orientalis, P. oryzihabitans, P. palleroniana, P. panacis, P. parafulva, P. peli, P. peoriae* strains such as NRRL B-67884, NRRL B-67885, O14M94, O232WW, O23AY3, O24EJU, O24F5T, O24UYG, O53QFV, O62QGV and O72SXC, *P. pertucinogena, P. plecoglossicida, P. protogens, P. proteolytica, P. putida, P. pyrocina* strains such as ATCC 15958, *P. rhodesiae, P. sp.* strains such as DSM 13134, *P. striata, P. stutzeri, P. syringae, P. synxantha, P. taetrolens, P. thisvervalensis, P. tolaasii, P. veronii), Pseudozyma* (e.g., *P. flocculosa* strains such as PF-A22 UL), *Pythium* (e.g., *P. oligandrum* strains such as DV 74), *Rhizobium* (e.g., *R. aggregatum, R. alamii, R. alkalisoli, P. alvei, P. azibense, P. borbori, R. calliandrae, R. cauense, R. cellulosilyticum, R. daejeonense, R. endolithicum, R. endophyticum, R. etli, R. fabae, R. flavum, R. fredii, R. freirei, R. galegae, R. gallicum, R. giardinii, R. grahamii, R. hainanense, R. halophytocola, R. halotolerans, R. helanshanense, R. herbae, R. huautlense, R. indigoferae, R. jaguaris, R. kunmingense, R. laguerreae, R. larrymoorei, R. leguminosarum* strains such as 162BB1, 162P17, 175G10b, D36 and SO12A-2 (IDAC 080305-01), *R. lemnae, R. leucaenae, R. loessense, R. loti* strains such as 95C11 and 95C14, *R. lupini, R. lusitanum, R. mayense, R. mesoamericanum, R. mesosinicum, R. miluonense, R. mongolense, R. multihospitium, R. naphthalenivorans, R. nepotum, R. oryzae, R. pakistanensis, R. paknamense, R. paranaense, R. petrolearium, R. phaseoli, R. phenanthrenilyticum, R. pisi, R. pongamiae, R. populi, R. pseudoryzae, R. pusense, R. qilianshanese, r. radiobacter, R. rhizogenes, R. rhizoryzae, R. rozettiformans, R. rubi, R. selenitireeducens, R. skierniewicense, R. smilacinae, R. soli, R. sophorae, R. sophoriradicis, R. sphaerophysae, R. straminoryzae, R. subbaraonis, R. sullae, R. taibaishanense, R. tarimense, R. tibeticum, R. trifolii* strains such as RP113-7, *R. tropici* strains such as SEMIA 4080, *R. tubonense, R. undicola, R. vallis, R. viciae* strains such as P1NP3Cst, SU303 and WSM 1455, *R. vignae, R. vitis, R. yanglingense, R. yantingense*), *Rhizoctonia, Rhizopogon* (e.g., *R. amylopogon, R. fulvigleba, R. luteolus, R. villosuli*), *Rhodococcus, Saccharopolyspora* (e.g., *S. spinosa*), *Scleroderma* (e.g., *S. cepa S. citrinum*), *Septobasidium, Serratia, Shinella* (e.g., *S. kummerowiae*), *Sinorhizoium* (e.g., *S. abri, S. adhaerens, S. americanum, S. arboris, S. chiapanecum, S. fredii* strains such as CCBAU114 and USDA 205, *S. garamanticus, S. indiaense, S. kostiense, S. kummerowiae, S. medicae, S. meliloti* strains such as 102F34a, 102F51a, 102F77b, B401 and MSDJ0848, *S. mexicanus, S. numidicus, S. psoraleae, S. saheli, S. sesbaniae, S. sojae, S. terangae, S. xinjiangense*), *Sorosporella, Sphaerodes* (e.g., *S. mycoparasitica* strains such as IDAC 301008-01), *Spodoptera* (e.g., *S. littoralis*), *Sporodiniella, Steinernema* (e.g., *S. carpocapsae, S. feltiae, S. kraussei* strains such as L137), *Stenotrophomonas, Streptomyces* (e.g., *S.* NRRL B-30145, *S.* M1064, *S.* WYE 53 (deposited as ATCC 55750), *S. cacaoi* strains such as ATCC 19093, *S. galbus* strains such as NRRL 30232, *S. griseoviridis* strains such as K61, *S. lydicus* strains such as WYEC 108 (deposited as ATCC 55445), *S. violaceusniger* strains such as YCED-9 (deposited as ATCC 55660)), *Streptosporangium, Stillbella, Swaminathania, Talaromyces* (e.g., *T. aculeatus, T. flavus* strains such as V117b), *Tetranacrium, Thiobacillus, Tilachlidium, Tolypocladium, Tolypothrix, Torrubiella, Torulospora, Trenomyces, Trichoderma* (e.g. *T. asperellum* strains such as SKT-1, *T. atroviride* strains such as LC52 and CNCM 1-1237, *T. fertile* strains such as JM41R, *T. gamsii* strains such as ICC 080, *T. hamatum* strains such as ATCC 52198, *T. harzianum* strains such as ATCC 52445, KRL-AG2, T-22, TH-35, T-39 and ICC012, *T. polysporum, T. reesi* strains such as ATCC 28217 *T. stromaticum, T. virens* strains such as ATCC 58678, GL-3, GL-21 and G-41, *T. viridae* strains such as ATCC 52440, ICC080 and TV1), *Typhula, Ulocladium* (e.g., *U. oudemansii* strains such as HRU3), *Uredinella, Variovorax, Verticillium* (e.g., *V. chlamydosporum, V. lecanii* strains such as ATCC 46578), *Vibrio, Xanthobacter, Xanthomonas, Xenorhabdus, Yersinia* (e.g., *Y. entomophaga* strains such as O82KB8), *Zoophthora*

That which is claimed:

1. A non-naturally occurring inoculant composition comprising *Pseudomonas koreensis* NRRL B-67883 in an agriculturally acceptable carrier.

2. The composition of claim 1, said composition comprising at least 1×104 colony-forming units (CFU) of *Pseudomonas koreensis* NRRL B-67883 per gram of said composition and/or at least 1×104 colony-forming units (CFU) of *Pseudomonas koreensis* NRRL B-67883 per milliliter of said composition.

3. The composition of claim 1, wherein said agriculturally acceptable carrier comprises one or more maltodextrins.

4. The composition of claim 1, wherein said agriculturally acceptable carrier comprises one or more disaccharides.

5. The composition of claim 1, wherein said agriculturally acceptable carrier comprises one or more sugar alcohols.

6. The composition of claim 1, wherein said agriculturally acceptable carrier comprises one or more maltodextrins and one or more disaccharides.

7. The composition of claim 1, wherein said agriculturally acceptable carrier comprises one or more maltodextrins and one or more sugar alcohols.

8. The composition of claim 1, wherein said agriculturally acceptable carrier comprises one or more maltodextrins, one or more disaccharides, and one or more sugar alcohols.

9. The composition of claim 1, wherein said agriculturally acceptable carrier is a powder or granule.

10. The composition of claim 1, wherein said agriculturally acceptable carrier is an aqueous liquid.

11. The composition of claim 1, wherein said agriculturally acceptable carrier is a non-aqueous liquid.

12. A method comprising introducing the composition of claim 1 into a plant growth medium.

13. A method comprising contacting a plant seed with the composition of claim 1.

14. A method comprising contacting a plant with the composition of claim 1.

15. A plant seed that is at least partially coated with the composition of claim 1.

16. A method comprising inoculating a culture medium with *Pseudomonas koreensis* NRRL B-67883 and incubating the inoculated culture medium at a temperature of about 4° C. to about 37° C., thereby producing an incubation product that comprises *Pseudomonas koreensis* NRRL B-67883.

17. A method comprising introducing one or more stabilizers into the incubation product of claim 16, said one or more stabilizers comprising one or more maltodextrins and/or one or more disaccharides and/or one or more sugar alcohols.

18. A method comprising isolating *Pseudomonas koreensis* NRRL B-67883 from the incubation product of claim 16.

19. A kit comprising the incubation product of claim 16 and one or more stabilizers, said one or more stabilizers comprising one or more maltodextrins and/or one or more disaccharides and/or one or more sugar alcohols.

20. A method comprising contacting a plant or plant part with the incubation product of claim 16.

* * * * *